US007709519B2

(12) United States Patent
Hirano et al.

(10) Patent No.: US 7,709,519 B2
(45) Date of Patent: May 4, 2010

(54) BENZIMIDAZOLYLIDENE PROPANE-1,3 DIONE DERIVATIVE OR SALT THEREOF

(75) Inventors: Masaaki Hirano, Chuo-ku (JP); Eiji Kawaminami, Chuo-ku (JP); Isao Kinoyama, Chuo-ku (JP); Shunichiro Matsumoto, Chuo-ku (JP); Kei Ohnuki, Chuo-ku (JP); Kazuyoshi Obitsu, Chuo-ku (JP); Toshiyuki Kusayama, Chuo-ku (JP)

(73) Assignee: Astellas Pharma Inc., Tokyo (JP)

( * ) Notice: Subject to any disclaimer, the term of this patent is extended or adjusted under 35 U.S.C. 154(b) by 710 days.

(21) Appl. No.: 10/588,485

(22) PCT Filed: Jun. 2, 2005

(86) PCT No.: PCT/JP2005/010184

§ 371 (c)(1), (2), (4) Date: Aug. 4, 2006

(87) PCT Pub. No.: WO2005/118556

PCT Pub. Date: Dec. 15, 2005

(65) Prior Publication Data

US 2009/0018177 A1 Jan. 15, 2009

(30) Foreign Application Priority Data

Jun. 4, 2004 (JP) ............................ 2004-166486
Mar. 30, 2005 (JP) ............................ 2005-099815

(51) Int. Cl.
*A01N 43/52* (2006.01)

(52) U.S. Cl. .................................... 514/394; 548/304.4

(58) Field of Classification Search ................. 514/394; 548/304.4
See application file for complete search history.

(56) References Cited

U.S. PATENT DOCUMENTS

| | | | |
|---|---|---|---|
| 4,062,686 | A | 12/1977 | Van Allan et al. |
| 4,119,466 | A | 10/1978 | Van Allan et al. |
| 4,263,393 | A | 4/1981 | Chen |
| 4,636,509 | A | 1/1987 | Phillipps et al. |
| 4,946,960 | A | 8/1990 | Wade et al. |
| 4,950,640 | A | 8/1990 | Evans et al. |
| 4,966,828 | A | 10/1990 | Doenges et al. |
| 5,055,579 | A | 10/1991 | Pawlowski et al. |
| 5,064,747 | A | 11/1991 | Imai et al. |
| 5,104,783 | A | 4/1992 | Shimada et al. |
| 5,112,743 | A | 5/1992 | Kamiya et al. |
| 5,141,841 | A | 8/1992 | Wade |
| 5,202,221 | A | 4/1993 | Imai et al. |
| 5,385,807 | A | 1/1995 | Okamoto et al. |
| 5,445,930 | A | 8/1995 | Harada et al. |
| 5,519,136 | A | 5/1996 | Wade |
| 5,593,818 | A | 1/1997 | Kawamoto |
| 5,616,537 | A | 4/1997 | Yokota et al. |
| 5,738,982 | A | 4/1998 | Harada et al. |
| 5,747,235 | A | 5/1998 | Farid et al. |
| 5,747,236 | A | 5/1998 | Farid et al. |
| 5,770,544 | A | 6/1998 | Yokota et al. |
| 5,817,819 | A | 10/1998 | Furuya et al. |
| 5,994,051 | A | 11/1999 | Gould et al. |
| 6,051,359 | A | 4/2000 | Ohkawa et al. |
| 6,087,503 | A | 7/2000 | Furuya et al. |
| 6,140,384 | A | 10/2000 | Sorori et al. |
| 6,153,371 | A | 11/2000 | Farid et al. |
| 6,162,813 | A | 12/2000 | Goulet et al. |
| 6,346,534 | B1 | 2/2002 | Zhu et al. |
| 6,395,733 | B1 | 5/2002 | Arnold et al. |
| 6,413,503 | B1 | 7/2002 | Habeck et al. |
| 6,468,711 | B1 | 10/2002 | Sorori et al. |
| 6,960,591 | B2 | 11/2005 | Hirano et al. |
| 2002/0177556 | A1 | 11/2002 | Engel et al. |
| 2003/0191164 | A1 | 10/2003 | Hirano et al. |

(Continued)

FOREIGN PATENT DOCUMENTS

CA 2415010 A1 1/2002

(Continued)

OTHER PUBLICATIONS

U.S. Appl. No. 11/887,384.

(Continued)

*Primary Examiner*—Kamal A Saeed
*Assistant Examiner*—Valerie Rodriguez-Garcia
(74) *Attorney, Agent, or Firm*—Sughrue Mion, PLLC

(57) ABSTRACT

Compounds useful as GnRH receptor antagonists are provided. The present inventors have further examined propane-1,3-dione derivatives and confirmed as a result that a propane-1,3-dione having 2-(1,3-dihydro-2H-benzimidazol-2-ylidene), or a compound which has benzene or thiophene ring substituted with a group derived from 1-hydroxymethyl, shows excellent availability, in addition to its excellent GnRH receptor antagonism, thereby accomplishing the invention. Since the compound of the invention shows excellent availability, in addition to its strong GnRH receptor antagonism, it can be expected that it exerts superior drug effect in the living body, and it is useful for the treatment of sex hormone dependent diseases such as prostate cancer, breast cancer, endometriosis, uterine leiomyoma, benign prostatic hypertrophy and the like. In addition, since the compound of the invention is excellent in metabolic stability in human and also is less in drug interaction, it has more desirable properties as a medicament to be used for the aforementioned diseases.

21 Claims, No Drawings

U.S. PATENT DOCUMENTS

| | | | |
|---|---|---|---|
| 2004/0029040 | A1 | 2/2004 | Watanabe et al. |
| 2005/0267110 | A1 | 12/2005 | Hirano |

FOREIGN PATENT DOCUMENTS

| | | | |
|---|---|---|---|
| CN | 1440391 | | 9/2003 |
| DE | 224422 | A1 | 3/1985 |
| EP | 333156 | A2 | 9/1989 |
| EP | 713143 | A2 | 5/1996 |
| EP | 780730 | A2 | 6/1997 |
| EP | 1 300 398 | A1 | 4/2003 |
| EP | 1 752 452 | A1 | 2/2007 |
| JP | 56-161538 | A | 12/1981 |
| JP | 59-064840 | A | 4/1984 |
| JP | 62-006254 | A | 1/1987 |
| JP | 63-032542 | A | 2/1988 |
| JP | 63-271341 | A | 11/1988 |
| JP | 01-205130 | A | 8/1989 |
| JP | 01-249792 | A | 10/1989 |
| JP | 02-054268 | A | 2/1990 |
| JP | 02-079007 | A | 3/1990 |
| JP | 02-189547 | A | 7/1990 |
| JP | 03-164722 | A | 7/1991 |
| JP | 03-259150 | A | 11/1991 |
| JP | 04-334369 | A | 11/1992 |
| JP | 09-061992 | A | 3/1997 |
| JP | 2000-95767 | | 4/2000 |
| JP | 2000-095767 | A | 4/2000 |
| JP | 2002-088284 | A | 3/2002 |
| JP | 2002-241758 | A | 8/2002 |
| JP | 2002-268239 | A | 9/2002 |
| JP | 2004-061583 | A | 2/2004 |
| WO | WO 9804562 | A1 | 2/1998 |
| WO | WO 9952888 | A1 | 10/1999 |
| WO | WO 2002/002533 | A1 | 1/2002 |
| WO | 02/102401 | A1 | 12/2002 |
| WO | 2005/030736 | A1 | 4/2005 |
| WO | WO 2005097090 | A2 | 10/2005 |
| WO | 2005/118556 | A1 | 12/2005 |

OTHER PUBLICATIONS

Charles Huggins et al., "Studies on Prostatic Cancer", Cancer Research, 1, 293-297 (1941).
L. Bokser et al., "Prolonged Inhibition of Luteinizing Hormone and Testosterone Levels in Male Rats with the Luteinizing Hormone-Releasing Hormone Antagonist SB-75", Proc. Natl. Acad. Sci. USA, 87, pp. 7100-7104, Sep. 1990.
Ana Maria Comaru-Schally et al., "Efficacy and Safety of Luteinizing Hormone-Releasing Hormone Antagonist Cetrorelix in the Treatment of Symptomatic Benign Prostatis Hyperplasia," Journal of Clinical Endocrinology and Metabolism, vol. 83, No. 11, pp. 3826-3831 (1998).
I.B. Dzvinchuk et al., Formation of Unsymmetrical 2-(Diacylmethylene)-2,3-Dihydro-1 H-Benzimidazoles During Acidolysis of 1-Benzoyl-2-((3-Benzoyloxy-(3-Phenylvinyl)-1 H-Benzimidazole), Chemistry of Heterocyclic Compounds, 37(5), 554-559 (2001).
Sema Ozturk et al., "Crystal Structure of 2-Dibenzoylmethyl Benzimidazole", Analytical Sciences, vol. 17,pp. 1133-1134, (2001).
Manfred Augustin et al, "Synthesis and reactions of 2,2-diacylketene heteroacetals", Zeitschrift fuer Chemie(1980), 20(3), 96-7.
Junko Ishida et al., "Antitumor Agents. Part 214 : Synthesis and Evaluation of Curcumin Analogues as Cytotoxic Agents," Bioorganic & Medicinal Chemistry 10 (2002) 3481-3487.
Science of Synthesis, "Product Subclass 17: 1,1-Bis(nitrogen—functionalized) Alk—1-enes" , 24, 571-705 (2005).
S. Bajusz, et al. "Highly Potent Antagonists of Luteinizing Hormone-Releasing Hormone Free of Edematogenic Effects"; Proc. Natl. Acad. Sci. USA, vol. 85, pp. 1637-1641, Mar. 1988.
John Trachtenberg, et al. "A Phase 3, Multicenter, Open Label, Randomized Study of Abarelix Versus Leuprolide Plus Daily Antiandrogen in Men With Porstate Cancer"; The Journal of Urology, vol. 167, 1670-1674, Apr. 2002, USA.
Takahito Hara, et al. "Suppression of a Pituitary-Ovarian Axis by Chronic Oral Administration of a Novel Nonpeptide Gonadotropin-Releasing Hormone Antagonist, Tak-013, in Cynomolgus Monkeys"; The Journal of Clinical Endocrinology & Metabolism 88(4):1697-1704, Apr. 2003, USA.
Fabio C. Tucci, et al. "3-[(2*R*)-Amino-2-Phenylethyl]-1-(2,6-Difluorobenzyl)-5-(2-Fluoro-3-Methoxyphenyl)-6-Methylpyrimidin-2,4-Dione (NBI 42902) as a Potent and Orally Active Antagonist of the Human Gonadotropin-Releasing Hormone Receptor. Design, Synthesis, and in Vitro and in Vivo Characterization"; J. Med. Chem. 2005, 48, 1169-1178, USA.
Mexican Office Action dated May 26, 2009.
Canadian Office Action dated May 28, 2009.
Simone, Oncology: Introduction, Cecil Textbook of Medicine, 20.sup.th Edition, vol. 1, pp. 1004-1010, 1996.
Huirne et al., PubMed Abstract (Lancet 358(9295):1793-803), Nov. 2001 . . . Gonadotropin-releasing-hormone-receptor antagonists.
Junko lshida et al., "Antitumor Agents. Part 214: .sup . . . dagger. Synthesis and Evaluation of Curcumin Analogues as Cytotoxic Agents" Bioorganic & Medicinal Chemistry 10 (2002) 3481-3487.
Chemistry of Heterocyclic Compounds (New York, NY, United States)(Translation of Khimiya Geterotsiklicheskikh Soedinenii) (2001), 37(5), 554-559 I.B. Dzvinchuk et al., "Formation of Unsymmetrical 2-(Diacylmethylene)-2,3-Dihydro-1H-Benzimidazoles During Acidolysis of 1-Benzoyl2-(.beta.-Benzoyloxy-.beta.-Phenylviny1)-1H-Benzimidazole".
Jaro Komenda et al., Electrochemical Behavior and ESR Spectra of Nitro Substituted Mono-to and Debenzoylmethylenebenzthiazolines and Selenazolies, Collect. Czech. Chem. Commun. (1979), vol. 44(5), pp. 1540-1551.
Collect. Czech. Chem. Commun. (1973), vol. 38(12), pp. 3616-3622. . A. Mistr et al., Organische Lichtempfidliche Stoffe V. Aclmethylenderivate Heterocyclischer Stickstoffhaltiger Basen ALS Sensibilisatoren Lichtempfindlicher Polymerer, Organic light-sensitive substances. Acylmethylene derivatives of heterocyclic nitrogen-containing bases as sensitizers for light-sensitive polymers.
A. Mistr et al., Organische Lichtempfindliche Stoffee II. Benzoylmethylenderivate Heretocyclischer Stickstoffhaltiger Basen ALS Sensibilisatoren Fur Lichtempfinliche Polymere, Collect. Czech. Commun. (1971), vol. 36(1), pp. 150-163.
G.I. Gaeva and K.S. Liadikov, Zh. Nauch. Prikl. Fotogr. Kinematogr. (1971) vol. 16(4), pp. 282-288.. Sensitization of poly(vinyl cinnamate) by derivatives of benzoyl- and dibenzoylmethylenebenzothiazoline and—benzoselenazoline.
The Chemistry and Biological Activity of Synthetic and Natural Compounds: Nitrogen-Containing Heterocycles, vol. 1 (2006), pp. 243-248.
Chemistry of Heterocyclic Compounds (New York, NY, United States)(Translation of Khimiya Geterotsiklicheskikh Soedinenii) (2001), 37(5), 554-559.
*Bioorganic & Medicinal Chemistry Letters*, vol. 15, Issue 11, Jun. 2, 2005, pp. 2894-2897 Synthesis, in vivo and in vitro biological activity of novel azaline B analogs.
Zh. Organic Khim. (1994), 30(6), 909-14.
Bulletin de la Societe Chimique de France (1974), (3-4, Pt. 2), 525-8.
Journal fuer Praktische Chemie (Leipzig) (1979), 321(2), 320-2.
Collection of Czechoslovak Chemical Communications (1978), 43(3), 739-45.
Horumon to Rinsyo (Hormones and Clinical), 46, 46-57 (1998) ABS Gonadotropin releasing hormone is known as a hormone which controls secretion of sex hormones at the highest position, and controls secretion of anterior pituitary hormones luteinizing hormone and follicle-stimulating hormone and sex hormones in sex glands, via a receptor which is present in the anterior pituitary. Since antagonists specific and selective for this GnRH receptor regulate the action of GnRH and control secretion of subordinate LH and FSH and sex hormones, they are expected as preventive or therapeutic agents for sex hormone dependent diseases.
Molecular Endocrinology 14 671-681 2000 Identification of $Phe^{313}$ of the Gonadotropin-Releasing Hormone (GnRH) Receptor as a Site Critical for the Binding of Nonpeptide GnRH Antagonists.

Molecullar and Cellular Endocrin. 144 11-19 1998 Functional analysis of GnRH receptor ligand binding using biotinylated GnRH derivatives.
The Prostate 20 297-310 1992 Effect of microcapsules of luteinizing hormone-releasing hormone antagonist SB-75 and somatostatin analog RC-160 on endocrine status and tumor growth in the Dunning R-3327H rat prostate cancer model.
Endocrinology 137 3430-3436 1996 Chronic administration of the luteinizing hormone-releasing hormone (LHRH) antagonist cetrorelix decreases gonadotrope responsiveness and pituitary LHRH receptor messenger ribonucleic acid levels in rats.
J. Med. Chem. 2005, 48, 1169-1178 3-[(2*R*)-Amino-2-phenylethyl]-1-(2,6-difluorobenzyl)-5-(2-fluoro-3-methoxyphenyl)-6-methylpyrimidin-2,4-dione (NBI 42902) as a Potent and Orally Active Antagonist of the Human Gonadotropin-Releasing Hormone Receptor. Design, Synthesis, and in Vitro and in Vivo Characterization.
Bioorg. Med. Chem. Lett. 14(9) 2269-2274 2004 Synthesis and structure—activity relationships of (*R*)-1-alkyl-3[2-(2-amino)phenethyl]-5-(2-fluorophenyl)-6-methyluracils as human GnRH receptor antagonists.
Bioorg. Med. Chem. Lett. 15(10) 2519-2522 2005 Uracils as potent antagonists of the human gonadotropin-releasing hormone receptor without atropisomers.
Curr.Opin. Drug Discovery Dev. 7, 832-847, 2004 Synthesis of orally active small-molecule gonadotropin-relea sing hormone antagonists.
Bioorg. Med. Chem. Lett. 15(5) 1407-1411 2005 Efficient synthesis of bicyclic oxazolino- and thiazolino[3,2-*c*]pyrimidine-5,7-diones and its application to the synthesis of GnRH antagonists.
Bioorg. Med. Chem. Lett. 15(9) 2265-2269 2005 Benzimidazoles as non-peptide luteinizing hormone-releasing hormone (LHRH) antagonists. Part 3: Discovery of 1-(1H-benzimidazol-5-yl)-3-tert-butylurea derivatives.
J. Med. Chem. 2004, 47, 3483-3486 3-(2-Aminoalkyl)-1-(2,6-difluorobenzyl)-5- (2-fluoro-3-methoxyphenyl)-6-methyl- uracils as Orally Bioavailable Antagonists of the Human Gonadotropin Releasing Hormone Receptor.
Bioorg. Med. Chem. Lett. 14 1795-1798 2004 Syntheses and structure—activity relationship studies of piperidine-substituted quinolones as nonpeptide gonadotropin releasing hormone antagonists.
Bioorg. Med. Chem. Lett. 14 1599-1602 2004 Elimination of antibacterial activities of non-peptide luteinizing hormone-releasing hormone (LHRH) antagonists derived from erythromycin A.
J. Med.Chem. 2004, 47, 1259-1271 Synthesis and Structure-Activity Relationships of 1-Arylmethyl-5-aryl-6-methyluracils as Potent Gonadotropin-Releasing Hormone Receptor Antagonists.
Bioorg. Med. Chem. Lett. 13 3317-3322 2003 Synthesis and Structure—activity relationships of 1-arylmethyl-3-(1-methyl-2-amino)ethyl-5-aryl-6-methyluracils as antagonists of the human GnRH Receptor.
Bioorg. Med. Chem. Lett. 13 3617-3622 2003 Synthesis and structure—Activity relationships of thieno[2,3-*d*]pyrimidine-2,4-dione derivatives as potent GnRH receptor antagonists.
J.Med.Chem. 2004, 47, 1085-1097 Nonpeptide Luteinizing Hormone-Releasing Hormone Antagonists Derived from Erythromycin A: Design, Synthesis, and Biological Activity of Cladinose Replacement Analogues.
J. Pharmaco. Experi. Ther. 305 688-695 2003 Gonadotropin-releasing hormone (GnRH) receptor antagonists have potential in treating numerous hormone-dependent pathologies including cancers of the prostate, breast, and ovary, endometriosis, and fertility disorders.
J. Clin. Endocri. Metab. 88 1697-1704 2003.
Bioorg. Med. Chem. Lett. 13 3311-3315 2003 Synthesis and Structure—Activity relationships of 1-arylmethyl-3-(2-aminopropyl)-5-aryl-6-methyluracils as potent GnRH receptor antagonists.
J.Med.Chem. 2003, 46, 2023-2026 Identification of 1-Arylmethyl-3-(2-aminoethyl)-5-aryluracil as Novel Gonadotropin-Releasing Hormone Receptor Antagonists.
Bioorg. Med. Chem. Lett. 12 2179-2183 2002 Synthesis and initial structure—Activity relationships of a novel series of imidazolo [1,2-*a*]pyrimid-5-ones as potent GnRH receptor antagonists.
Bioorg. Med. Chem. Lett. 12 2185-2187 2002 Design, synthesis and structure—Activity relationships of novel imidazolo[1,2-*a*]pyrimid-5-ones as potent GnRH receptor antagonists.
J.Med.Chem. 2003, 46, 113-124.
Bioorg. Med. Chem. Lett. 12 2073-2077 2002 A new class of potent nonpeptide luteinizing hormone-releasing hormone (LHRH) antagonists: design and synthesis of 2-phenylimidazo[1,2-*a*]pyrimidin-5-ones.
Drugs of the Future 2003, 28, 121-???.
Bioorg. Med. Chem. Lett. 12 3635-3639 2002 Characterization of mono- and diaminopyrimidine derivatives as novel, nonpeptide gonadotropin releasing hormone (GnRH) receptor antagonists.
Bioorg. Med. Chem. Lett. 12 3329-3332 2002 Modification of the pyridine moiety of non-peptidyl indole GnRH receptor antagonists.
Bioorg. Med. Chem. Lett. 12 3467-3470 2002 The discovery of novel small molecule non-peptide gonadotropin releasing hormone (GnRH) receptor antagonists.
Bioorg. Med. Chem. Lett. 12 3491-3495 2002 A novel synthesis of 7-aryl-8-fluoro-pyrrolo[1,2-*a*]pyrimid-4-ones as potent, stable GnRH receptor antagonists.
J.Med.Chem. 2001, 44, 917-922 A Potent, Nonpeptidyl 1*H*-Quinolone Antagonist for the Gonadotropin-Releasing Hormone Receptor.
Bioorg. Med. Chem. Lett. 12 399-402 2002 Initial Structure—Activity Relationship Studies of a Novel Series of Pyrrolo[1,2-*a*]pyrimid-7-ones as GnRH Rcccptor Antagonists.
Bioorg. Med. Chem. Lett. 12 403-406 2002 A Novel Synthesis of 2-Arylpyrrolo[1,2-*a*]pyrimid-7-ones and Their Structure—Activity Relationships as Potent GnRH Receptor Antagonists.
Tetraherdron Lett. 42 6441-6445 2001 Total syntheses of 6- and 7-azaindole derived GnRH antagonists.
Tetraherdron Lett. 42 6459-6461 2001 Synthesis of chiral β-methyl tryptamine-derived GnRH antagonists.
Bioorg. Med. Chem. Lett. 11 2597-2602 2001 Orally bioavailable, indole-based nonpeptide GnRH receptor antagonists with high potency and functional activity.
Bioorg. Med. Chem. Lett. 11 1723-1726 2001 Substituted Indole-5-carboxamides and -acetamides as Potent Nonpeptide GnRH Receptor Antagonists.
Bioorg. Med. Chem. Lett. 11 1727-1731 2001 Potent nonpeptide GnRH receptor antagonists derived from substituted indole-5-carboxamides and—acetamides bearing a pyridine side-chain terminus.
Tetraherdron 57 5233-5241 2001 A convergent synthesis of (*S*)-β-methy1-2-aryltryptamine based gonadotropin releasing hormone antagonists.
Bioorg. Med. Chem. Lett. 15 2519-2522 2005 Uracils as potent antagonists of the human gonadotropin-releasing hormone receptor without atropisomers.
Bioorg. Med. Chem. Lett. 15 4363-4366 2005 Synthesis of aryl-1,2,4-triazine-3,5-diones as antagonists of the gonadotropin-releasing hormone receptor.
Bioorg. Med. Chem. Lett. 15 3685-3690 2005 Structure—activity relationships of 1,3,5-triazine-2,4,6-trioncs as human gonadotropin-releasing hormone receptor antagonists.
Bioorg. Med. Chem. Lett. 15 799-803 2005 Benzimidazole derivatives as novel nonpeptide luteinizing hormone-releasing hormone (LHRH) antagonists. Part 1: Benzimidazole-5-sulfonamides c.
Bioorg. Med. Chem. Lett. 15 805-807 2005 Benzimidazole derivatives as novel nonpeptide luteinizing hormone-releasing hormone (LHRH) antagonists. Part 2: Benzimidazole-5-sulfonamides.
Bioorg. Med. Chem. Lett. 14 2269-2274 2004 Synthesis and structure—activity relationships of (*R*)-1-alkyl-3-[2-(2-amino)phenethyl]-5-(2-fluorophenyl)-6-methyluracils as human GnRH receptor antagonists.
Bioorg. Med. Chem. Lett. 14 5599-5603 2004 Identification of neutral 4-*O*-alkyl quinolone nonpeptide GnRH receptor antagonists.
Bioorg. Med. Chem. Lett. 9 2615-2620 1999 Identification and Initial Structure-Activity Relationships of a Novel Non-Peptide Quinolone GnRH Receptor Antagonist.
Bioorg. Med. Chem. Lett. 9 2621-2624 1999 Investigation of the 4-O-Alkylamine Substituent of Non-Peptide Quinolone GnRH Receptor Antagonists A.

Bioorg. Med. Chem. Lett. 10 1723-1727 2000.
Annual Reports in Medicinal Chemistry vol. 39 99-110, 2004.
J.Med.Chem. 1998, 41, 4190-4195 Discovery of a Novel, Potent, and Orally Active Nonpeptide Antagonist of the Human Luteinizing Hormone-Releasing Hormone (LHRH) Receptor.
Angew. Chem. Int. Ed. Engl. 1997 36 2148-2161 Chemistry and Molecular Biology in the Search for New LHRH Antagonists.
J.Med.Chem. 1989, 32, 2036-2038.
Zcitschrift fuer Chemie (1980), 20(3), 96-7 Synthesis and reactions of 2,2-diacylketene heteroacetals.
The Prostate(1992) 20 297-310.
Bioorg. Med. Chem. Lett. 11 515-517 2001.
Bioorg. Med. Chem. Lett. 11 509-513 2001.
Bioorg. Med. Chem. Lett. 12 93-96 2002.
Bioorg. Med. Chem. Lett. 12 827-832 2002.
J.Med.Chem.(2006), 49, 3809-3825.
Drug of the Future(1999) 24(4) 393-403.
J. Peptide Res.(2005)65 284-291.
Int. J. Peptide Protein Res.(1988) 32 425-435.
J. Clinical Endocrinology and Metabolism(1997) 82 5 1403-1408.
J. Clinical Endocrinology and Metabolism(1992) 75 2 393-398.
Current Pharma. Design(2003) 9 381-390.
Mol. Endocrinology(2000) 14(7) 1099-1115.
JMC(2001) 44 453-467.
Eur J Med Chem(1997) 32 927-940.
JMC(2000) 43 2831-2836.
Bioorganic & Medicinal Chemistry Letters(2005) 15 1609-1612.
PNAS(2002) 99 961-965.
JMC(1997) 40 3739-3748.
JMC(2000) 43 784-796.
JMC(2000) 43 797-806.
JMC(2000) 43 807-818.
JMC(2000) 43 819-828.
JMC(2002) 45 1026-1034.
JMC(2005) 48 4851-4860.
J. Endocrinol., Feb. 1988; 116: 241-246.
Endocrine Rev.(1986) 7 1 44-66.
Current Sci.(1987) 56 7 325-327.
J Endocrinol 1986 108: 101-107.
Neuroendocrinology(1985) 40 246-252.
Endocrinology 1983 113: 195-199.
Biology of Reproduction(1999) 61 1468-1479.
Mol. Endocrinology(1997) 11 11 1659-1668.
Biology of Reproduction(1995) 53 724-731.
Comp. Biochem. Physiol.(1994) 108C 1 129-135.
Current Opinion in Endocrinology & Diabetes(2000) 7 350-356.
J Reprod. Fert.(1992) 96 865-874.
J Clin Endocrinol Metab 1992 75: 1220-1225.
TEM(1992) 3 7 259-263.
J Clin Endocrinol Metab 1994 78: 121-125.
Hormone Res.(1987) 28 88-103.
andrologia(1990) 22 567-573.
Neuroendocrinology(1989) 50 158-16421.
New Zealand Office Action dated Aug. 27, 2009 issued in corresponding New Zealand Application No. 561387 of U.S. Appl. No. 11/887,384.
Russian Office Action issued on Oct. 15, 2009 in Russian Application No. 2007140244/04(044048), which corresponds to the co-pending U.S. Appl. No. 11/887,384.

BENZIMIDAZOLYLIDENE PROPANE-1,3 DIONE DERIVATIVE OR SALT THEREOF

TECHNICAL FIELD

The present invention relates to a novel propane-1,3-dione derivative useful as a medicament, particularly a therapeutic agent for sex hormone dependent diseases.

BACKGROUND OF THE INVENTION

It is known that a hypothalamic hormone or a pituitary hormone is concerned in the secretion controlling mechanism of peripheral hormones. In general, secretion of anterior pituitary hormones is controlled by a secretion accelerating hormone or a secretion inhibiting hormone secreted from its upper central hypothalamus or by a peripheral hormone secreted from a target organ of respective hormone.

Gonadotropin releasing hormone (to be referred to as GnRH hereinafter, and GnRH is also called luteinizing hormone releasing hormone; LHRH) is known as a hormone which controls secretion of sex hormones at the highest position, and controls secretion of anterior pituitary hormones luteinizing hormone (to be referred to as LH hereinafter) and follicle-stimulating hormone (to be referred to as FSH hereinafter) and sex hormones in sex glands, via a receptor which is present in the anterior pituitary (to be referred to as GnRH receptor hereinafter) (Hormone To Rinsho (Hormone and Clinics), a special number for spring, 46, 46-57 (1998)). Since antagonists specific and selective for this GnRH receptor regulate the action of GnRH and control secretion of subordinate LH and FSH and sex hormones, they are expected as preventive or therapeutic agents for sex hormone dependent diseases (aforementioned Hormone and Clinics, a special number for spring (1998)).

To date, peptide compounds cetrorelix (Non-patent Reference 1) and abarelix (Non-patent Reference 2) have been put on the market as GnRH receptor antagonists.

On the other hand, as non-peptide compounds having GnRH receptor antagonism, a thienopyrimidine derivative TAK-013 (Non-patent Reference 3) and a uracil derivative NBI-42902 (Non-patent Reference 4) are now under clinical tests.

In addition, Patent Reference 1 discloses that a propane-1, 3-dione derivative has the GnRH receptor antagonism.

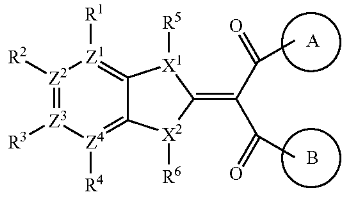

(In the formula, A and B may be the same or different from each other and each represents an aryl which may be substituted or a heteroaryl which may be substituted. See the aforementioned official gazette for details.)

However, there is no illustrative disclosure on a compound which has a 1-hydroxyalkyl group as a substituent group in the ring A or ring B.

[Non-patent Reference 1] *Proc. Natl. Acad. Sci., USA,* 85, 1637-1641, 1988

[Non-patent Reference 2] *J. Urol.,* 167, 1670-1674, 2002

[Non-patent Reference 3] *J. Clin. Endocrinol. Metab.,* 88, 1697-1704, 2003

[Non-patent Reference 4] *J. Med. Chem.,* 2005, 48, 1169-1178

[Patent Reference 1] International Publication WO 02/02533

DISCLOSURE OF THE INVENTION

Problems that the Invention is to Solve

The object of the invention is to provide a medicament which exerts excellent GnRH receptor antagonism in the living body, particularly a novel compound which is useful as a therapeutic agent for prostate cancer, benign prostatic hypertrophy and the like.

Means for Solving the Problem

The present inventors have examined propane-1,3-dione derivatives and confirmed as a result that a propane-1,3-dione having 2-(1,3-dihydro-2H-benzimidazol-2-ylidene), or a compound which has benzene or thiophene ring substituted with a group derived from 1-hydroxyalkyl, shows surprisingly excellent availability by oral administration, in addition to its excellent GnRH receptor antagonism, thereby accomplishing the invention.

That is, the invention relates to a propane-1,3-dione derivative represented by the general formula (I) or a salt thereof. It also relates to a medicament, particularly a GnRH receptor antagonist, which uses them as the active ingredient.

(I)

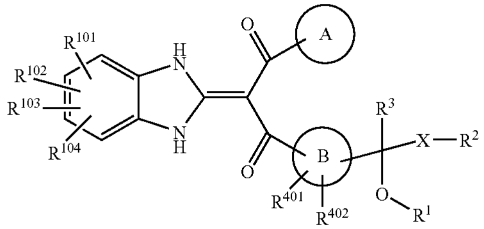

(I)

[Symbols in the formula mean as follows, ring A: benzene which may be substituted, pyridine which may be substituted or thiophene ring, ring B: benzene or thiophene ring, $R^1$: H or —CO-lower alkyl, $R^2$: H, —O—$R^5$, —N($R^6$)$R^7$, —$N_3$, —$S(O)_m$-lower alkyl, —$S(O)_m$—N($R^6$)$R^7$, halogen, pyridyl or -imidazolyl which may be substituted, $R^5$: H, lower alkyl, —CO-lower alkyl which may be substituted, or —CO—O-lower alkyl which may be substituted, $R^6$ and $R^7$: may be the same or different from each other and each is H, lower alkyl, or —CO-lower alkyl, with the proviso that $R^1$ and $R^2$ may together form dioxolane which may be substituted, m: 0, 1 or 2, $R^3$: H or lower alkyl, $R^{401}$ and $R^{402}$: may be the same or different from each other and each is H, halogen, OH, —O-lower alkyl, or lower alkyl, X: bond, lower alkylene which may be substituted, or cycloalkanediyl, $R^{101}$, $R^{102}$, $R^{103}$ and $R^{104}$: may be the same or different from one another and each is H, halogen, OH, or —O-lower alkyl which may be substituted with (aryl or heteroaryl). The same shall apply hereinafter.]

Also this invention is a pharmaceutical composition comprising as an active ingredient the propane-1,3-dione compound represented by the aforementioned general formula (I) or a pharmaceutically acceptable salt thereof and a pharmaceutically acceptable carrier, preferably the pharmaceutical composition which is a GnRH receptor antagonist; and more preferably the pharmaceutical composition wherein the GnRH receptor antagonist is an agent for treating GnRH-related diseases, such as prostate cancer, breast cancer, endometriosis, uterine leiomyoma, and benign prostatic hypertrophy.

Moreover, the present invention provides a method for treating a patient suffering from GnRH-related diseases, which comprises administering to a patient an effective amount of the propane-1,3-dione compound represented by the aforementioned general formula (I) or a pharmaceutically acceptable salt thereof, preferably the method for treating GnRH-related diseases, wherein the GnRH-related diseases are prostate cancer, breast cancer, endometriosis, uterine leiomyoma, and benign prostatic hypertrophy. Furthermore the present invention is use of the GnRH receptor antagonist comprising as an active ingredient the propane-1,3-dione compound represented by the aforementioned general formula (I) or a pharmaceutically acceptable salt thereof and a pharmaceutically acceptable carrier.

ADVANTAGE OF THE INVENTION

Since the compound of the invention shows excellent availability by oral administration, in addition to it strong GnRH receptor antagonism, it can be expected that it exerts stronger drug effect in the living body, and it is useful for the treatment of sex hormone dependent diseases, particularly GnRH-related diseases, such as prostate cancer, breast cancer, endometriosis and uterine leiomyoma (C. Huggins & C. V. Hodges, *Cancer Res.,* 1, 293-297 (1941), L. Bokser et al., *Proc. Natl. Acad. Sci. USA,* 87, 7100-7104 (1990)), benign prostatic hypertrophy (*J. Clin. Endocrinol. Metab.,* 83, 3826-3931, 1998) and the like. In addition, since the compound of the invention is excellent in metabolic stability in human and has weak drug interaction property, it has more desirable properties as a medicament to be used for the aforementioned diseases.

BEST MODE FOR CARRYING OUT THE INVENTION

Preferred embodiments of the invention are shown below.

(1) A propane-1,3-dione derivative or a pharmaceutically acceptable salt thereof, wherein in the general formula (I), ring A is benzene ring which may be substituted with halogen atom or lower alkyl, ring B is benzene ring, $R^1$ is H, $R^2$ is OH, $R^3$ is H, and X is lower alkylene which may be substituted.

(2) The propane-1,3-dione derivative of the aforementioned (1) or a pharmaceutically acceptable salt thereof, wherein X is methylene which may be substituted.

(3) A propane-1,3-dione derivative represented by a general formula (Ia) or a pharmaceutically acceptable salt thereof (Ia)

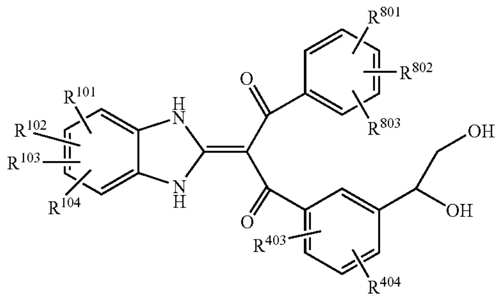

(symbols in the formula mean as follows, $R^{801}$, $R^{802}$ and $R^{803}$: may be the same or different from one another and each is H, halogen or lower alkyl, and $R^{403}$ and $R^{404}$: may be the same or different from each other and each is H, halogen or lower alkyl; the same shall apply hereinafter).

(4) A propane-1,3-dione derivative or a pharmaceutically acceptable salt thereof according to claim 4, or a pharmaceutically acceptable salt thereof, which is at least one compound selected form the group consisting of: 2-(1,3-Dihydro-2H-benzimidazol-2-ylidene)-1-[3-(1,2-dihydroxyethyl)phenyl]-3-(3,4,5-trifluorophenyl)propane-1,3-dione; 1-{2-butyl-3-[(1R)-1,2-dihydroxyethyl]phenyl}-2-(1,3-dihydro-2H-benzimidazol-2-ylidene)-3-(3-fluorophenyl)propane-1,3-dione; 1-(3,5-difluorophenyl)-2-(1,3-dihydro-2H-benzimidazol-2-ylidene)-3-[5-(1,2-dihydroxyethyl)-2-fluorophenyl]propane-1,3-dione; 1-(3,5-difluorophenyl)-2-(1,3-dihydro-2H-benzimidazol-2-ylidene)-3-{3-[(1R)-1,2-dihydroxyethyl]2-methylphenyl}propane-1,3-dione; 2-(1,3-dihydro-2H-benzimidazol-2-ylidene)-1-{3-[(1R)-1,2-dihydroxyethyl]-2-methylphenyl}-3-(2-fluorophenyl) propane-1,3-dione; 2-(1,3-dihydro-2H-benzimidazol-2-ylidene)-1-[3-(1,2-dihydroxyethyl)phenyl]-3-(2,3,5-trifluorophenyl)propane-1,3-dione; 2-(1,3-dihydro-2H-benzimidazol-2-ylidene)-1-{3-[(1R)-1,2-dihydroxyethyl]-2-methylphenyl}-3-(3-methylphenyl)propane-1,3-dione; 1-{2-chloro-3-[(1R)-1,2-dihydroxyethyl]phenyl}-2-(1,3-dihydro-2H-benzimidazol-2-ylidene)-3-(3-fluorophenyl)propane-1,3-dione; 2-(1,3-dihydro-2H-benzimidazol-2-ylidene)-1-{3-[(1R)-1,2-dihydroxyethyl]phenyl}-3-(3- fluorophenyl)propane-1,3-dione; 1-(3,5-difluorophenyl)-2-(1,3-dihydro-2H-benzimidazol-2-ylidene)-3-[3-(1,2-dihydroxyethyl)-2-fluorophenyl]propane-1,3-dione; 1-(3,5-difluorophenyl)-2-(1,3-dihydro-2H-benzimidazol-2-ylidene)-3-[3-(1,2-dihydroxyethyl)-4-fluorophenyl] propane-1,3-dione; 1-{2-chloro-3-[(1R)-1,2-dihydroxyethyl]phenyl}-3-(3,5-difluorophenyl)-2-(1,3-dihydro-2H-benzimidazol-2-ylidene)propane-1,3-dione; 2-(1,3-dihydro-2H-benzimidazol-2-ylidene)-1-{3-[(1R)-1,2-dihydroxyethyl]-2-fluorophenyl}-3-(3-fluorophenyl)propane-1,3-dione; 1-{2-chloro-3-[(1R)-1,2-dihydroxyethyl] phenyl}-3-(3-chlorophenyl)-2-(1,3-dihydro-2H-benzimidazol-2-ylidene)propane-1,3-dione.

(5) A propane-1,3-dione derivative represented by a general formula (Ib) or a pharmaceutically acceptable salt thereof (Ib)

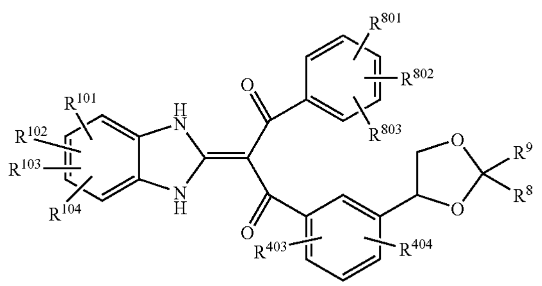

(symbols in the formula mean as follows, $R^8$ and $R^9$: may be the same or different from each other and each is H, lower alkyl, lower alkenyl or —O-lower alkyl; the same shall apply hereinafter).

(6) The propane-1,3-dione derivative of general formula (Ib) or a pharmaceutically acceptable salt thereof, wherein $R^{801}$, $R^{802}$ and $R^{803}$ may be the same or different from one another and each represents H or a halogen atom.

(7) A propane-1,3-dione derivative or a pharmaceutically acceptable salt thereof, which is at least one compound selected from the group consisting of: 2-(1,3-Dihydro-2H-benzimidazol-2-ylidene)-1-(3-fluorophenyl)-3-[3-(2-methoxy-1,3-dioxolan-4-yl)phenyl]propane-1,3-dione; 2-(1,3-dihydro-2H-benzimidazol-2-ylidene)-1-(3-fluorophenyl)-3-[3-(2-methoxy-2-methyl-1,3-dioxolan-4-yl)phenyl] propane-1,3-dione or a pharmaceutically acceptable salt thereof.

The invention is described further in detail.

As the "halogen", fluorine, chlorine, bromine or iodine can be exemplified.

The "lower alkyl" is a straight or branched saturated $C_{1-6}$ alkyl, preferably methyl, ethyl, isopropyl, hexyl or the like.

The "lower alkylene" is a straight or branched saturated $C_{1-6}$alkylene, preferably methylene, ethylene, isopropylene or the like.

The "benzene which may be substituted" and "pyridine which may be substituted" are benzene ring or pyridine ring which may be substituted with 1 to 3 substituent groups, wherein the substituent group is halogen, CN, lower alkyl which may be substituted with halogen, —O-lower alkyl, —CO—O-lower alkyl or amino, preferably halogen or lower alkyl which may be substituted with halogen.

The "imidazolyl which may be substituted" is imidazolyl which may be substituted with 1 or 2 substituent groups, and lower alkyl is desirable as the substituent group.

The "dioxolane which may be substituted" is dioxolane which may be substituted with 1 or 2 substituent groups, and lower alkyl, lower alkenyl, —O-lower alkyl or morpholino-lower alkyl is desirable as the substituent group.

The "lower alkyl which may be substituted" is lower alkyl which may be substituted with 1 or 2 substituent groups, and amino or mono- or di-lower alkylamino is desirable as the substituent group.

The "lower alkylene which may be substituted" is lower alkylene which may be substituted with 1 or 2 substituent groups, and OH, COOH, —CO—O-lower alkyl, halogen, CN, phenyl, —O-lower alkyl, —O—CO-lower alkyl, amino, mono- or di-lower alkylamino, —CO—$NH_2$, —CO-mono- or di-lower alkylamino and cycloalkyl can be exemplified as preferred substituent groups.

The "cycloalkyl" means a $C_{3-6}$ monocyclic saturated hydrocarbon ring group, and is preferably cyclopropyl, cyclobutyl, cyclopentyl or cyclohexyl.

The "cycloalkanediyl" means divalent group of a $C_{3-6}$ monocyclic saturated hydrocarbon ring, and is preferably cyclopropanediyl, cyclobutanediyl, cyclopentanediyl, cyclohexanediyl or the like, of which cyclopropanediyl is particularly desirable.

The "availability" means a property in which an orally administered agent is absorbed by digestive tract, exerts initial liver passage effect and then enters into blood.

A compound in which a hydroxyl group is replaced by a prodrug-forming group is also included in the compound of the invention.

Examples of the prodrug-forming group include the groups described in *Prog. Med.,* 5, 2157-2161 (1985) and "Iyakuhin no Kaihatsu (Development of Medicaments)" Vol. 7 (Hirokawa Shoten, 1990) Bunshi Sekkei (Molecular Design), pp. 163-198.

Tautomers are present in the compounds of the invention. For example as described in the following.

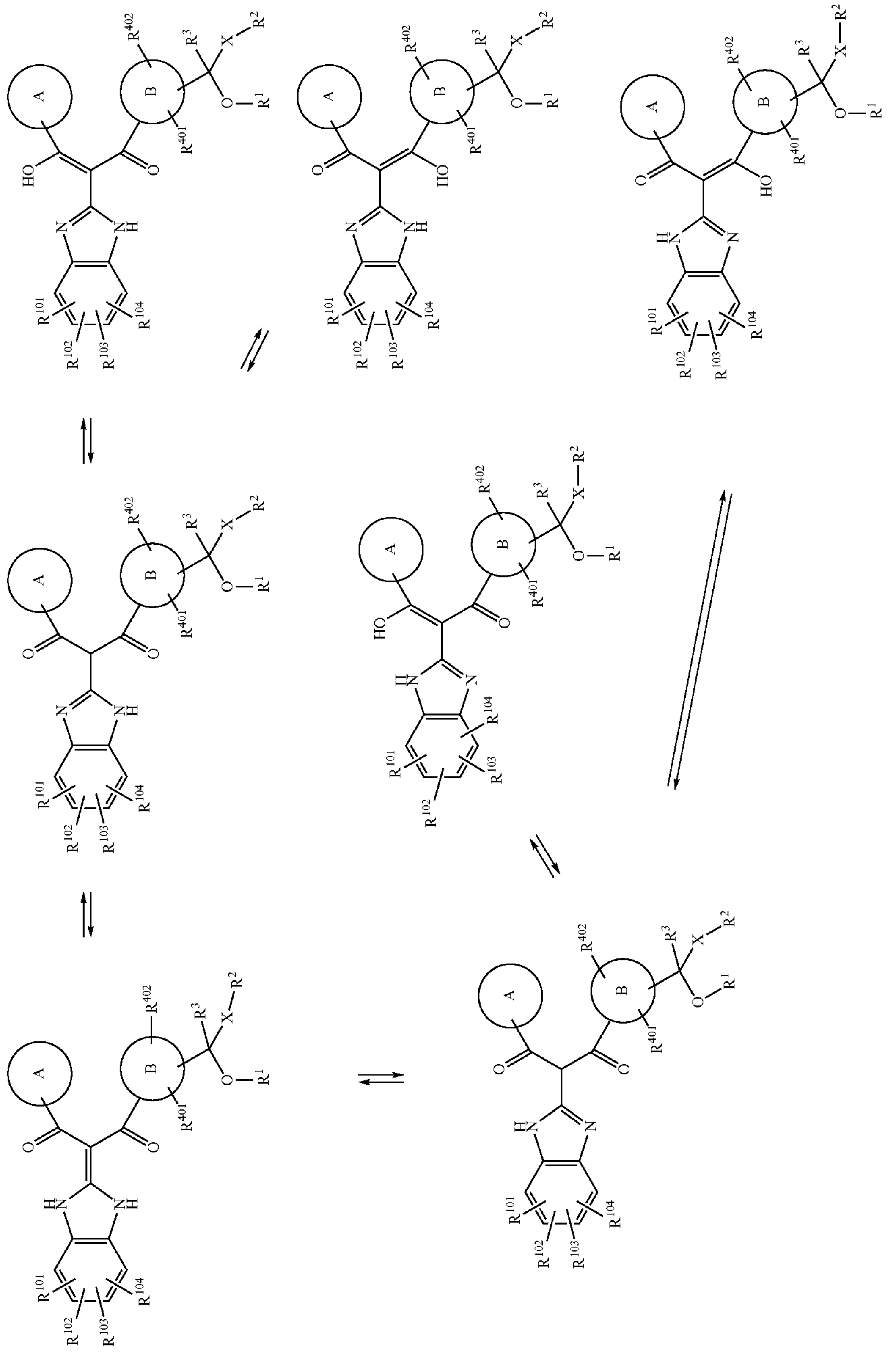

Separated forms of these isomers or mixtures thereof are also included in the invention. Also, the compounds of the invention may have an asymmetric atom or axial asymmetry depending on the kind of substituent group, so that isomers based on an asymmetric atom or the like can be present. Mixtures of these optical isomers and separated forms thereof are included in the invention, too. In addition, compounds in which the compounds of the invention are labeled with radioactive isotopes are also included in the invention.

Also, a compound in which geometrical isomerism regarding the 2-position double bond of propane as shown below can be mutually converted via tautomerism as shown in the above is present among the compounds of the invention. An example is shown below.

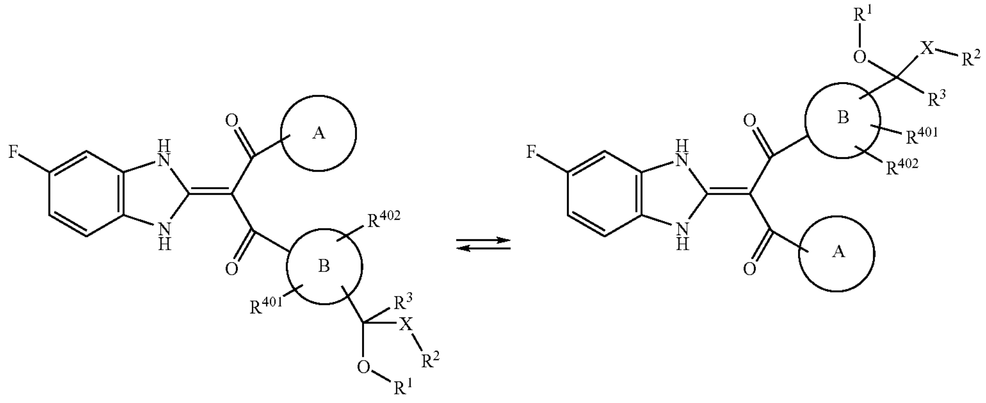

In addition, the compound of the invention sometimes forms acid addition salt or, depending on the kind of substituent group, salt with base, and such the salt is included in the invention, with the proviso that it is a pharmaceutically acceptable salt. Its illustrative example includes an acid addition salt with hydrochloric acid, hydrobromic acid, hydroiodic acid, sulfuric acid, nitric acid, phosphoric acid and the like inorganic acid or with formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, aspartic acid, glutamic acid and the like organic acid, a salt with sodium, potassium, magnesium, calcium, aluminum and the like inorganic base or with methylamine, ethylamine, ethanolamine, lysine, ornithine and the like organic base, ammonium salt and the like. Various hydrates and solvates, and substances having polymorphism, of the compound of the invention and a pharmaceutically acceptable salt thereof are also included in the invention.

(Production Methods)

The compound of the invention and a pharmaceutically acceptable salt thereof can be produced by employing various conventionally known synthesis methods, making use of the characteristics based on its basic nucleus or the kind of substituent groups.

In some cases, depending on the kind of functional group, it is effective in view of production techniques to replace said functional group with an appropriate protecting group (a group which is easily converted into said functional group) at a stage of from the materials to intermediates. Examples of such a functional group include amino group, hydroxyl group, carboxy group and the like, and the protecting groups described in "Protective Groups in Organic Synthesis (3rd Edition)" edited by Greene and Wuts (JOHN WILEY & SONS, 1991) and the like can be exemplified as their protecting groups which can be optionally selected in response to the reaction conditions. By such a method, a compound of interest can be obtained by carrying the reaction after introduction of said protecting group, and then removing the protecting group as occasion demands.

Typical production methods of the compound of the invention is described in the following. In this connection, the production methods of the invention are not limited to the examples illustrated in the following.

Abbreviations in the following sentences are as follows. DMF: N,N-dimethylformamide; DMSO: dimethyl sulfoxide; THF: tetrahydrofuran; Tol: toluene; DCE: 1,2-dichloroethane; TEA: triethylamine; Diglyme: diethylene glycol dimethyl ether; LiTMP: lithium 2,2,6,6-tetramethylpiperidate; LDA: lithium diisopropylamide; WSCHCl: 3-(3-dimethylaminopropyl)-1-ethyl carbodiimide hydrochloride; HOBt: 1-hydroxybenzotriazole; CDI: 1,1'-carbonyldiimidazole Production Methods First Production Method

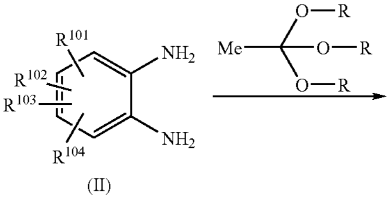

(II)

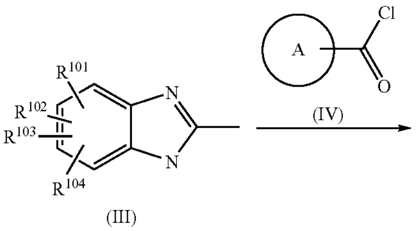

(IV)

(III)

-continued

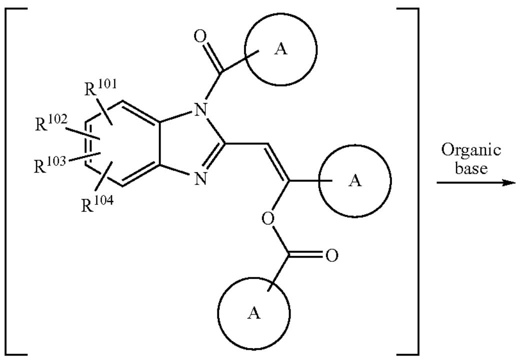

(V)

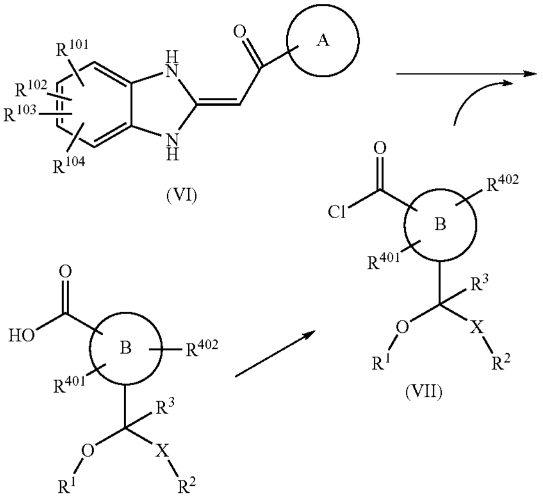

(VI)

(VII)

(VIIa)

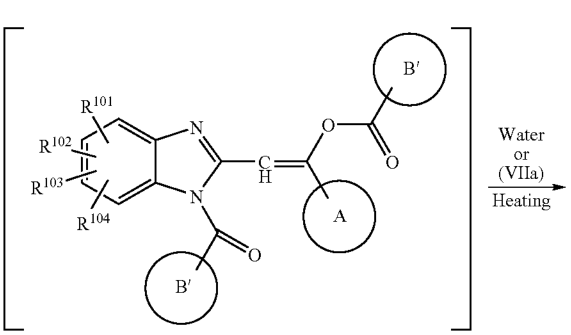

(VIIIa)

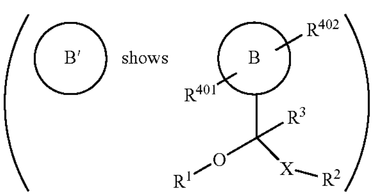

-continued

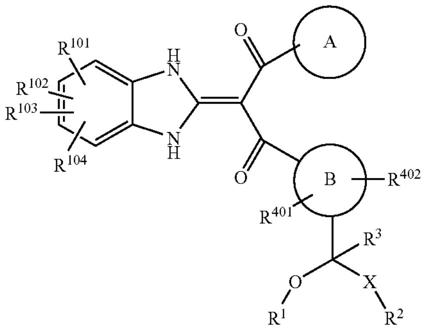

(I)

(Symbols in the reaction scheme are as follows.

R: lower alkyl, $R^{401}$, $R^{402}$, $R^{101}$, $R^{102}$, $R^{103}$ and $R^{104}$ may be optionally protected with a protecting group. The same shall apply hereinafter.)

This production method is a method for obtaining the compound (I) of the invention. By a method which is based on the production method 4 described in the Patent Reference 1, a 2-methylimidazole compound (III) is obtained from a 1,2-diaminobenzene compound (II), said compound (III) is allowed to react with an acyl compound (IV), the thus obtained reaction mixture is treated at room temperature to under heating in the presence of morpholine or the like organic base in a reaction-inert solvent, thereby obtaining an imidazole compound (VI). This acyl compound (IV) can be obtained illustratively by chlorinating a corresponding carboxylic acid compound with thionyl chloride, oxalic acid chloride or the like chlorination agent, in dichloromethane or the like solvent inert to the reaction at room temperature or under heating in the presence or absence of DMF or the like catalyst. Thionyl chloride or the like may be directly used as the solvent. The thus obtained reaction mixture can be purified by its azeotropic treatment with Tol or the like, and further purification may be carried out or not carried out. In addition, the intermediate (V) and the like may be isolate or not isolated.

Next, an inter mediate (VIIIa) and the like are obtained by allowing the imidazole compound (VI) and acyl compound (VII) to undergo acylation reaction in Diglyme or the like reaction inert solvent in the presence or absence of TEA or the like base at room temperature or to under heating, and then the compound (I) of the invention is obtained by adding a carboxylic acid (VIIa) in a reaction corresponding amount with said compound (VIIIa) or a reaction corresponding amount of water and heating the mixture. The acyl compound (VII) can be obtained by the same method for the preparation of compound (IV). In addition, the intermediates (VIIIa) and the like may be isolated or not isolated.

Second Production Method

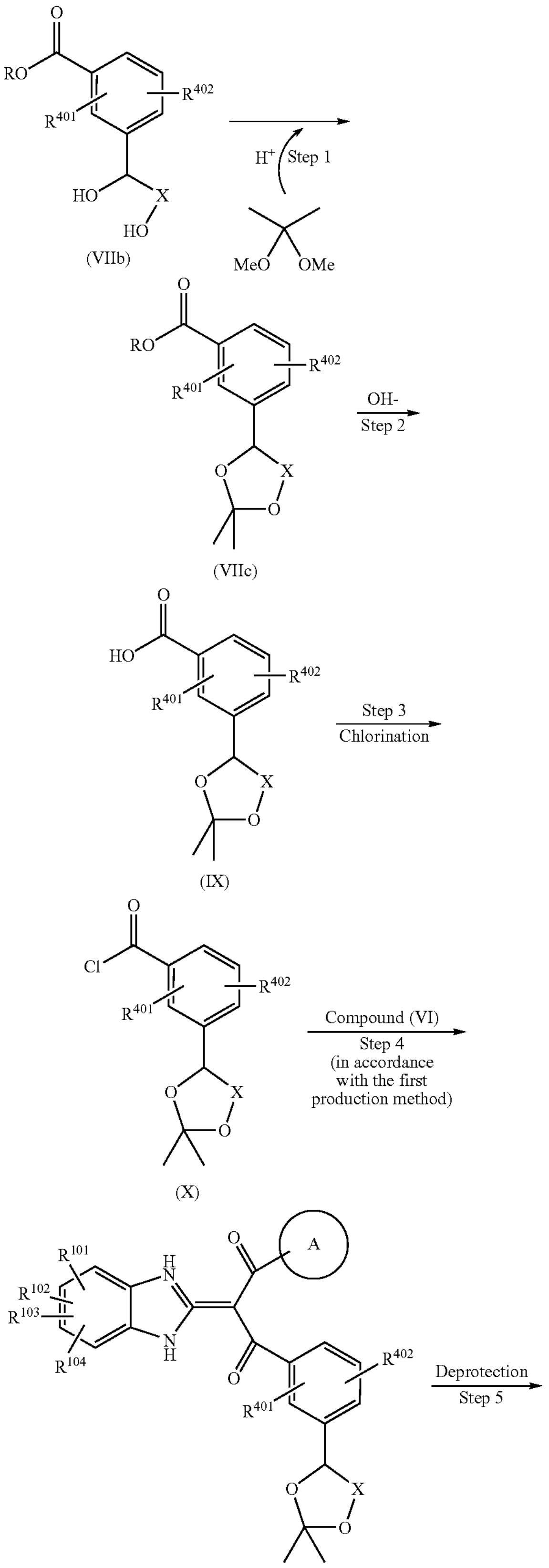

(VIIb)

(VIIc)

(IX)

(X)

(Ib-i)

-continued

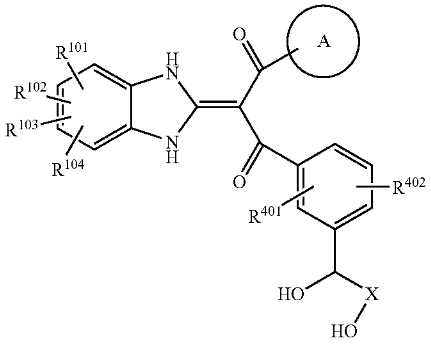

(Ia-i)

This production method is a method particularly suitable for obtaining the compounds (Ia) and (Ia-i) of the invention. By this production method, optically active compounds of the invention can be selectively produced by the use of optically active compounds (VIId) and (VIIe) as the material compounds.

Step 1: This step is a conventionally known method regarding protection of a 1,2- or 1,3-dihydroxy compound. The protecting groups described in “Protective Groups in Organic Synthesis (3rd Edition)” edited by Greene and Wuts (JOHN WILEY & SONS, 1991) and the like may be optionally selected and used in response to the reaction conditions.

In this connection, when optically active 1,2-dihydroxy compounds (VIId) and (VIIe) are used as the starting materials instead of the compound (VIIb), said compounds (VIId) and (VIIe) can be produced by the method shown in the following [ ].

(1): This step is a method conventionally known as a Stille coupling reaction (e.g., J. K. Stille et al., *J. Org. Chem.*, 52, 422-424, 1987). More illustratively, this is carried out by allowing a haloaryl compound or an aryl triflate compound, preferably a bromoaryl compound (XI) or an iodoaryl compound, to react with a reaction corresponding amount of tributyl(vinyl)tin or the like organic tin reagent, in Tol or the like reaction inert solvent at room temperature to under heating in the presence of tris(dibenzylideneacetone)dipalladium or the like palladium catalyst and tri-tert-butylphosphine or the like phosphine compound, also preferably in an atmosphere of argon.

(2) This step is a conventionally known method for asymmetrically dihydroxylating the olefin compound (XII). For example, this is carried out by the method described in a reference “Sharpless, K. B. et al., *Chem. Rev.*, 94, 1994, 2483-2547”, illustratively by carrying out oxidation of the olefin compound with AD-mix (Aldrich, USA) in a tert-butanol-water mixed solvent or the like reaction inert solvent. The reaction is carried out at a temperature of from ice-cooling to heating, preferably from 0° C. to room temperature. The optically active 1,2-dihydroxy compounds (VIId) and (VIIe) having desired absolute configuration can be respectively prepared by properly using AD-mix-alpha and AD-mix-beta. See a scheme of a chemical reaction below.

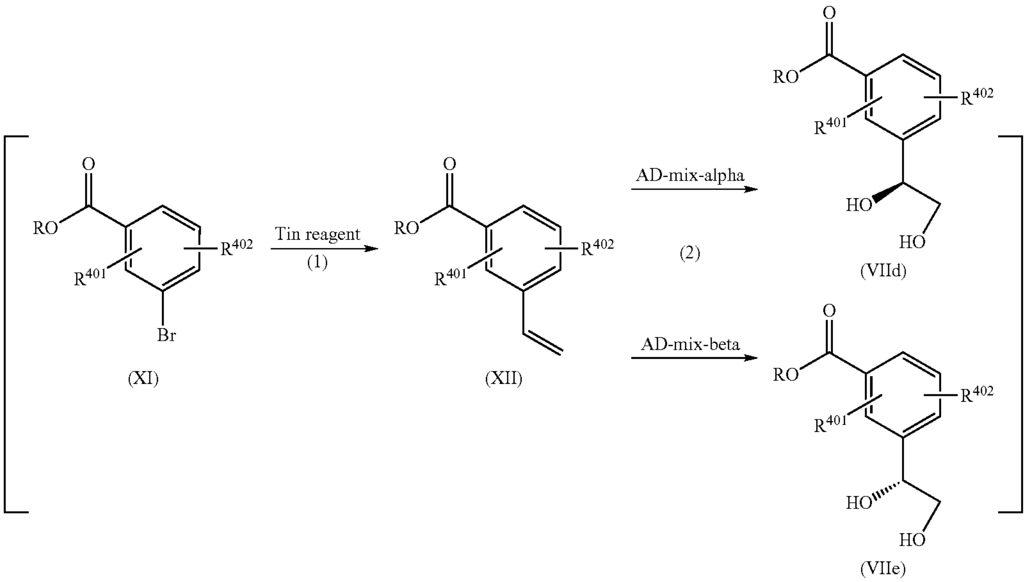

(XI) (XII) (VIId) (VIIe)

Step 2: This step is a conventionally known hydrolysis reaction, which is effected by carrying out the reaction in THF, methanol or the like reaction inert solvent in the presence of sodium hydroxide or the like inorganic base, preferably at room temperature.

Step 3: This step is carried out by a conventionally known method (K. G. Akamanchi et al., *Synlett,* 1999, 11, 1763-1785). Illustratively, an acid chloride forming reagent is prepared from thionyl chloride and 1H-benzotriazole in dichloromethane or the like reaction inert solvent, and the acyl compound (X) is obtained by allowing said reagent to react with a corresponding carboxylic acid compound (IX) dissolved in dichloromethane or the like reaction inert solvent under ice-cooling, at room temperature or under heating. The thus obtained compound (X) can be purified by its azeotropic treatment with Tol or the like, and further purification may be carried out or not carried out.

Step 4: This step is carried out in accordance with the first production method.

Step 5: This step is a method for obtaining the dihydroxy compound (Ia-i) by carrying out a conventionally known deprotection reaction on an acetonide-protected compound (Ib-i) of 1,2- or 1,3-dihydroxy compound. This method can be carried out under the reaction conditions and the like described in "Protective Groups in Organic Synthesis (3rd Edition)" edited by Greene and Wuts (JOHN WILEY & SONS, 1991).

In addition, when vinyl group of the olefin compound (XII) is positioned at the ortho position of fluorine atom like the case of 3-vinyl-2-fluorobenzoic acid ethyl ester, or positioned at the ortho position of a substituent group having chelation ability, the vinyl group of said compound can also be introduced via an aryl metal compound. In an example, it can also be synthesized by preparing an aryl metal compound through the treatment of 2-fluorobenzoic acid ethyl ester with LiTMP, LDA or the like organic metal base in THF or the like reaction inert solvent under a low temperature, preferably at −78° C., subsequently obtaining 3-formyl-2-fluorobenzoic acid ethyl ester by allowing said compound to react with a compound to be used as a DMF or the like formyl group source under a low temperature, preferably at −78° C., and then converting the formyl group into vinyl group by the conventionally known Wittig reaction. More illustratively, the Wittig reaction is carried out by allowing an aldehyde compound and its reaction corresponding amount of a phosphonium salt reagent to undergo the reaction in THF or the like reaction inert solvent in the presence of sodium hydride, alkyl lithium, potassium t-butoxide or the like base, preferably at a temperature of from ice-cooling to room temperature and also preferably in an atmosphere of argon.

Third Production Method

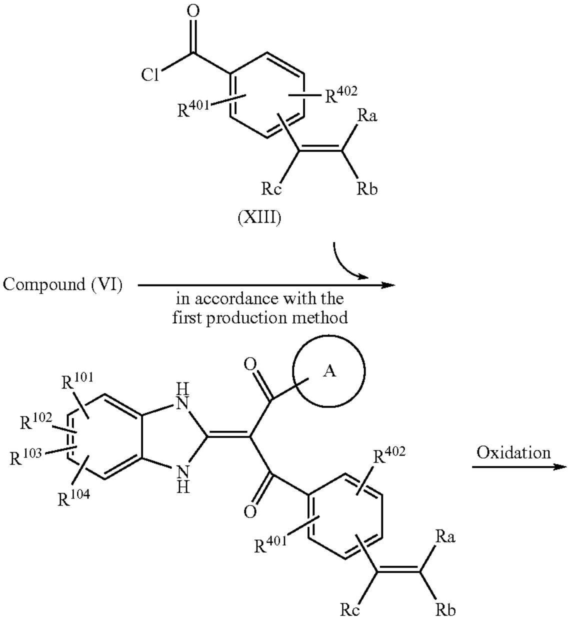

(XIII) (XIV)

-continued

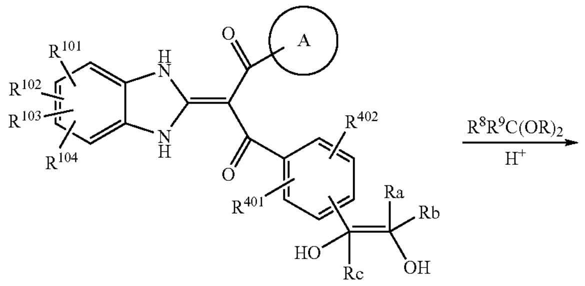

(Ia-ii)

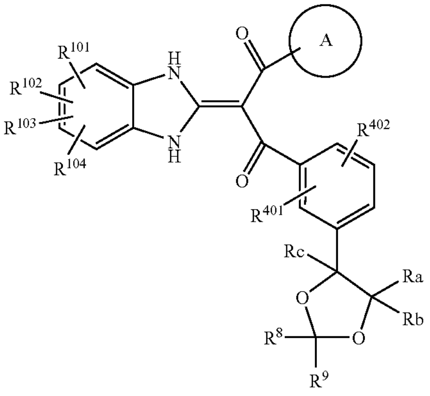

(Ib-ii)

(In the reaction scheme, Ra and Rb may be the same or different from each other and each represents H or lower alkyl, $CH_2NMe_2$, $CH_2OMe$, CN, Ph, $CO_2Et$, $CF_3$ or cycloalkyl, or Ra and Rb may together form cycloalkyl, and Rc represents H or lower alkyl. The same shall apply hereinafter.)

An imidazole compound (XIV) obtained from the compound (VI) prepared in the first production method and an acyl compound (XIII), in accordance with the first production method, can be converted into a compound (Ia-ii) by a conventionally known method for dihydroxylating an olefin compound (edited by J. March, "ADVANCED ORGANIC CHEMISTRY" (JOHN WILEY & SONS, 1992). More preferably, this reaction is carried out by oxidizing the an olefin compound with osmium tetroxide in THF-water or the like reaction inert solvent in the presence of N-methylmorpholine-N-oxide or the like co-oxidizing agent. The reaction is carried out at a temperature of from ice-cooling to heating, preferably at room temperature.

The compound (Ia-ii) as a 1,2-dihydroxy compound can be converted into a ketal compound (Ib-ii) or an ortho ester compound by a conventionally known method using a ketone equivalent compound or an ortho ester compound. These can be regarded as protecting reaction of the 1,2-dihydroxy compound, and van be carried out using the reaction conditions and the like described in the aforementioned "Protective Groups in Organic Synthesis (3rd Edition)".

Fourth Production Method

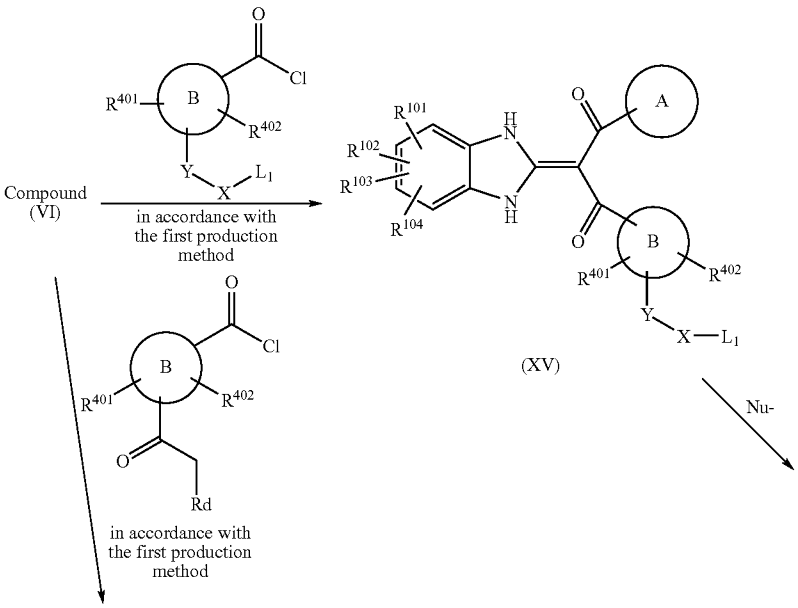

-continued

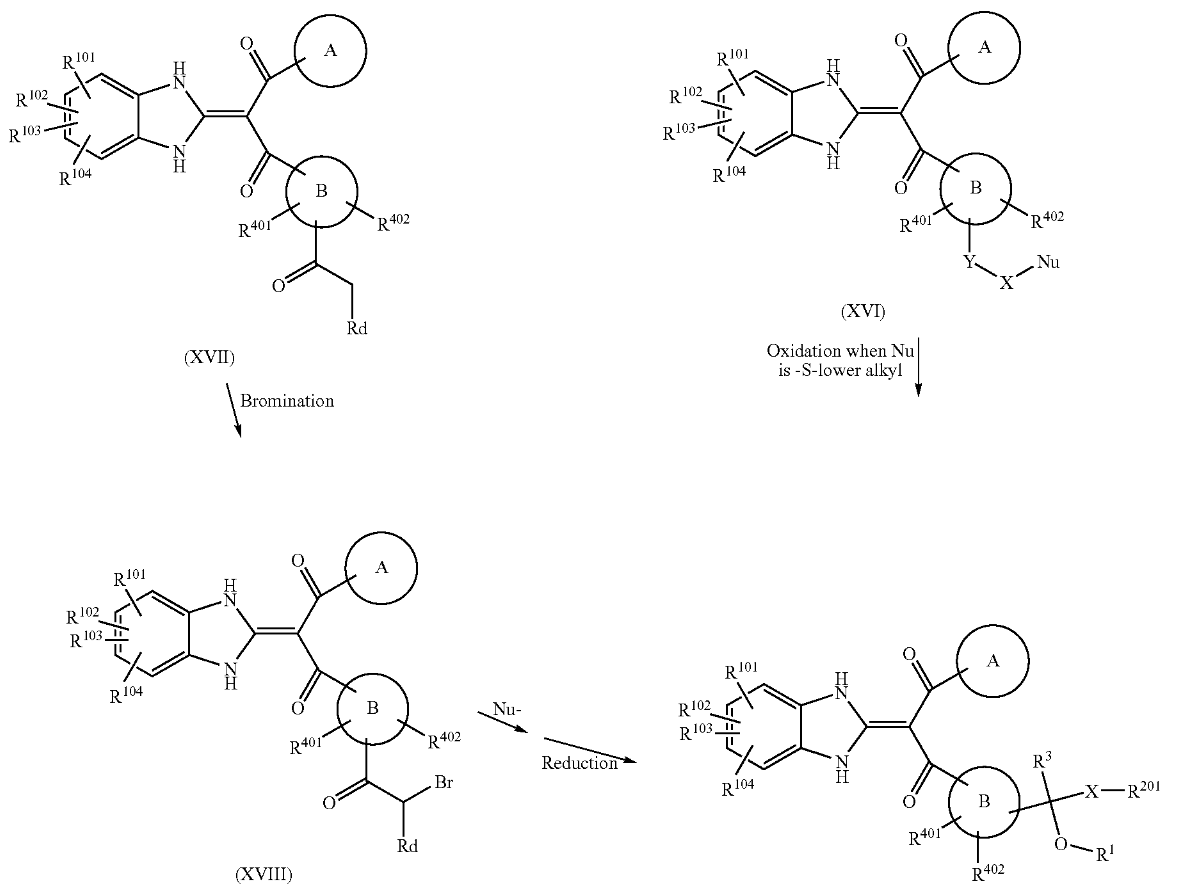

(XVII)

(XVI)

(XVIII)

(I-i)

(Symbols in the reaction scheme are as follows.

$L_1$: halogen or the like leaving group,

Nu: nucleophilic reagent

Y: ketone or —C($R^3$)($OR^1$)—,

Rd: substituent group on the lower alkylene corresponding to X in the general formula (I), and $R^{201}$: —S(O)m-lower alkyl, —$N_3$, N($R^6$)$R^7$, —OCO-lower alkyl or halogen. The same shall apply hereinafter.)

This production method is a method for producing a compound having the aforementioned group represented by $R^{201}$ as the $R^2$ among the compounds (I) of the invention.

This production method is carried out by allowing a compound (XV) having a leaving group $L_1$, converted from the compound (VI) in accordance with the first production method, and its reaction corresponding amount of a nucleophilic reagent to undergo an $S_N2$ type substitution reaction in THF, acetone, DMF, acetonitrile, dichloromethane, methanol, DMSO or the like reaction inert solvent, in the presence of potassium carbonate or the like inorganic base or TEA or the like organic base as occasion demands, and under cooling, from room temperature to heating or under reflux. As the nucleophilic reagent, potassium acetate, sodium azide, sodium thiomethoxide and the like anionic compounds, or amine compounds and the like basic compounds, chloride ions and the like can be exemplified.

When Y in the compound (XV) is ketone, a ketone compound (XVII) converted from the compound (VI) in accordance with the first production method is allowed to react with bromine or hydrogen bromide in acetic acid or the like reaction inert solvent to convert it into an α-bromoketone compound (XVIII), and the aforementioned $S_N2$ type substitution reaction can be carried out on this compound (XVIII). The thus obtained substituted compound can be converted into (I-i) by reducing the ketone by the reduction reaction shown below.

When the nucleophilic reagent is an S-lower alkyl group, thioalkyl group of the obtained compound can be oxidized into a sulfoxide compound or sulfone compound using an oxidizing agent in accordance with the 10th production method of Patent Reference 1. As the oxidizing agent, m-chloroperbenzoic acid or hydrogen peroxide is more preferably used.

Fifth Production Method

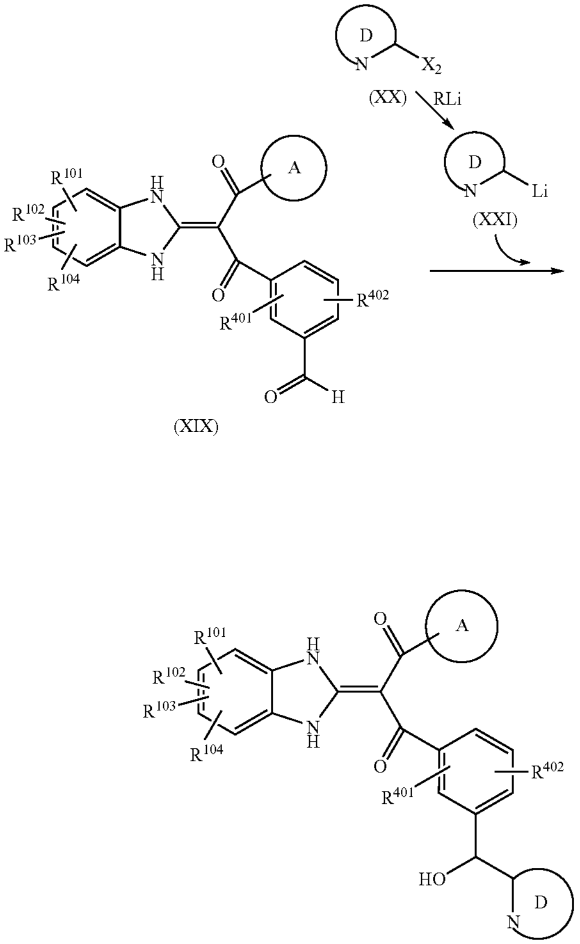

(I-ii)

(In the reaction scheme, $X_2$ represents halogen, and the ring D means pyridine or imidazole which may be substituted.)

This production method is a method in which a hydroxy compound (1-ii) is obtained by allowing a reaction corresponding amount of an aldehyde compound (XIX) to react with an organic lithium compound (XXI) prepared from a nitrogen-containing haloaryl compound (XX) using n-butyl lithium or the like organic base, in THF or the like reaction inert solvent at a temperature of from −78° C. to room temperature.

Sixth Production Method

This production method is carried out by subjecting a dithioacetal compound (XXII) and a diamine compound (XXIII) to a condensation reaction in BtOH or the like reaction inert solvent at room temperature to under heating, preferably heating under reflux.

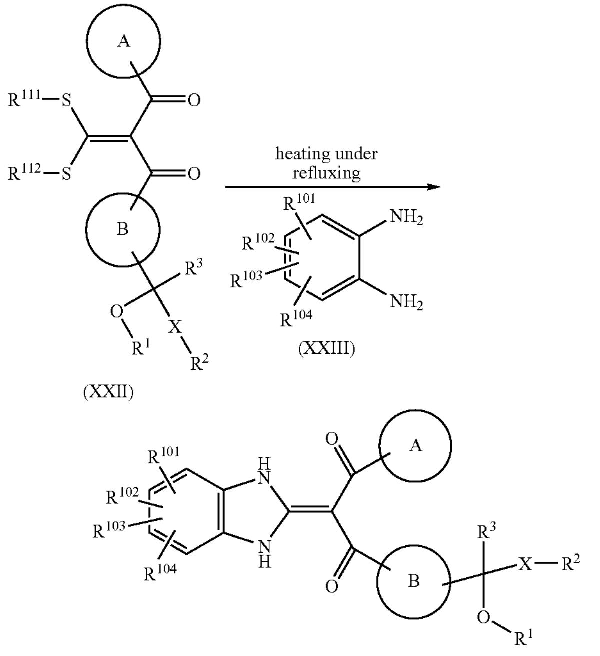

(I)

(In the reaction scheme, $R^{111}$ and $R^{112}$ represent lower alkyl, or $R^{111}$ and $R^{112}$ may together form a ring, and the substituent group on the ring B may be protected with an appropriate protecting group.)

In addition, the compounds of the invention and pharmaceutically acceptable salts thereof can be produced by employing the following conventionally known substituent group conversion methods making use of the characteristics based on the kinds of the substituent group.

1. Reduction Reaction

Reduction of ketone into hydroxyl group, reduction of azido group into amino group, reduction of unsaturated alkyl group into saturated alkyl group and the like reactions can be carried out in accordance with the 4th production method of Patent Reference 1. Examples of more desirable methods include a method in which sodium borohydride, lithium borohydride, diisobutylaluminum hydride, lithium aluminium hydride or the like reducing agent is used, and a method in which catalytic reduction is carried out using palladium (Pd), platinum (Pt), nickel (Ni) or the like in an atmosphere of hydrogen or ammonium formate or the like hydrogen donor.

2. Acylation Reaction of Hydroxyl Group or Amino Group

Acylation reaction of hydroxyl group or amino group is carried out by allowing a hydroxy compound or an amine compound to react with a reaction corresponding amount of an acid chloride compound or an acid anhydride in dichloromethane, DCE, pyridine, THF, Tol or the like reaction inert solvent in the presence or absence of dimethylaminopyridine or the like at room temperature or under heating. Alternatively, it can also be carried out by allowing a hydroxy compound and its reaction corresponding amount of a carboxylic acid compound to undergo the reaction in DMF or the like reaction inert solvent in the presence or absence of WSCHCl, HOBt, CDI or the like condensing agent, dimethylaminopyridine or the like reaction accelerator and TEA or the like organic base, at room temperature or under heating. When two or more hydroxyl groups are present, the reaction can also be carried out selectively at a desired position by optionally using a protecting group. Dihydroxy compound can also be converted into a cyclic carbonic acid compound (cyclic carbonate compound) by the use of CDI or the like. In the case of a compound having two or more hydroxyl groups and amino groups, all of them may be acylated or a part thereof may be acylated.

3. Hydrolysis Reaction

The reaction for hydrolyzing an ester compound into a hydroxy compound and a carboxylic acid compound can be carried out in accordance with the 8th production method of Patent Reference 1. As a more preferred method, this is carried out in THF using sodium hydroxide, potassium hydroxide or the like base.

4. Conversion of a 1,2-Dihydroxy Compound into an Aldehyde Compound

The reaction for converting a 1,2-dihydroxy compound into an aldehyde compound is carried out by effecting oxidative cleavage of 1,2-dihydroxyethyl group in THF, water, methanol or the like reaction inert solvent using periodic acid or a salt thereof, lead tetracetate or the like oxidizing agent. The thus obtained aldehyde compound can be converted into an amine compound in dichloromethane or the like reaction inert solvent in accordance with the 5th production method of Patent Reference 1.

The compounds of the invention are isolated and purified as free compounds, pharmaceutically acceptable salts thereof, hydrates, solvates or polymorphic substances. The pharmaceutically acceptable salt of the compound (I) of the invention can also be produced by subjecting it to a usually used salt formation reaction.

Isolation and purification are carried out by employing usual chemical operations such as extraction, fractional crystallization, various types of fractionation chromatography and the like.

Various isomers can be separated by selecting appropriate material compounds or making use of differences in physicochemical properties among isomers. For example, an optical isomer can be converted into a stereochemically pure isomer by selecting an appropriate material or by a method for separating racemic compounds (e.g., a method in which they are converted into diastereomer salts with a general optically active base or acid and then subjected to optical resolution, or a method in which they are fractionated using a chiral column or the like).

In addition to the compounds of the Examples which are described later, compounds of the following tables can be obtained in the same manner as in the production methods of the invention.

In this connection, abbreviations in the specification are as follows.

FA: FAB-MS $(M+H)^+$; FN: FAB-MS $(M-H)^-$; FAB-MS is a measured value by fast atom bombardment ionization mass spectrometry; ES+ is ESI+; ES− is ESI−; EI: EI-MS; EI-MS is a measured value by atom bombardment ionization mass spectrometry; N1: characteristic peak δ ppm of NMR (DMSO-$d_6$, TMS internal standard); N2: characteristic peak δ ppm of NMR ($CDCl_3$, TMS internal standard); brs: broad singlet; mp: melting point; (round bracket) shows a solvent for recrystallization, EA-His ethyl acetate, EA-ET-His ethyl acetate-ether-hexane, and EtOH is ethanol for recrystallization; $[\alpha]_D$: angle of rotation at 25° C. (c: concentration (g solute/100 $cm^3$) MeOH: measuring solvent); CN or NC: cyano; vin: vinyl; Ph: phenyl; Me: methyl; diMe: dimethyl; Et: ethyl; iPr: isopropyl; cPr: cyclopropyl; cBu: cyclobutyl; nBu: butyl; cHex: cyclohexyl; Ac: acetyl; diCl: dichloro; diF: difluoro; triF: trifluoro; diOH: dihydroxy; Py: pyridyl; Py3: pyridin-3-yl; Py4: pyridin-4-yl; Py5: pyridin-5-yl; dixr4: dioxolan-4-yl; Thiop: thiophene; Thiop2: thiophen-2-yl; Thiop3: thiophen-3-yl; pheny: phenylene; yl:yl; diyl:diyl; oxal: oxalate; Rex: Reference Example; Rex No.: Reference Example No.; Ex: Example; Ex No.: Example No.; DATA: physicochemical properties

TABLE 1

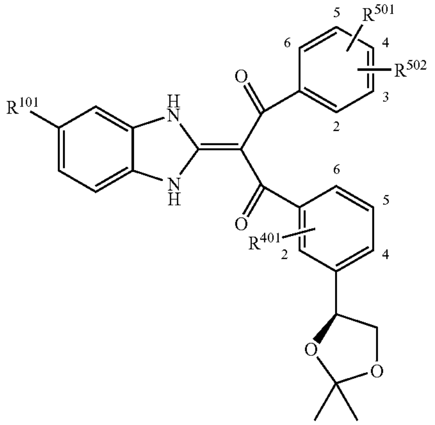

| No. | $R^{101}$ | $R^{401}$ | $R^{501}$ | $R^{502}$ |
|---|---|---|---|---|
| P-1 | H | H | 3-F | H |
| P-2 | H | 2-F | 3-F | H |
| P-3 | H | 2-F | 3-CN | H |
| P-4 | H | 2-F | 2-Me | H |
| P-5 | H | 2-F | 3-Me | H |
| P-6 | H | 2-F | 2-Cl | H |
| P-7 | H | 2-F | 2-F | H |
| P-8 | H | 2-F | H | H |
| P-9 | H | 2-F | 3-Cl | H |
| P-10 | H | H | 3-F | H |
| P-11 | H | 4-F | 3-F | H |
| P-12 | H | 2-Me | 3-F | H |
| P-13 | F | 2-F | 3-F | H |
| P-14 | H | 2-F | 3-MeO | H |
| P-15 | H | 4-F | 3-F | 5-F |
| P-16 | H | 4-F | 2-Cl | H |

TABLE 2

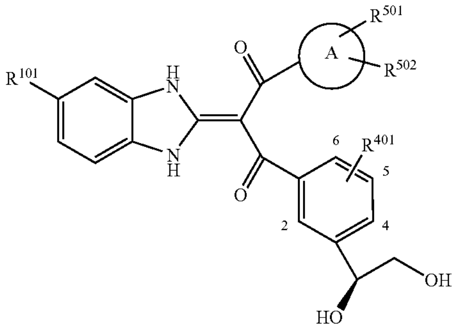

| No. | $R^{101}$ | $R^{401}$ | $R^{501}$ | $R^{502}$ | ring A |
|---|---|---|---|---|---|
| P-17 | H | 2-nBu | 3-F | H | Ph |
| P-18 | H | 4-F | H | H | Ph |
| P-19 | H | 2-MeO | 3-F | H | Ph |
| P-20 | H | 2-Cl | 3-F | H | Ph |
| P-21 | H | 2-Me | 3-F | 5-F | Ph |
| P-22 | H | 2-Me | 3-Cl | H | Ph |

TABLE 2-continued

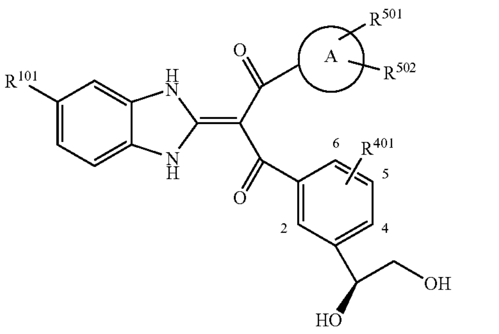

| No. | $R^{101}$ | $R^{401}$ | $R^{501}$ | $R^{502}$ | ring A |
|---|---|---|---|---|---|
| P-23 | H | 2-Me | 2-Cl | H | Ph |
| P-24 | H | 2-Me | 3-Me | H | Ph |
| P-25 | H | 2-Me | H | H | Ph |
| P-26 | H | 2-Me | 2-F | H | Ph |
| P-27 | H | 2-Cl | 3-F | 5-F | Ph |
| P-28 | H | 2-Cl | 3-Cl | H | Ph |
| P-29 | $Py3CH_2O$ | 2-F | 3-F | 5-F | Ph |
| P-30 | H | 4-F | 4-Cl | H | Ph |
| P-31 | H | 2-Cl | 3-F | 5-F | Ph |
| P-32 | H | 2-F | 3-F | 5-F | Ph |
| P-33 | H | 2-F | H | H | Py3 |
| P-34 | H | 2-Cl | 2-Cl | H | Ph |
| P-35 | H | 2-Cl | H | H | Ph |
| P-36 | H | 2-Cl | 2-F | H | Ph |
| P-37 | H | 2-Cl | 3-CN | H | Ph |
| P-38 | H | 4-F | H | H | Ph |
| P-39 | H | 4-F | 3-Me | H | Ph |
| P-40 | H | 4-F | 3-Br | H | Ph |

TABLE 3

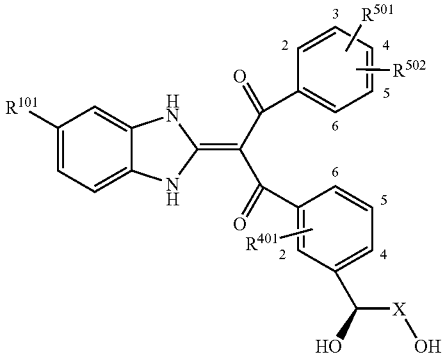

| No. | $R^{101}$ | $R^{401}$ | $R^{501}$ | $R^{502}$ | X |
|---|---|---|---|---|---|
| P-41 | H | H | 3-F | H | $—CH_2—$ |
| P-42 | H | H | 3-F | 5-F | $—(CH_2)_2—$ |
| P-43 | H | 4-F | 3-F | H | $—CH_2—$ |
| P-44 | H | 2-F | 3-F | H | $—CH_2—$ |
| P-45 | H | 2-Me | 3-F | 5-F | $—CH_2—$ |
| P-46 | H | H | 3-F | H | $—CH_2—$ |
| P-47 | H | 2-F | H | H | $—CH_2—$ |
| P-48 | H | 2-nBu | 3-F | H | $—CH_2—$ |
| P-49 | H | 2-F | 3-Cl | H | $—CH_2—$ |
| P-50 | F | 2-F | 3-F | H | $—CH_2—$ |
| P-51 | H | 2-F | 3-CN | H | $—CH_2—$ |
| P-52 | $Py3CH_2O$ | 2-F | 3-MeO | H | $—CH_2—$ |

TABLE 4

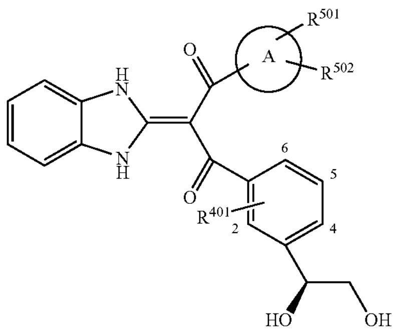

| No. | $R^{401}$ | $R^{501}$ | $R^{502}$ | ring A |
|---|---|---|---|---|
| P-53 | 2-Me | 2-Cl | H | Ph |
| P-54 | 2-F | 3-Me | H | Ph |
| P-55 | 2-Cl | 3-Cl | H | Ph |
| P-56 | 2-F | 2-Me | H | Ph |
| P-57 | 4-F | 2-Cl | H | Ph |
| P-58 | 4-F | 3-Cl | H | Ph |
| P-59 | 2-MeO | 3-F | H | Ph |
| P-60 | 2-Me | 3-F | H | Ph |
| P-61 | 2-Cl | 3-F | H | Ph |
| P-62 | 4-F | 3-F | 5-F | Ph |
| P-63 | 2-Me | 3-Cl | H | Ph |
| P-64 | 2-F | 2-Cl | H | Ph |
| P-65 | 2-Me | 3-Me | H | Ph |
| P-66 | 2-F | 3-MeO | H | Ph |
| P-67 | 2-Me | H | H | Ph |
| P-68 | 2-F | 2-F | H | Ph |
| P-69 | 2-Me | 2-F | H | Ph |
| P-70 | 2-Cl | 3-F | 5-F | Ph |
| P-71 | 4-F | 4-Cl | H | Ph |
| P-72 | 2-Cl | 3-Me | H | Ph |
| P-73 | 2-F | 3-F | 5-F | Ph |
| P-74 | 2-F | H | H | Py3 |
| P-75 | 2-Cl | 4-Cl | H | Ph |
| P-76 | 2-Cl | H | H | Ph |
| P-77 | 2-Cl | 2-F | H | Ph |
| P-78 | 2-Cl | 3-CN | H | Ph |
| P-79 | 2-Cl | H | H | Ph |
| P-80 | 4-F | 3-Me | H | Ph |
| P-81 | 4-F | 3-Br | H | Ph |

The active ingredient of the invention and the compound of the invention or a pharmaceutically acceptable salt thereof can be used alone as a medicament, but it can be generally prepared from one or two or more of active ingredients using pharmaceutical carriers, fillers and the like materials generally used in said field by a generally used method. Its administration may be in the form of either oral administration by tablets, pills, capsules, granules, powders, solutions and the like, or parenteral administration by intraarticular, intravenous, intramuscular and the like injections, suppositories, eye drops, eye ointments, percutaneous solutions, ointments, percutaneous adhesive preparations, transmucosal solutions, transmucosal adhesive preparations, inhalations and the like.

The solid composition for use in the oral administration according to the present invention is used in the form of tablets, powders, granules and the like. In such a solid composition, one or more active ingredients are mixed with at least one inert diluent such as lactose, mannitol, glucose, hydroxypropylcellulose, microcrystalline cellulose, starch, polyvinyl pyrrolidone and/or aluminum magnesium silicate. In the usual way, the composition may contain other additives than the inert diluent, such as magnesium stearate or the like lubricant, calcium cellulose glycolate or the like disintegrating agent, a stabilizing agent and a solubilization assisting agent. As occasion demands, tablets or pills may be coated with a sugar coating or a film of a gastric or enteric substance such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethanol. In addition to the inert diluent, said composition may also contain a solubilizing agent, a moistening agent, a suspending agent and the like auxiliary agents, as well as sweeteners, flavors, aromatics and antiseptics.

The injections for parenteral administration includes aseptic aqueous or non-aqueous solutions, suspensions and emulsions. Examples of the diluent for use in the aqueous solutions and suspensions include distilled water for injection and physiological saline. Examples of the diluent for use in the non-aqueous solutions and suspensions include propylene glycol, polyethylene glycol, olive oil or the like plant oil, ethanol or the like alcohol, polysorbate 80 (trade name) and the like. Such a composition may further contain a tonicity agent, an antiseptic, a moistening agent, an emulsifying agent, a dispersing agent, a stabilizing agent or a solubilization assisting agent. These are sterilized for example by filtration through a bacteria retaining filter, blending of a germicide or irradiation. Alternatively, they may be used by firstly making into sterile solid compositions and dissolving them in sterile water or a sterile solvent for injection use prior to their use.

Transmucosal preparations such as transnasal preparations are used in the form of solid, liquid or semi-solid state and can be produced in accordance with a conventionally known method. For example, conventionally known pH adjusting agents, antiseptics, thickeners, and fillers are optionally added and formed into a solid, liquid or semi-solid state. The transnasal preparations are administered using a usual sprayer, nasal drop container, tube, nasal cavity insertion tool or the like.

In the case of oral administration, proper dose per day is generally from about 0.001 to 100 mg/kg, preferably from 0.1 to 30 mg/kg, more preferably from 0.1 to 10 mg/kg, and this is administered in one portion or dividing into two to four doses. In the case of intravenous administration, suitable dose per day is approximately from 0.0001 to 10 mg/kg body weight, and this is administered once a day or dividing it into two or more doses. In addition, transmucosal preparations are administered at a dose of approximately from 0.001 to 100 mg/kg body weight, once a day or by dividing it into two or more doses. The dose is optionally decided in response to each case by taking symptoms, age, sex and the like into consideration.

EXAMPLES

The following describes the invention further in detail based on Examples. The compounds of the invention are not limited to the compounds described in the following examples. Also, production methods of the material compounds are shown in Reference Examples.

The compound of Reference Example 1-1 is a known compound.

Reference Example 1-2

A 4.0 g portion of 2-methyl-1H-benzimidazole and 13.9 ml of TEA were dissolved in 40 ml of Diglyme, and 17.5 g of 2-chlorobenzoic acid chloride was added dropwise thereto. The reaction mixture was stirred at 100° C. for 3 hours. After cooling to room temperature, the reaction mixture was mixed with water, extracted with chloroform, dried with anhydrous sodium sulfate and then concentrated, thereby obtaining an orange oily substance. This was dissolved in 60 ml of methanol, mixed with 7.9 ml of morpholine and then heated under reflux for 3.5 hours. The reaction mixture was cooled to room temperature, mixed with water and then stirred for 1 hour. The thus formed precipitate was collected by filtration, washed with cool water and then dried to obtain 6.1 g (75%) of 1-(2-chlorophenyl)-2-(1,3-dihydro-2H-benzimidazol-2-ylidene)ethanone (Reference Example 1-2) as pale yellow powdery crystals. ES+: 271

The compounds shown in Table 5 and Table 6 were produced in the same manner.

TABLE 5

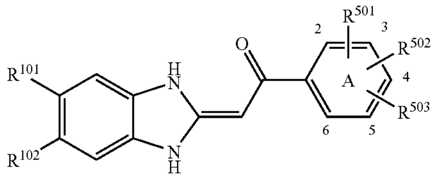

| Rex No. | $R^{101}$ | $R^{102}$ | $R^{501}$ | $R^{502}$ | $R^{503}$ | DATA |
|---|---|---|---|---|---|---|
| 1-1 | H | H | 3-F | 5-F | H | — |
| 1-2 | H | H | 2-Cl | H | H | ES+: 271 |
| 1-3 | H | H | 2-F | H | H | FA: 255 |
| 1-4 | H | H | 2-Me | H | H | ES+: 251 |
| 1-5 | H | H | 3-F | H | H | FA: 255 |
| 1-6 | H | H | 3-CN | H | H | ES+: 262 |
| 1-7 | H | H | 3-MeO | H | H | ES+: 567 |
| 1-8 | H | H | 3-Me | H | H | ES+: 251 |
| 1-9 | H | H | 3-Cl | H | H | ES+: 271, 273 |
| 1-10 | H | H | 3-MeOCO | H | H | N1: 3.91 (3H, s), 6.08 (1H, s) |
| 1-11 | H | H | 3-vinyl | H | H | FA: 263 |
| 1-12 | H | H | 4-F | H | H | ES+: 255 |
| 1-13 | H | H | 4-Cl | H | H | ES+: 271, 273 |
| 1-14 | H | H | 4-Me | H | H | ES+: 251 |
| 1-15 | H | H | 4-CN | H | H | FA: 262 |
| 1-16 | H | H | 3-$CF_3$ | 4-F | H | ES+: 323 |
| 1-17 | H | H | 3-F | 4-Cl | H | ES+: 289 |
| 1-18 | H | H | 2-Me | 3-F | H | ES+: 269 |
| 1-19 | H | H | 2-MeO | 5-F | H | ES+: 285 |
| 1-20 | H | H | 3-Me | 4-F | H | FA: 269 |
| 1-21 | H | H | 2-Me | 5-Cl | H | FA: 285 |
| 1-22 | H | H | 2-Me | 3-Me | H | ES+: 265 |
| 1-23 | H | H | 3-Me | 5-Me | H | FA: 263 |
| 1-24 | H | H | 3-F | 5-Br | H | FA: 335:333(1:1) |
| 1-25 | H | H | 3-F | 5-Cl | H | FA: 289 |
| 1-26 | H | H | 3-Cl | 4-F | H | FA: 289 |
| 1-27 | H | H | 2-Cl | 5-F | H | not purified |
| 1-28 | H | H | 3-Br | 4-F | H | FA: 335:333(1:1) |
| 1-29 | H | H | 3-Cl | 4-Cl | H | not purified |
| 1-30 | H | H | 2-F | 3-F | H | FA: 273 |
| 1-31 | H | H | 2-F | 6-F | H | ES+: 273 |
| 1-32 | H | H | 3-F | 4-F | H | FA: 273 |
| 1-33 | H | H | 3-Cl | 5-Cl | H | FA: 305 |
| 1-34 | H | H | 3-F | 5-$CF_3$ | H | FA: 323 |
| 1-35 | H | H | 2-F | 3-F | 5-F | not purified |
| 1-36 | H | H | 3-F | 4-F | 5-F | FA: 291 |
| 1-37 | F | H | 3-F | 5-Cl | H | ES+: 307 |
| 1-38 | F | H | 3-F | H | H | FA: 273 |
| 1-39 | F | H | 3-F | 5-F | H | FA: 291 |
| 1-40 | F | F | 3-F | 5-Cl | H | ES+: 325 |
| 1-41 | F | F | 3-F | 5-F | H | ES+: 309 |
| 1-42 | F | H | 3-F | 5-F | H | ES+: 307 |
| 1-43 | F | Cl | 3-F | 5-Cl | H | ES+: 341 |

TABLE 5-continued

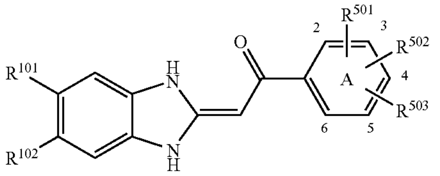

| Rex No. | $R^{101}$ | $R^{102}$ | $R^{501}$ | $R^{502}$ | $R^{503}$ | DATA |
|---|---|---|---|---|---|---|
| 1-44 | F | Cl | 3-F | 5-F | H | ES+: 325 |
| 1-50 | H | H | 3-Br | H | H | FA: 316:314(1:1) |

TABLE 6

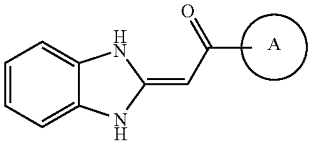

| Rex No. | ring A | DATA |
|---|---|---|
| 1-45 | 2-$CF_3$-Py5 | ES+: 306 |
| 1-46 | Thiop2 | ES+: 243 |
| 1-47 | 2-F-Py4 | ES+: 256 |
| 1-48 | 2,6-diCl-Py4 | FA: 306 |
| 1-49 | Thiop3 | ES+: 243 |

Reference Example 2-1

A 3.8 g portion of oxalic acid chloride was gradually added dropwise to 30 ml of methylene chloride solution containing 1.54 g of 3-vinylbenzoic acid and a catalytically effective amount of DMF and stirred at room temperature for about 2 hours, and then an appropriate amount of Tol was poured into the mixture and evaporation was carried out under a reduced pressure, thereby preparing 3-vinylbenzoic acid chloride. This was dissolved in a small amount of Diglyme and gradually added dropwise to 5 ml of Diglyme solution containing 0.82 g of 1-(3,5-difluorophenyl)-2-(1,3-dihydro-2H-benzimidazol-2-ylidene)ethanone which had been separately prepare in advance and 1.4 ml of TEA, under heating at 70° C. After completion of the dropwise addition, this was risen to 100° C. and heated for about 25 minutes, mixed with 0.1 ml of purified water, and further risen to 175° C. and heated for about 25 minutes. This was mixed with sodium bicarbonate aqueous solution, extracted several times with ethyl acetate, dried with anhydrous magnesium sulfate and concentrated, and then the thus formed residue was purified by a silica gel column chromatography to obtain 0.83 g (Reference Example 2-1) (68%) of 1-(3,5-difluorophenyl)-2-(1,3-dihydro-2H-benzimidazol-2-ylidene)-3-(3-vinylphenyl)propane-1,3-dione as a yellow foam compound from an ethyl acetate-hexane (1:3) eluate. FA: 403

The compounds shown in Tables 7 to 9 were produced in the same manner.

TABLE 7

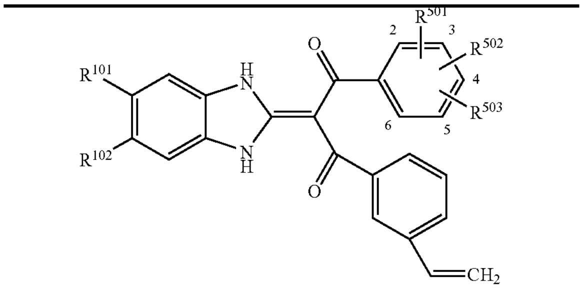

| Rex No. | $R^{501}$ | $R^{502}$ | $R^{503}$ | $R^{101}$ | $R^{102}$ | DATA |
|---|---|---|---|---|---|---|
| 2-1 | 3-F | 5-F | H | H | H | FA: 403 |
| 2-2 | 2-Cl | H | H | H | H | ES+: 401 |
| 2-3 | 2-F | H | H | H | H | ES+: 385 |
| 2-4 | 2-Me | H | H | H | H | ES+: 381 |
| 2-5 | 3-F | H | H | H | H | FA: 385 |
| 2-6 | 3-CN | H | H | H | H | ES+: 392 |
| 2-7 | 3-OMe | H | H | H | H | FA: 397 |
| 2-8 | 3-Me | H | H | H | H | ES+: 381 |
| 2-9 | 3-Cl | H | H | H | H | ES+: 401 |
| 2-10 | 3-MeOCO | H | H | H | H | ES+: 425 |
| 2-11 | 4-F | H | H | H | H | ES+: 385 |
| 2-12 | 4-Cl | H | H | H | H | ES+: 401, 403 |
| 2-13 | 4-Me | H | H | H | H | ES+: 381 |
| 2-14 | 4-CN | H | H | H | H | ES+: 392 |
| 2-15 | 3-$CF_3$ | 4-F | H | H | H | ES+: 453 |
| 2-16 | 3-F | 4-Cl | H | H | H | ES+: 419 |
| 2-17 | 2-Me | 3-F | H | H | H | ES+: 399 |
| 2-18 | 2-MeO | 5-F | H | H | H | ES+: 415 |
| 2-19 | 3-Me | 4-F | H | H | H | ES+: 399 |
| 2-20 | 2-Me | 5-Cl | H | H | H | ES+: 415 |
| 2-21 | 2-Me | 3-Me | H | H | H | ES+: 395 |
| 2-22 | 3-Me | 5-Me | H | H | H | ES+: 395 |
| 2-23 | 3-F | 5-Br | H | H | H | FA: 465 |
| 2-24 | 3-F | 5-Cl | H | H | H | FA: 419 |
| 2-25 | 3-Cl | 4-F | H | H | H | FA: 419 |
| 2-26 | 2-Cl | 5-F | H | H | H | ES+: 419 |
| 2-27 | 3-Br | 4-F | H | H | H | ES+: 463 |
| 2-28 | 3-Cl | 4-Cl | H | H | H | ES+: 435 |
| 2-29 | 2-F | 3-F | H | H | H | ES+: 403 |
| 2-30 | 2-F | 6-F | H | H | H | ES+: 403 |
| 2-31 | 3-F | 4-F | H | H | H | not purified |
| 2-32 | 3-Cl | 5-Cl | H | H | H | ES+: 435, 437 |
| 2-33 | 3-F | 5-$CF_3$ | H | H | H | FA: 453 |
| 2-34 | 2-F | 3-F | 5-F | H | H | ES+: 421 |
| 2-35 | 3-F | 4-F | 5-F | H | H | FA: 421 |
| 2-36 | 3-F | 5-Cl | H | F | H | ES+: 437 |
| 2-37 | 3-F | 5-F | H | F | H | ES+: 421 |
| 2-38 | 3-F | 5-Cl | H | F | F | ES+: 455 |
| 2-39 | 3-F | 5-F | H | F | F | ES+: 439 |
| 2-40 | 3-F | 5-F | H | Cl | H | not purified |
| 2-41 | 3-F | 5-Cl | H | F | Cl | ES+: 471 |
| 2-42 | 3-F | 5-F | H | F | Cl | ES+: 455 |

TABLE 8

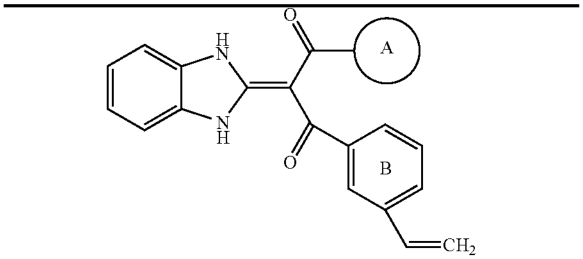

| Rex No. | ring A | DATA |
|---|---|---|
| 2-44 | 2-$CF_3$-Py5 | ES+: 436 |
| 2-45 | Thiop2 | ES+: 373 |

TABLE 8-continued

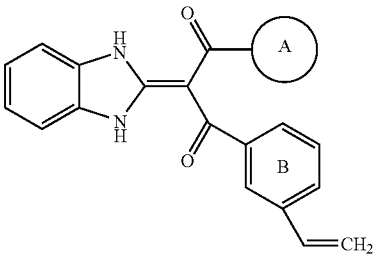

| Rex No. | ring A | DATA |
|---|---|---|
| 2-46 | 2-F-Py4 | ES+: 386 |
| 2-47 | 2,6-diCl-Py4 | ES+: 436 |
| 2-48 | Thiop3 | ES+: 373 |

TABLE 9

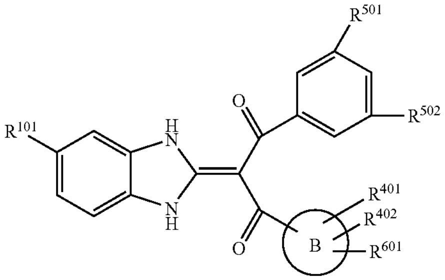

| Rex No. | $R^{501}$ | $R^{502}$ | $R^{601}$—ring B | $R^{401}$ | $R^{402}$ | $R^{101}$ | DATA |
|---|---|---|---|---|---|---|---|
| 2-49 | F | F | 3-EtOCOCH═CH-Ph- | H | H | H | FA: 475 |
| 2-50 | F | H | 3-ClCH$_2$-Ph- | H | H | H | FA: 407 |
| 2-51 | F | F | 3-ClCH$_2$-Ph- | H | H | H | FA: 425 |
| 2-52 | F | H | 3-Ac-Ph- | H | H | H | FN: 399 |
| 2-53 | F | F | 3-Ac-Ph- | H | H | H | FA: 419 |
| 2-54 | F | F | 5-Ac-Thiop2 | H | H | H | FA: 425 |
| 2-55 | F | H | 3-MeCH═CH-Ph- | 2-F | H | H | FA: 417 |
| 2-56 | F | F | 4-vin-Ph- | H | H | H | ES+: 403 |
| 2-57 | F | F | 3-vin-Ph- | 6-F | H | H | ES+: 421 |
| 2-58 | F | F | 4-vin-Ph- | H | H | F | ES+: 421 |
| 2-59 | F | F | 2-vin-Ph- | H | H | H | ES+: 403 |
| 2-60 | F | F | 3-vin-Ph- | 2-F | H | H | ES+: 421 |
| 2-61 | F | F | 3-vin-Ph- | 4-F | H | H | ES+: 421 |
| 2-62 | F | F | 3-vin-Ph- | 5-F | H | H | ES+: 421 |
| 2-63 | H | H | 3-vin-Ph- | H | H | H | ES+: 367 |
| 2-64 | F | H | 3-vin-Ph- | 2-F | H | H | ES+: 403 |
| 2-65 | F | H | 3-vin-Ph- | 4-F | H | H | ES+: 403 |
| 2-66 | F | F | 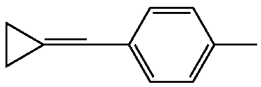 | H | H | H | ES+: 429 |
| 2-67 | F | H | 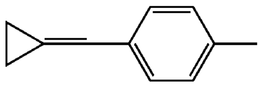 | H | H | H | ES+: 411 |
| 2-68 | F | H | 3-vin-Ph- | 2-F | 4-F | H | ES+: 421 |

Reference Example 3

A 4.96 g portion of ethyl orthoacetate dissolved in 10 ml of ethanol was added to 50 ml of ethanol solution containing 4.68 g of 4-chloro-5-fluorobenzene-1,2-diamine and heated under reflux for 4 hours. After concentration of the reaction liquid, the thus formed residue was purified by a silica gel column chromatography to obtain 2.10 g (39%) of 5-chloro-6-fluoro-2-methyl-1H-benzimidazole from a chloroform-methanol (10:1) eluate. ES+: 185

Reference Example 4-1

At −78° C., 17.62 ml of 1.59 M n-butyl lithium-THF solution was added dropwise to 100 ml of THF solution containing 4.73 ml of tetramethylpiperidine. This was stirred at −10° C. for 10 minutes, cooled to −78° C., mixed with 5.00 g of tert-butyl 2,4-difluorobenzoate dissolved in 20 ml of THF and then stirred for 1 hour. Subsequently, 7.23 ml of DMF was added dropwise thereto, and the mixture was stirred for 1 hour, mixed with 5.34 ml of acetic acid and then risen to room temperature. This was mixed with an appropriate amount of purified water, extracted with ethyl acetate and dried with anhydrous magnesium sulfate. After concentration, the thus formed residue was purified by a silica gel column chromatography to obtain 5.65 g (100%) of tert-butyl 2,4-difluoro-3-formylbenzoate (Reference Example 4-1) from a hexane-ethyl acetate (20:1-10:1) eluate.

N2: 1.60 (9H, s), 7.04 (1H, m), 8.14 (1H, m), 10.38 (1H, s)

The compounds shown by Reference Examples 4-2 and 4-3 were obtained in the same manner.

Reference Example 4-2

Tert-butyl 2-fluoro-3-formylbenzoate FA: 225

N2: 1.62 (9H, s), 7.32 (1H, t, J=8 Hz), 8.08 (2H, m), 10.42 (1H, s)

Reference Example 4-3

3-(2,2-Dimethyl-1,3-dioxolan-4-yl)-2-fluorobenzaldehyde FA: 225

Reference Example 5-1

At −78° C., 9.50 ml of 1.59 M n-butyl lithium-THF solution was added dropwise to 90 ml of THF solution containing 8.13 g of methyltriphenylphosphonium iodide. This was stirred at 0° C. for 10 minutes, cooled to −78° C. and then mixed with 2.44 g of tert-butyl 2,4-difluoro-3-formylbenzoate dissolved in 10 ml of THF. After 40 minutes thereof, this was stirred at room temperature for 1 hour, mixed with appropriate amounts of saturated ammonium chloride aqueous solution and purified water, extracted with ethyl acetate and then dried with anhydrous magnesium sulfate. After concentration, the thus formed residue was purified by a silica gel column chromatography to obtain 1.20 g (50%) of tert-butyl 2,4-difluoro-3-vinylbenzoate (Reference Example 5-1) from a hexane-ethyl acetate (50:1) eluate. ES−: 239

The compounds of the following Reference Examples 5-2 to 5-5 and those shown in Table 10 were obtained in the same manner.

Reference Example 5-2

Tert-butyl 2-fluoro-3-prop-1-en-1-ylbenzoate EI: 236

Reference Example 5-3

Methyl 3-(cyclopropylidenemethyl)benzoate FA: 189

Reference Example 5-4

Methyl 2-methoxy-3-vinylbenzoate FA: 193

Reference Example 5-5

1-Bromo-2-fluoro-3-vinylbenzene FA: 202

TABLE 10

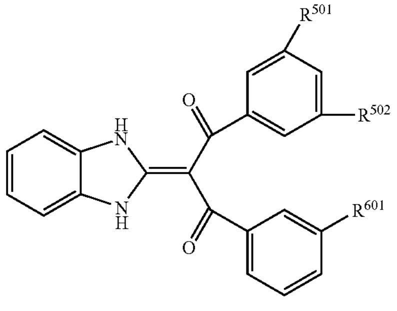

| Rex No. | $R^{501}$ | $R^{502}$ | $R^{601}$ | DATA |
|---|---|---|---|---|
| 5-6 | F | H | —CH═C(Me)$_2$ | FA: 413 |
| 5-7 | F | H | —CH═CH(Me) | FA: 399 |

TABLE 10-continued

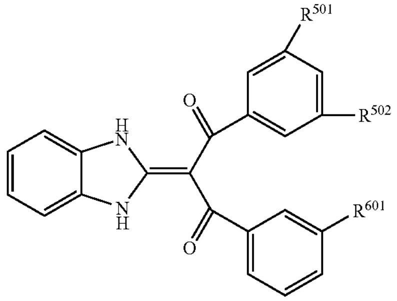

| Rex No. | $R^{501}$ | $R^{502}$ | $R^{601}$ | DATA |
|---|---|---|---|---|
| 5-8 | F | H | —CH═CHCN | FA: 410 |
| 5-9 | F | H | —CH═CH-Ph | ES+: 461 |
| 5-10 | F | F | —C(═CH$_2$)-Me | not purified |
| 5-11 | F | H | —CH═CH-iPr | FA: 427 |
| 5-12 | F | H | —CH═CHCH$_2$OMe | ES+: 429 |
| 5-13 | F | F | —CH═CHEt | ES+: 431 |
| 5-14 | F | H | —CH═CHCH$_2$N(Me)$_2$ | ES+: 442 |
| 5-15 | F | H | —CH═CH-cBu | ES+: 439 |
| 5-16 | F | F | —CH═CH-cHex | ES+: 485 |
| 5-17 | F | H | —CH═CH-cPr | FA: 425 |

Reference Example 6-1

A 4.27 ml portion of trifluoroacetic acid was added to 30 ml of dichloromethane solution containing 1.33 g of tert-butyl 2,4-difluoro-3-vinylbenzoate and stirred for 5 hours. After evaporation of the solvent, appropriate amounts of purified water and saturated sodium bicarbonate aqueous solution were added thereto and the water layer was washed with diethyl ether. The water layer was adjusted to pH 1 with 1 M hydrochloric acid aqueous solution, extracted with diethyl ether and then dried with anhydrous magnesium sulfate. After concentration, 964 mg (95%) of 2,4-difluoro-3-vinylbenzoic acid (Reference Example 6-1) was obtained.

N2: 7.93 (m, 1H), 6.98 (m, 1H), 6.74 (dd, 1H, J=12 Hz, 18 Hz), 6.11 (dd, 1H, J=1 Hz, 18 Hz), 5.68 (dd, 1H, J=1 Hz, 12 Hz)

2-Fluoro-3-prop-1-en-1-ylbenzoic acid (Reference Example 6-2) was obtained in the same manner. FN: 179

Reference Example 7-1

At −78° C., 1.0 M sodium hexamethylenedisilazane-THF solution was added dropwise to 10 ml of THF solution containing 300 mg of 3-[2-(1,3-dihydro-2H-benzimidazol-2-ylidene)-3-(3-fluorophenyl)-3-oxopropanoyl]benzaldehyde and 69 μl of acetone and stirred for 15 minutes. This was mixed with appropriate amounts of saturated ammonium chloride aqueous solution and purified water, extracted with ethyl acetate and dried with anhydrous magnesium sulfate. After concentration, the thus formed residue was purified by a silica gel column chromatography to obtain 184 mg (53%) of 2-(1,3-dihydro-2H-benzimidazol-2-ylidene)-1-(3-fluorophenyl)-3-[3-(1-hydroxy-3-oxobutyl)phenyl]propane-1,3-dione (Reference Example 7-1) from a hexane-ethyl acetate (2:1-1:2) eluate. ES+: 445

In the same manner, 1-{3-[2-(1,3-dihydro-2H-benzimidazol-2-ylidene)-3-(3-fluorophenyl)-3-oxopropanoyl]benzoyl}-2-hydroxypropyl acetate (Reference Example 7-2) was obtained. ES+: 459

Reference Example 8

A 0.57 ml portion of bromine was gradually added dropwise to 80 ml of acetic acid solution containing 4.18 g of 1-(3-acetylphenyl)-3-(3,5-difluorophenyl)-2-(1,3-dihydro-2H-benzimidazol-2-ylidene)propane-1,3-dione, and then 5 ml of 25% hydrogen bromide-acetic acid solution was added thereto and stirred as such at room temperature for about 1 hour. The solvent was evaporated under a reduced pressure, the thus formed residue was mixed with an appropriate amount of sodium bicarbonate aqueous solution and extracted several times with ethyl acetate, and the thus obtained organic layer was dried with anhydrous magnesium sulfate and concentrated to obtain an α-bromoketone intermediate. This intermediate was dissolved in 50 ml of DMSO without purification, mixed with 2.16 g of potassium acetate and stirred at room temperature for about 4 hours. The reaction liquid was mixed with an appropriate amount of saturated ammonium chloride aqueous solution, extracted several times with ethyl acetate, dried with anhydrous magnesium sulfate and concentrated, and then the thus formed residue was purified by a silica gel column chromatography to obtain 2.62 g (55%) of 2-{3-[3-(3,5-difluorophenyl)-2-(1,3-dihydro-2H-benzimidazol-2-ylidene)-3-oxopropanoyl]phenyl}-2-oxoethyl acetate as a greenish yellow foam from an ethyl acetate-hexane (1:2) eluate. FA: 477

Reference Example 9

A 25 ml portion of THF solution containing 7.8 g of tetrabutylammonium fluoride and 24 g of Molecular Sieve 4A was stirred at room temperature for 12 hours in an atmosphere of argon. After cooling to 0° C., 20 ml of THF solution containing 300 mg of 3-[2-(1,3-dihydro-2H-benzimidazol-2-ylidene)-3-(3-fluorophenyl)-3-oxopropanoyl]benzaldehyde and 1.7 g of diphenyl(2,2,2-trifluoroethyl)phosphine oxide was added dropwise thereto. This was stirred at room temperature for 5 hours. The reaction mixture was filtered, the filtrate was washed with water, dried with anhydrous sodium sulfate and concentrated, and then the thus formed residue was purified by a silica gel column chromatography to obtain 201 mg (57%) of 2-(1,3-dihydro-2H-benzimidazol-2-ylidene)-1-(3-fluorophenyl)-3-{3-[(1Z)-3,3,3-trifluoroprop-1-en-1-yl]phenyl}propane-1,3-dione as a yellow powder from an ethyl acetate-hexane (1:3) eluate. FA: 463

Reference Example 10-1

A 13.55 g portion of manganese dioxide was added to 20 ml of dichloromethane solution containing 2.11 g of 1-(3,5-difluorophenyl)-2-(1,3-dihydro-2H-benzimidazol-2-ylidene)-3-[3-(hydroxymethyl)phenyl]propane-1,3-dione and stirred for 4.5 hours. After celite filtration and concentration, the thus formed residue was crystallized from hexane-ethyl acetate to obtain 1.09 g (52%) of 3-[3-(3,5-difluorophenyl)-2-(1,3-dihydro-2H-benzimidazol-2-ylidene)-3-oxopropanoyl]benzaldehyde (Reference Example 10-1). FA: 405

In the same manner, 1-[3-(2,2-dimethyl-1,3-dioxolan-4-yl)-2-(fluorophenyl)-3-pyridin-3-ylpropane-1,3-dione (Reference Example 10-2) was obtained. FA: 344

Reference Example 11-1

A 5.46 g portion of ethyl 3-(2,2-dimethyl-1,3-dioxolan-4-yl)-2-fluorobenzoate was dissolved in 100 ml of THF and cooled to 0° C., and then 40.8 ml of 1 N sodium hydroxide aqueous solution was slowly added thereto. This was risen to room temperature and further stirred for 17 hours. After evaporation of THF, the residue was cooled to 0° C. and acetic acid was slowly added thereto until the pH value became 3 to 4. This was extracted with diethyl ether, dried with sodium sulfate and concentrated, and then subjected to azeotropic treatment three times with Tol, thereby obtaining 4.66 g (95%) of 3-(2,2-dimethyl-1,3-dioxolan-4-yl)-2-fluorobenzoic acid (Reference Example 11-1). FN: 239

In the same manner, the compounds of Reference Example 11-2 to Reference Example 11-13 shown in Table 11 were produced. In this connection, the compounds of Reference Examples 11-6 to 11-12 were produced using corresponding optically active materials.

Reference Example 12-1

After adding 35 mg of potassium acetate to 2 ml of DMSO solution containing 100 mg of 1-[3-(chloromethyl)phenyl]-3-(3,5-difluorophenyl)-2-(1,3-dihydro-2H-benzimidazol-2-ylidene)propane-1,3-dione, the mixture was stirred at room temperature for about 2 days. The reaction liquid was mixed with an appropriate amount of saturated ammonium chloride aqueous solution, extracted several times with ethyl acetate, dried with anhydrous magnesium sulfate and concentrated, and then the thus formed residue was purified by a silica gel column chromatography to obtain 90 mg of a yellow oily substance from an ethyl acetate-hexane (1:2) eluate. By crystallizing this from a small amount of ethyl acetate-hexane (1:3) at 0° C., 68 mg (64%) of 3-[3-(3,5-difluorophenyl)-2-(1,3-dihydro-2H-benzimidazol-2-ylidene)-3-oxopropanoyl]benzyl acetate (Reference Example 12-1) was obtained as yellow crystals. FA: 449

In the same manner, 3-[2-(1,3-dihydro-2H-benzimidazol-2-ylidene)-3-(3-fluorophenyl)-3-oxopropanoyl]benzyl acetate (Reference Example 12-2) was obtained. FA: 431

Reference Example 13

A 25 ml portion of THF solution containing 1.2 g of ethyl 3-{3-[3-(3,5-difluorophenyl)-2-(1,3-dihydro-2H-benzimidazol-2-ylidene)-3-oxopropanoyl]phenyl}acrylate was cooled to −78° C. in a stream of argon gas, 5.5 ml of 1.0 M diisobutylaluminum hydride-Tol solution was gradually added dropwise thereto, and then the mixture was stirred at 0° C. for about 2 hours. This was again cooled to −78° C. the same amount of the reducing agent was added dropwise thereto, and then the mixture was gradually risen to room temperature and stirred for about 40 minutes. The reaction liquid was cooled to −30° C. or lower, small amount of methanol and purified water were added thereto, and the thus formed insoluble matter was removed by filtration through washing with an appropriate amount of ethyl acetate. The organic layer obtained by layer separation operation of the filtrate was washed with water, dried with anhydrous magnesium sulfate and concentrated, and then the thus obtained residue was purified by a silica gel column chromatography to obtain 0.58 g (53%) of 1-(3,5-difluorophenyl)-2-(1,3-dihydro-2H-benzimidazol-2-ylidene)-3-[3-(3-hydroxyprop-1-en-1-yl)phenyl]propane-1,3-dione as a yellow foam from a ethyl acetate-hexane (1:1) eluate. FA: 433

Reference Example 14

A 104 mg portion of palladium acetate and 5 ml of TEA were added one by one to 50 ml of acetonitrile solution containing 7.44 g of 3-iodobenzoic acid and 3.9 ml of ethyl acrylate, and the mixture was sealed in a tube and heated at 100° C. for about 12 hours. After spontaneous cooling, the catalyst was removed by filtration while washing with appropriate amounts of methanol and ethyl acetate, and the filtrate was evaporated under a reduced pressure. The thus formed crude crystals were recrystallized from a small amount of ethanol to obtain 5.82 g (88%) of 3-(3-ethoxy-3-oxoprop-1-en-1-yl)benzoic acid as white crystals. FA: 221

Reference Example 15-1

A 1 g portion of 4-(3-bromophenyl)-2,2-dimethyl-1,3-dioxane was dissolved in 18 ml of THF solution and cooled to −78° C., and then 2.35 ml of hexane solution containing 1.57 M n-butyl lithium was added dropwise thereto spending 1 hour. After completion of the dropwise addition, this was further stirred for 30 minutes. After adding excess amount of carbon dioxide thereto at −78° C., the mixture was risen to room temperature. The reaction solution was mixed with ammonium chloride aqueous solution and extracted 10 times with chloroform-methanol (5:1), the organic layer was dried with sodium sulfate and concentrated, and then the thus formed residue was purified by a silica gel column chromatography (hexane:ethyl acetate=1:1) to obtain 550 mg (63%) of 3-(2,2-dimethyl-1,3-dioxan-4-yl)benzoic acid (Reference Example 15-1). FA: 237

In the same manner, 2-butyl-3-(2,2-dimethyl-1,3-dioxan-4-yl)benzoic acid (5%) (Reference Example 15-2) was obtained from 4-(3-bromo-2-fluorophenyl)-2,2-dimethyl-1,3-dioxane. FN: 277

Reference Example 16-1

A 5.71 g portion of ethyl 3-[(1R)-1,2-dihydroxyethyl]-2-fluorobenzoate was dissolved in 30 ml of 2,2-dimethoxypropane, mixed with 476 mg of p-toluenesulfonic acid monohydrate and stirred at room temperature for 30 minutes. This was mixed with saturated sodium bicarbonate aqueous solution and extracted with ethyl acetate, the organic layer was washed with saturated brine, dried with sodium sulfate and concentrated, and then the thus formed residue was purified by a silica gel column chromatography (hexane:ethyl acetate=10:1) to obtain 5.46 g (81%) of ethyl 3-[(4R)-2,2-dimethyl-1,3-dioxolan-4-yl]-2-fluorobenzoate (Reference Example 16-1). FA: 269

In the same manner, the compounds of the following Reference Example 16-9 and the Reference Example 16-2 to the Reference Example 16-8 shown in Table 11, were produced using corresponding optically active materials.

Reference Example 16-9

(4R)-4-(3-Bromo-2-fluorophenyl)-2,2-dimethyl-1,3-dioxolane FA: 276

Reference Example 17-1

A 12.76 g portion of ethyl 3-bromo-2-fluorobenzoate was dissolved in 50 ml of Tol solution, 15.8 ml of tributyl(vinyl)tin, 236 mg of tris(dibenzylideneacetone)dipalladium and 1.25 ml of tri-tert-butylphosphine 10 wt % hexane solution were added thereto in order, and stirred at room temperature for 13 hours in an atmosphere of argon. This was diluted with 300 ml of diethyl ether, mixed with 25 g of potassium fluoride and 5 ml of purified water and stirred for 30 minutes, the insoluble matter was filtered using a Kiriyama funnel, and then the mother liquid was concentrated. The residue was purified by a silica gel column chromatography (hexane:ethyl acetate=40:1) to obtain 10.3 g (97%) of ethyl 2-fluoro-3-vinylbenzoate (Reference Example 17-1).

In the same manner, the compounds of Reference Example 17-2 to the Reference Example 17-5 shown in Table 11 were produced.

Reference Example 18-1

A 74.3 g portion of AD-mix β was added to a mixed solvent of 265 ml tert-butanol and 265 ml purified water and dissolved therein at room temperature spending 30 minutes. After cooling to 0° C., this was mixed with 10.3 g of ethyl 2-fluoro-3-vinylbenzoate and stirred for 3.5 hours. This was mixed with 79.6 g of sodium sulfite, stirred at room temperature for 30 minutes and then extracted with ethyl acetate. The organic layer was washed with saturated brine, dried with sodium sulfate and concentrated, and then the thus formed residue was purified by a silica gel column chromatography (hexane:ethyl acetate=1:2) to obtain 5.71 g (47%) of ethyl 3-[(1R)-1,2-dihydroxyethyl]-2-fluorobenzoate (Reference Example 18-1). FA: 229

In the same manner, the following optically active compounds of Reference Example 18-8 and the Reference Example 18-2 to the Reference Example 18-7 shown in Table 11, were produced.

Furthermore, (1S)-1-phenylethane-1,2-diol derivatives were produced with AD-mix alpha in the same manner.

Reference Example 18-8

(1S)-1-(3-Bromo-2-fluorophenyl)ethane-1,2-diol

FA: 236

Reference Example 19

To a DMF solution (30 ml) containing 2.70 g of 3-bromo-2-chlorobenzoic acid were added 1.10 ml of methyl iodide and 2.38 g of potassium carbonate in order at room temperature, followed by 1 hour of stirring. The reaction liquid was mixed with water and then diluted with ethyl acetate. After a layer separation operation, the organic layer was washed with water and saturated brine in that order, dried with anhydrous magnesium sulfate and then concentrated under a reduced pressure. The thus obtained residue was purified by a silica gel column chromatography using ethyl acetate-n-hexane (100:3) as the elution solvent to obtain 2.26 g (79%) of methyl 3-bromo-2-chlorobenzoate. FA: 250

Reference Example 20

In a stream of argon, anhydrous THF solution containing 0.72 ml of N,N-diisopropylamine was cooled to about −70° C., 3.3 ml of 1.54 M n-butyl lithium-hexane solution was added dropwise thereto, and then the reaction liquid was risen to about −15° C. The reaction liquid was again cooled to about −70° C., mixed with 0.54 ml of 3-acetylpyridine and then stirred at the same temperature for about 30 minutes, and subsequently, 5 ml of anhydrous THF solution containing 1.1 g of 3-((4R)-2,2-dimethyl-1,3-dioxolan-4-yl)-2-fluorobenzaldehyde was gradually added dropwise thereto. After stirring at −70° C. for about 20 minutes and then at about −30° C. for about 3 hours, this was mixed with an appropriate amount of 0.2 M hydrochloric acid aqueous solution and subjected to several times of extraction operation with ethyl acetate. The organic layer was washed with saturated brine and dried with anhydrous magnesium sulfate, and then the solvent was evaporated and the thus formed residue was isolated and purified by a silica gel column chromatography to obtain 0.77 g (45%) of 3-[3-((4R)-2,2-dimethyl-1,3-dioxolan-4-yl)-2-fluorophenyl]-3-hydroxy-1-pyridin-3-yl-propan-1-one as a colorless oil from an ethyl acetate-hexane (7:3) eluate. FA: 346

Reference Example 21

A 4 ml portion of DMF solution containing 0.38 g of 1-[3-((4R)-2,2-dimethyl-1,3-dioxolan-4-yl)-2-fluorophenyl]-3-pyridin-3-yl-propan-1,3-dione and 1.3 g of potassium fluoride was mixed with 0.1 g of carbon disulfide, stirred at room temperature for about 2.5 hours under a closed condition, mixed with 0.16 ml of methyl iodide and then further stirred for about 1 hour under the same condition. The reaction liquid was mixed with an appropriate amount of purified water and extracted several times with ethyl acetate, and the thus obtained organic layer was washed with saturated brine and dried with anhydrous magnesium sulfate in that order. The solvent was evaporated and the thus formed residue was isolated and purified by a silica gel column chromatography to obtain 0.14 g (49%) of 2-[bis(methylsulfanyl)methylene]-1-[3-((4R)-2,2-dimethyl-1,3-dioxolan-4-yl)-2-fluorophenyl]-3-pyridin-3-yl-propan-1,3-dione as a yellow oil from an ethyl acetate-hexane (1:1) eluate. ES+: 448

TABLE 11

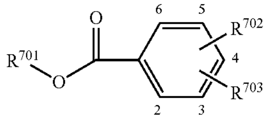

| Rex No. | $R^{701}$ | $R^{702}$ | $R^{703}$ | DATA |
|---|---|---|---|---|
| 11-2 | H | 2-F | 5-vin | FN: 165 |
| 11-3 | H | 2-F | 3-vin | FN: 165 |
| 11-4 | H | 4-F | 3-vin | FN: 165 |
| 11-5 | H | 3-F | 5-vin | FN: 165 |
| 11-6 | H | 2-Me | 3-{(2,2-diMe)-1,3-dixr4} | ES−: 235 |
| 11-7 | H | H | 3-{(2,2-diMe)-1,3-dixr4} | ES−: 221 |
| 11-8 | H | H | 3-{(2,2-diMe)-1,3-dixr4} | ES−: 221 |
| 11-9 | H | 2-F | 3-{(2,2-diMe)-1,3-dixr4} | FN: 239 |
| 11-10 | H | 4-F | 3-{(2,2-diMe)-1,3-dixr4} | FA: 241 |
| 11-11 | H | 2-OMe | 3-{(2,2-diMe)-1,3-dixr4} | ES−: 251 |
| 11-12 | H | 2-Cl | 3-{(2,2-diMe)-1,3-dixr4} | FA: 257 |
| 11-13 | H | H | 3- 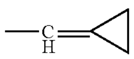 | FN: 173 |
| 16-2 | Et | 2-Me | 3-{(2,2-diMe)-1,3-dixr4} | EI: 264 |
| 16-3 | Me | H | 3-{(2,2-diMe)-1,3-dixr4} | FA: 237 |
| 16-4 | Me | H | 3-{(2,2-diMe)-1,3-dixr4} | FA: 237 |
| 16-5 | Et | 2-F | 3-{(2,2-diMe)-1,3-dixr4} | FA: 269 |
| 16-6 | Et | 4-F | 3-{(2,2-diMe)-1,3-dixr4} | FA: 269 |
| 16-7 | Me | 2-OMe | 3-{(2,2-diMe)-1,3dixr4} | FA: 267 |
| 16-8 | Me | 2-Cl | 3-{(2,2-diMe)-1,3-dixr4} | FA: 271 |
| 17-1 | Et | 2-F | 3-vin | EI: 194 |
| 17-2 | Et | 4-F | 3-vin | FA: 195 |
| 17-3 | Et | 3-F | 5-vin | EI: 194 |
| 17-4 | Et | 2-Me | 3-vin | N2: 7.44(3H, m), 7.01(1H, dd, J = 11 Hz, 17 Hz), 5.59(1H, dd, J = 1 Hz, 17 Hz), 5.35(1H, dd, J = 1 Hz, 11 Hz), 4.36(2H, q, J = 7 Hz), 2.51(3H, s), 1.39(3H, t, J = 7 Hz) |
| 17-5 | Me | 2-Cl | 3-vin | FA: 197 |
| 18-2 | Et | 2-Me | 3- 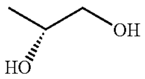 | N2: 7.42(3H, m), 5.09(1H, m), 4.33(2H, q, J = 7 Hz), 3.58(4H, m), 2.42(3H, s), 1.37(3H, t, J = 7 Hz) |
| 18-3 | Me | H | 3- 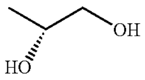 | N2: 8.00(2H, m), 7.50(2H, m), 4.89(1H, m), 3.92(3H, s), 3.73(2H, m), 2.87(1H, d, J = 3 Hz), 2.29(1H, m) |
| 18-4 | Me | H | 3- 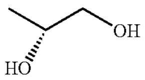 | N2: 8.00(2H, m), 7.51(2H, m), 4.89(1H, m), 3.92(3H, s), 3.73(2H, m), 2.83(1H, d, J = 3 Hz), 2.25(1H, m) |

TABLE 11-continued

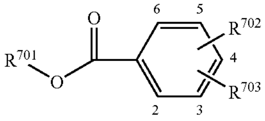

| Rex No. | $R^{701}$ | $R^{702}$ | $R^{703}$ | DATA |
|---|---|---|---|---|
| 18-5 | Et | 4-F | 3- 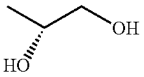 | FA: 229 |
| 18-6 | Me | 2-OMe | 3- 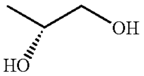 | FA: 227 |
| 18-7 | Me | 2-Cl | 3- 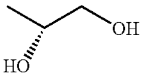 | FA: 231 |

Example 1-1

(1) An acid chloride forming reagent was prepared by adding 5 ml of dichloromethane to a stirring solution of 0.80 ml thionyl chloride and 1.31 g 1H-benzotriazole. Subsequently, the reagent prepared in the above was added to 90 ml of dichloromethane solution containing 1.96 g of (4R)-3-(2,2-dimethyl-1,3-dioxolan-4-yl)benzoic acid and stirred at room temperature for 10 minutes. After filtration of the formed chloride, anhydrous magnesium sulfate was added to the filtrate. After filtration and concentration, an acid chloride compound was obtained.

(2) At 70° C., the acid chloride compound obtained in (1) was dissolved in 10 ml of Diglyme and added dropwise to 10 ml of Diglyme solution containing 933 mg of 2-(1,3-dihydro-2H-benzimidazol-2-ylidene)-1-(3-fluorophenyl)ethanone and 1.28 ml of TEA. Next, this was risen to 100° C., mixed with 66 μl of purified water and then heated under reflux for 40 minutes. After cooling to room temperature, this was mixed with an appropriate amount of purified water, extracted with ethyl acetate and dried with anhydrous magnesium sulfate. After concentration of the organic layer, the thus formed residue was purified by a silica gel column chromatography to obtain 1.68 g (100%) of 2-(1,3-dihydro-2H-benzimidazol-2-ylidene)-1-{3-[(4R)-2,2-dimethyl-1,3-dioxolan-4-yl]phenyl}-3-(3-fluorophenyl)propane-1,3-dione (Example 1-1) from a hexane-ethyl:acetate (6:1) eluate.

In the same manner, the compounds shown in Table 12 and Table 13 were produced using corresponding optically active materials.

TABLE 12

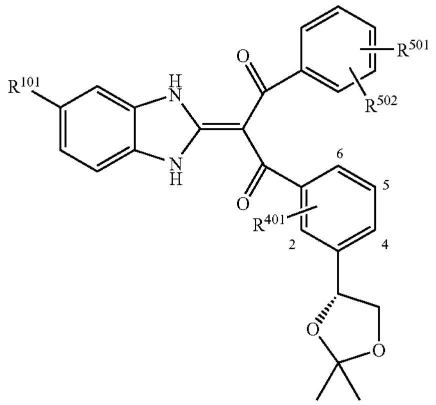

| Ex No. | $R^{101}$ | $R^{401}$ | $R^{501}$ | $R^{502}$ | DATA |
|---|---|---|---|---|---|
| 1-1 | H | H | 3-F | H | ES+: 459 |
| 1-2 | H | 2-F | 3-F | H | FA: 477 |
| 1-3 | H | 2-F | 3-CN | H | FA: 484 |
| 1-4 | H | 2-F | 2-Me | H | FA: 473 |
| 1-5 | H | 2-F | 3-Me | H | FA: 473 |
| 1-6 | H | 2-F | 2-Cl | H | ES+: 493 |
| 1-7 | H | 2-F | 2-F | H | FA: 477 |
| 1-8 | H | 2-F | H | H | FA: 459 |
| 1-9 | H | 2-F | 3-Cl | H | FA: 493 |
| 1-10 | H | H | 3-F | H | not purified |
| 1-11 | H | 4-F | 3-F | H | not purified |
| 1-12 | H | 2-Me | 3-F | H | not purified |
| 1-13 | F | 2-F | 3-F | H | not purified |
| 1-14 | H | 2-F | 3-MeO | H | not purified |
| 1-15 | H | 4-F | 3-F | 5-F | not purified |
| 1-16 | H | 4-F | 2-Cl | H | not purified |

TABLE 13

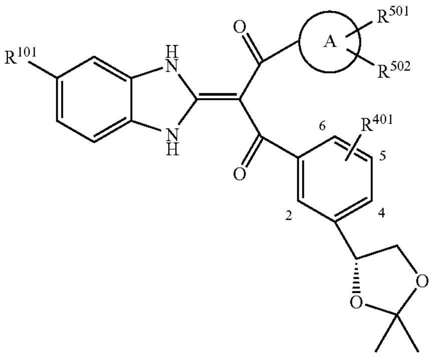

| Ex No. | $R^{101}$ | $R^{401}$ | $R^{501}$ | $R^{502}$ | ring A | DATA |
|---|---|---|---|---|---|---|
| 1-17 | H | 2-nBu | 3-F | H | Ph | FA: 515 |
| 1-18 | H | 4-F | H | H | Ph | ES+: 419 |
| 1-19 | H | 2-MeO | 3-F | H | Ph | FA: 489 |
| 1-20 | H | 2-Cl | 3-F | H | Ph | ES+: 493 |
| 1-21 | H | 2-Me | 3-F | 5-F | Ph | ES+: 491 |
| 1-22 | H | 2-Me | 3-Cl | H | Ph | ES+: 489 |
| 1-23 | H | 2-Me | 2-Cl | H | Ph | ES+: 489 |
| 1-24 | H | 2-Me | 3-Me | H | Ph | ES+: 469 |
| 1-25 | H | 2-Me | H | H | Ph | ES+: 455 |
| 1-26 | H | 2-Me | 2-F | H | Ph | ES+: 473 |
| 1-27 | H | 2-Cl | 3-F | 5-F | Ph | ES+: 511 |
| 1-28 | H | 2-Cl | 3-Cl | H | Ph | ES+: 509 |
| 1-29 | $Py3CH_2O$ | 2-F | 3-F | 5-F | Ph | FA: 602 |
| 1-30 | H | 4-F | 4-Cl | H | Ph | ES+: 493 |
| 1-31 | H | 2-Cl | 3-F | 5-F | Ph | N1: 1.40(6H, m), 2.15(3H, s) 4.39(2H, m), 5.17(1H, m), 7.03(7H, m), 7.32(2H, dt, J = 3 Hz, 9 Hz), 7.78(2H, dt, J = 3 Hz, 9 Hz), 13.20(2H, brs) |
| 1-32 | H | 2-F | 3-F | 5-F | Ph | FA: 495 |
| 1-33 | H | 2-F | H | H | Py3 | FA: 460 |
| 1-34 | H | 2-Cl | 2-Cl | H | Ph | ES+: 509 |
| 1-35 | H | 2-Cl | H | H | Ph | ES+: 475 |
| 1-36 | H | 2-Cl | 2-F | H | Ph | ES+: 493 |
| 1-37 | H | 2-Cl | 3-CN | H | Ph | ES+: 500 |
| 1-38 | H | 4-F | H | H | Ph | ES+: 459 |
| 1-39 | H | 4-F | 3-Me | H | Ph | ES+: 473 |
| 1-40 | H | 4-F | 3-Br | H | Ph | ES+: 539 |

Example 2-1

A THF (12 ml)-purified water (3 ml) solution containing 72 mg of N-methylmorpholine-N-oxide was mixed with 0.5 ml of 0.08 M osmium tetroxide-t-butanol solution and 0.82 g of 1-(3,5-difluorophenyl)-2-(1,3-dihydro-2H-benzimidazol-2-ylidene)-3-(3-vinylphenyl)propane-1,3-dione in that order, and then stirred at room temperature for about 2 hours. The reaction liquid was concentrated to about ¼ volume, mixed with an appropriate amount of sodium sulfite aqueous solution and extracted several times with ethyl acetate. The thus obtained organic layer was washed with water, dried with anhydrous magnesium sulfate and concentrated, and then the resulting residue was purified by a silica gel column chromatography to obtain 0.83 g (69%) of 1-(3,5-difluorophenyl)-2-(1,3-dihydro-2H-benzimidazol-2-ylidene)-3-[3-(1,2-dihydroxyethyl)phenyl]propane-1,3-dione (Example 2-1) as pale yellow crystals from a chloroform-methanol (80:1) eluate.

In the same manner, the compounds shown in Table 14 to Table 17 were produced.

TABLE 14

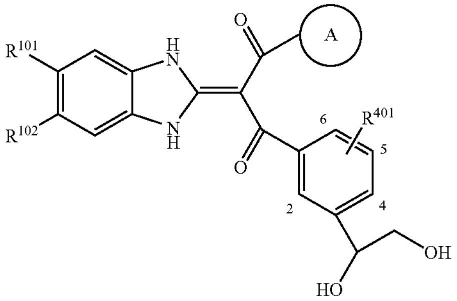

| Ex No. | $R^{101}$ | $R^{102}$ | $R^{401}$ | ring A | DATA |
|---|---|---|---|---|---|
| 2-1 | H | H | H | 3,5-diF-Ph | FA: 437 |
| 2-2 | H | H | H | 3-F-5-$CF_3$-Ph | FA: 487 |
| 2-3 | H | H | H | 3-Cl-5-F-Ph | FA: 453 |
| 2-4 | H | H | H | 3,4,5-triF-Ph | FA: 455, N1: 3.28(2H, m), 4.43(1H, dd, J = 4 Hz, 6 Hz), 4.72(1H, t, J = 6 Hz), 5.20(1H, d, J = 4 Hz), 7.20(8H, m), 7.75(2H, m), 13.12(2H, s). mp: 139-140° C. (EA-H) |
| 2-5 | F | H | H | 3,5-diF-Ph | FA: 455 |
| 2-6 | F | F | H | 3,5-diF-Ph | FA: 473 |
| 2-7 | H | H | H | 3-F-Ph | FA: 419 |
| 2-8 | H | H | H | 3,5-diCl-Ph | FA: 469 |
| 2-9 | H | H | H | 3,4-diF-Ph | FA: 437 |
| 2-10 | H | H | H | 2,6-diCl-Py-4-yl | FA: 470 |
| 2-11 | H | H | H | 2,6-diF-Ph | FA: 437 |
| 2-12 | F | Cl | H | 3,5-diF-Ph | FA: 489 |
| 2-13 | H | H | H | 4-F-Ph | FA: 419 |
| 2-14 | F | H | H | 3-Cl-5-F-Ph | FA: 471 |
| 2-5S | H | H | H | 3-MeO-Ph | FA: 431 |
| 2-16 | H | H | H | 3-Cl-4-F-Ph | FA: 453 |
| 2-17 | H | H | H | 4-CN-Ph | FA: 426 |
| 2-18 | H | H | H | 3-Br-5-F-Ph | FA: 497, 499(1:1) |
| 2-20 | H | H | 6-F | 3,5-diF-Ph | FA: 455, N1: 4.40(1H, t, J = 6 Hz), 4.73(1H, m), 5.22(1H, m), 6.77(1H, t, J = 9 Hz), 6.87(2H, m), 6.95(1H, m), 7.10(1H, m), 7.16(1H, m), 7.32(2H, m), 7.75(2H, m), 13.17(2H, s), mp: 128-129° C. (EA-H) |
| 2-21 | H | H | H | 2-Cl-Ph | FA: 435 |
| 2-22 | H | H | H | Thiop3 | FA: 407 |
| 2-23 | H | H | H | 3,5-diMe-Ph | FA: 429 |
| 2-24 | H | H | H | 2,3-diMe-Ph | FA: 429 |
| 2-25 | H | H | H | 2-F-Py4 | FA: 420 |
| 2-26 | H | H | H | Thiop2 | FA: 407 |
| 2-28 | Cl | H | H | 3,5-diF-Ph | FA: 471 |
| 2-29 | F | Cl | H | 3-Cl-5-F-Ph | FA: 505 |
| 2-31 | H | H | H | 3-MeOCO-Ph | FA: 459 |
| 2-32 | H | H | H | 3-Cl-6-Me-Ph | FA: 449 |
| 2-33 | H | H | H | 4-F-3-Me-Ph | FA: 433 |
| 2-34 | F | F | H | 3-Cl-5-F-Ph | FA: 489 |
| 2-35 | H | H | H | 2-$CF_3$-Py5 | FA: 470 |
| 2-36 | H | H | H | 3-N$(Me)_2SO_2$-Ph | FA: 508 |

TABLE 15

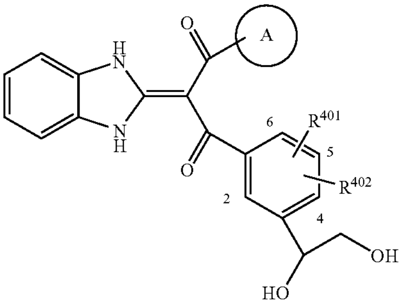

| Ex No. | ring A | $R^{401}$ | $R^{401}$ | DATA |
|---|---|---|---|---|
| 2-37 | 3,5-diF-Ph | 2-F | H | FA: 455, N1: 3.15(1H, m), 3.32(1H, m), 4.64(1H, m), 4.79(1H, m), 5.26(1H, m), 6.92(4H, m), 7.11(1H, t, |

TABLE 15-continued

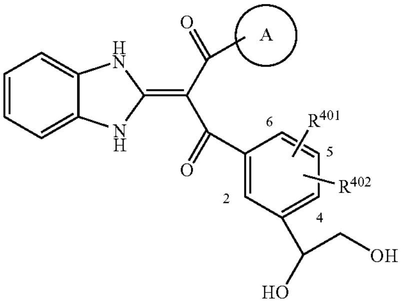

| Ex No. | ring A | $R^{401}$ | $R^{401}$ | DATA |
|---|---|---|---|---|
| | | | | J = 6 Hz), 7.27(1H, t, J = 6 Hz), 7.32(2H, m), 7.75(2H, m), 13.18(2H, s), mp: 218-219° C. (EA-H) |
| 2-38 | 3,5-diF-Ph | 4-F | H | FA: 455, N1: 3.24(2H, m), 4.68(1H, m), 4.84(1H, t, J = 6 Hz), 5.38(1H, d, J = 5 Hz), 6.89(3H, m), 6.96(1H, m), 7.29(3H, m), 7.44(1H, m), 7.73(2H, m), 13.09(2H, s), mp: 202-203° C. (EA-H) |
| 2-39 | 3,5-diF-Ph | 5-F | H | FA: 455 |
| 2-40 | 3-F-6-MeO-Ph | H | H | FA: 449 |
| 2-41 | 3-F-2-Me-Ph | H | H | FA: 433 |
| 2-42 | 3-Me-Ph | H | H | FA: 415 |
| 2-43 | 4-Cl-3-F-Ph | H | H | FA: 453 |
| 2-44 | 4-F-3-$CF_3$-Ph | H | H | FA: 487 |
| 2-45 | 3-CN-Ph | H | H | FA: 426 |
| 2-46 | 3-Br-4-F-Ph | H | H | FA: 497, 499(1:1) |
| 2-47 | 3,4-diCl-Ph | H | H | FA: 469 |
| 2-48 | 2,3,5-triF-Ph | H | H | FA: 455 N1: 4.44(1H, m), 4.72(1H, t, J = 6 Hz), 5.18(1H, d, J = 4 Hz), 6.89(1H, m), 7.15(4H, m), 7.32(3H, m), 7.76(2H, dd, J = 3 Hz, 6 Hz), 13.19(2H, s), mp: 127-129° C. (EA-H) |
| 2-49 | Ph | H | H | FA: 401 |
| 2-50 | 3-Cl-Ph | H | H | FA: 435 |
| 2-51 | 4-Cl-Ph | H | H | FA: 435 |
| 2-52 | 2-Me-Ph | H | H | FA: 415 |
| 2-53 | 4-Me-Ph | H | H | FA: 415 |
| 2-54 | 3-F-Ph | 2-F | H | FA: 437 |
| 2-55 | 3-F-Ph | 4-F | H | FA: 437 |
| 2-56 | 2-Cl-5-F-Ph | H | H | FA: 453 |
| 2-57 | 2-F-Ph | H | H | FA: 419 |
| 2-58 | 2,3-diF-Ph | H | H | FA: 437 N1: 4.42(1H, m), 4.69(1H, t, J = 6 Hz), 5.14(1H, d, J = 4 Hz), 7.10(9H, m), 7.75(2H, m), 13.17(2H, s), mp: 129-131° C. (EA-H) |
| 2-59 | 3-F-Ph | 2-F | 4-F | FA: 455 |

TABLE 16

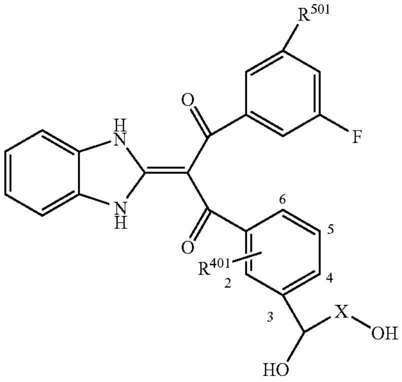

| Ex No. | $R^{401}$ | $R^{501}$ | X | DATA |
|---|---|---|---|---|
| 2-60 | H | F | 1,1-cPr-diyl | FA: 463 |
| 2-61 | H | F | —CH(COOEt)— | FA: 509 |
| 2-62 | H | F | —CH(OH)$CH_2$— | FA: 467, N1: 2.97(1H, m), 3.31(2H, m), 4.42(2H, m), 4.50(1H, d, J = 6 Hz), 5.01(1H, d, J = 6 Hz), |

TABLE 16-continued
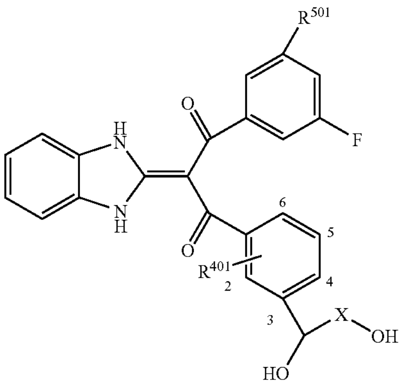
| Ex No. | $R^{401}$ | $R^{501}$ | X | DATA |
|---|---|---|---|---|
| | | | | 6.92(3H, m), 7.14(3H, m), 7.31(3H, m), 7.73(2H, m), 13.07(2H, s), mp: 187-188° C. (EA-H) |
| 2-63 | H | H | 1,1-cPr-diyl | FA: 445 |
| 2-64 | H | H | —$C(Me)_2$— | FA: 447 |
| 2-65 | H | H | —CH(Me)— | FA: 433, N1: 0.70(3H, m), 3.53(1H, m), 4.24(1H, m), 4.51(1H, m), 5.05(1H, m), 6.90(1H, m), 7.16(9H, m), 7.72(2H, m), 13.06(2H, s), mp: 122-123° C. (EA-H) |
| 2-66 | H | H | —CH(CN)— | FA: 444 |
| 2-67 | H | H | —CH(Ph)— | FA: 495 |
| 2-68 | H | H | —CH(i-Pr)— | ES+: 461 |
| 2-69 | H | H | —$CH(MeOCH_2)$— | ES+: 463 |
| 2-70 | H | F | —CH(Et)— | ES+: 465 |
| 2-71 | H | H | —$CH[N(Me)_2CH_2]$— | FA: 476 |
| 2-72 | H | H | —CH(cBu)— | FA: 473 |
| 2-73 | H | F | —CH(cHex)— | FA: 519 |
| 2-74 | H | H | —CH(cPr)— | FA: 459 |
| 2-75 | 2-F | H | —CH(Me)— | FA: 451 |
| 2-76 | H | H | —$CH(CF_3)$— | FA: 487 |
TABLE 17
| Ex No. | STR | DATA |
|---|---|---|
| 2-19 | 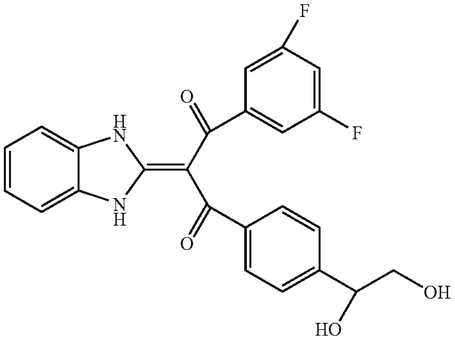 | ES+: 437 |

TABLE 17-continued
| Ex No. | STR | DATA |
|---|---|---|
| 2-27 | 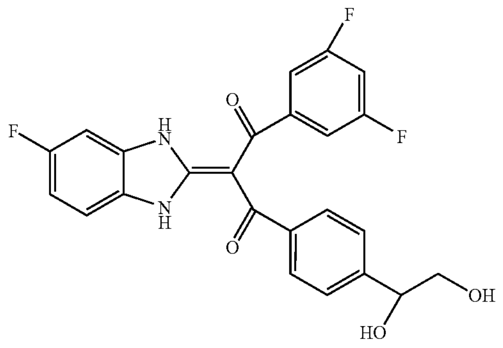 | FA: 455 |
| 2-30 | 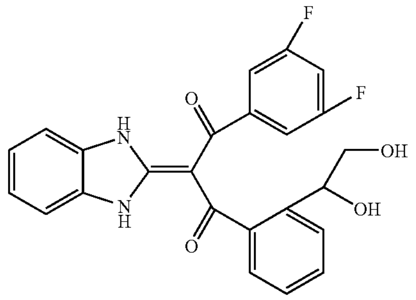 | FA: 437 |
| 2-77 | 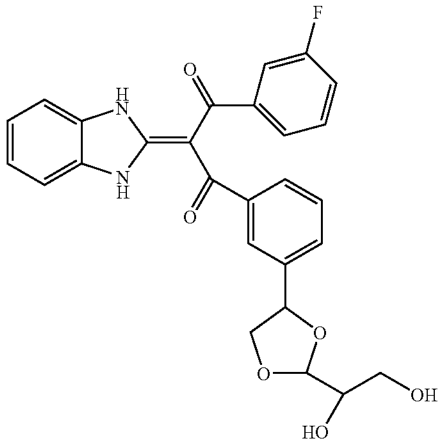 | ES+: 491 |

TABLE 17-continued

| Ex No. | STR | DATA |
|---|---|---|
| 2-78 | 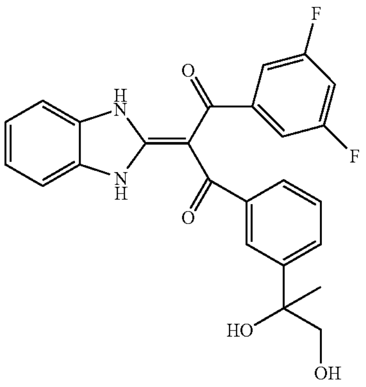 | FA: 451 |

Example 3-1

A 6 ml portion of THF solution containing 0.21 g of 2-(1,3-dihydro-2H-benzimidazol-2-ylidene)-1-[3-(1,2-dihydroxyethyl)phenyl]-3-(3-fluorophenyl)propane-1,3-dione and 0.3 g of methyl orthoacetate was mixed with 63 mg of pyridinium p-toluenesulfonate and then stirred at room temperature for about 30 minutes. After evaporation of the solvent, the residue was mixed with an appropriate amount of sodium bicarbonate aqueous solution, extracted several times with ethyl acetate, dried with anhydrous magnesium sulfate and concentrated. The thus formed residue was purified by a silica gel column chromatography to obtain 162 mg (68%) of 2-(1,3-dihydro-2H-benzimidazol-2-ylidene)-1-(3-fluorophenyl)-3-[3-(2-methoxy-2-methyl-1,3-dioxolan-4-yl)phenyl]propane-1,3-dione (Example 3-1) as a pale yellow foam from an ethyl acetate-hexane (1:2) eluate.

In the same manner, the compounds shown in Table 18 were produced.

TABLE 18

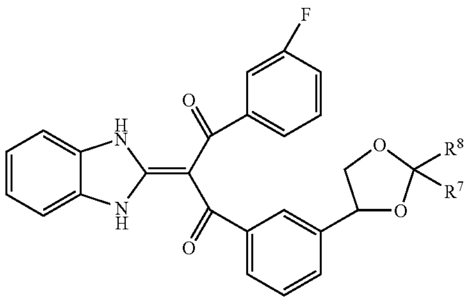

| Ex No. | $R^7$ | $R^8$ | DATA |
|---|---|---|---|
| 3-1 | MeO | Me | FA: 475, N1: 1.55(3H, s), 3.28(3H, m), 3.41(1H, m), 4.32(1H, m), 5.07(1H, m), 6.92(1H, m), 7.10(5H, m), 7.30(4H, m), 7.74(2H, m), 13.13(2H, s). |
| 3-2 | MeO | H | FA: 461, N1: 3.30(3H, m), 3.43(1H, m), 4.31(1H, m), 5.05(1H, m), 5.95(1H, m), 6.91(1H, m), 7.09(5H, m), 7.29(4H, m), 7.74(2H, m), 13.13(2H, s). |
| 3-3 | vin | H | FA: 457 |
| 3-4 | EtO | Et | FA: 503 |

Example 4-1

A 20 ml portion of methanol solution containing 1.68 g of 2-(1,3-dihydro-2H-benzimidazol-2-ylidene)-1-{3-[(4R)-2,2-dimethyl-1,3-dioxolan-4-yl]phenyl}-3-(3-fluorophenyl)propane-1,3-dione was mixed with 560 mg of p-toluenesulfonic acid monohydrate and stirred at room temperature for 18 hours. This was mixed with appropriate amounts of purified water and saturated sodium bicarbonate aqueous solution, extracted with ethyl acetate and dried with anhydrous magnesium sulfate. After concentration, the thus formed residue was purified by a silica gel column chromatography to obtain 640 mg (42%) of 2-(1,3-dihydro-2H-benzimidazol-2-ylidene)-1-{3-[(1R)-1,2-dihydroxyethyl]phenyl}-3-(3-fluorophenyl)propane-1,3-dione (Example 4-1) from a hexane-ethyl acetate (3:1-1:3) eluate.

In this connection, the compound of Example 4-11 was produced by the following method.

A 140 mg portion of 3-(2-(1,3-dihydro-2H-benzimidazol-2-ylidene)-3-{3-[(4R)-2,2-dimethyl-1,3-dioxolan-4-yl]-2-fluorophenyl}-3-oxopropanoyl)benzonitrile was dissolved in 5 ml of acetic acid-water (4:1) and stirred at 50° C. for 3 hours. The solvent was evaporated to carry out an azeotropic treatment using Tol. The thus formed residue was purified by a silica gel column chromatography, and the foamy substance obtained from a chloroform-methanol (10:0-9:1) eluate was recrystallized from ethyl acetate hexane to obtain 105 mg (82%) of 3-(2-(1,3-dihydro-2H-benzimidazol-2-ylidene)-3-{3-[(1R)-1,2-dihydroxyethyl]-2-fluorophenyl}-3-oxopropanoyl)benzonitrile (Example 4-11).

In the same manner, the compounds shown in Tables 19 to 21 were produced using corresponding optically active materials derived from the dihydroxy compounds synthesized using AD-mix beta.

TABLE 19

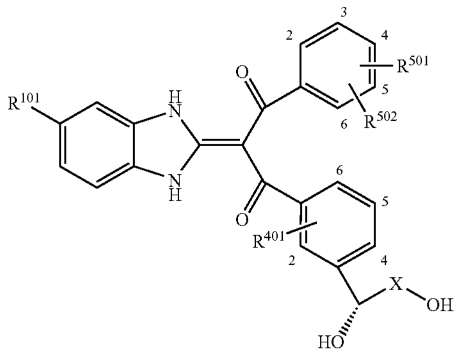

| Ex No. | $R^{401}$ | $R^{501}$ | $R^{502}$ | X | $R^{101}$ | Salt | DATA |
|---|---|---|---|---|---|---|---|
| 4-1 | H | 3-F | H | $—CH_2—$ | H | — | FA: 419 N1: 4.40(1H, m), 4.68(1H, t, J = 6 Hz), 5.15(1H, d, J = 4 Hz), 7.10(10H, m), 7.73(2H, m), 13.09(2H, s), mp: 190-191° C. (EA-H) |
| 4-2 | H | 3-F | 5-F | $—(CH_2)_2—$ | H | — | FA: 451 |
| 4-3 | 4-F | 3-F | H | $—CH_2—$ | H | — | FA: 437 N1: 4.66(1H, m), 4.82(1H, t, J = 6 Hz), 5.37(1H, d, J = 5 Hz), 7.14(9H, m), 7.73(2H, m), 13.08(2H, s), mp: 127-128° C. (EA-H) |
| 4-4 | 2-F | 3-F | H | $—CH_2—$ | H | — | FA: 437, N1: 3.11(1H, m), 3.31(1H, m), 4.62(1H, m), 4.77(1H, t, J = 6 Hz), 5.23(1H, d, J = 4 Hz), 6.92(2H, m), 6.99(1H, m), 7.09(3H, m), 7.19(1H, m), 7.31(2H, m), 7.75(2H, m), 13.17(2H, s), mp: 197-198° C. (EA-H) |
| 4-5 | 2-Me | 3-F | 5-F | $—CH_2—$ | H | — | FA: 451 N1: 2.34(3H, s), 3.50(2H, m), 4.95(1H, m), 6.48(1H, m), 6.73(2H, m), 6.98(2H, m), 7.29(1H, m) 7.40(2H, m), 7.53(2H, m), 12.70(1H, brs), 13.10(1H, brs), mp: 228-229° C. (EtOH) |
| 4-6 | H | 3-F | H | $—CH_2—$ | H | — | FA: 419 |
| 4-7 | 2-F | H | H | $—CH_2—$ | H | — | FA: 419 |
| 4-8 | 2-nBu | 3-F | H | $—CH_2—$ | H | — | FA: 475 N1: 0.90(3H, t, J = 7 Hz), 1.17(4H, m), 1.83(1H, m), 2.29(1H, m), 2.93(1H, m), 3.06(1H, m), 4.55-4.63(1H, m), 4.71((1H, t, J = 6 Hz), 5.00(1H, m), 6.79-6.94(5H, m), 7.04(1H, m), 7.14(1H, m), 7.29(2H, dd, J = 3 Hz, 9 Hz), 7.75(2H, dt, J = 3 Hz, 9 Hz) 13.10(2H, s), mp: 132-133° C. (EA-H) |
| 4-9 | 2-F | 3-Cl | H | $—CH_2—$ | H | — | FA: 453 N1: 4.63(1H, m), 4.78(1H, t, J = 6 Hz), 5.24(1H, d, J = 4 Hz), 7.12(9H, m), 7.76(2H, m), 13.18(2H, s), mp: 139-140° C. (EA-H) |
| 4-10 | 2-F | 3-F | H | $—CH_2—$ | F | — | FA: 455, N1: 3.11(1H, m), 3.32(1H, m), 4.62(1H, m), 4.78(1H, t, J = 6 Hz), 5.23(1H, d, J = 5 Hz), 6.95(3H, m), 7.10(3H, m), 7.19(2H, m), 7.54(1H, m), 7.72-7.75(1H, m), 13.22(2H, s), mp: 208-209° C. (EA-H) |
| 4-11 | 2-F | 3-CN | H | $—CH_2—$ | H | — | FA: 444 |
| 4-12 | 2-F | 3-MeO | H | $—CH_2—$ | $Py3CH_2O$ | oxal | ES+: 562 |

TABLE 20

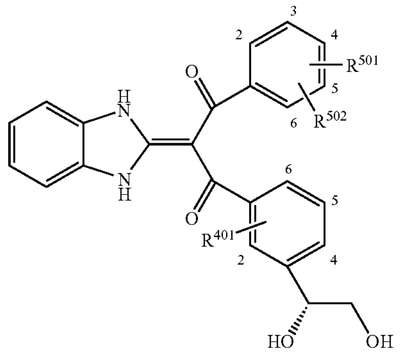

| Ex No. | $R^{501}$ | $R^{502}$ | $R^{401}$ | DATA |
|---|---|---|---|---|
| 4-13 | 2-Cl | H | 2-Me | FA: 449 |
| 4-14 | 3-Me | H | 2-F | FA: 433 |
| 4-15 | 3-Cl | H | 2-Cl | ES+: 469 N1: 2.93(1H, m), 4.76(2H, m), 5.33(1H, m), 7.09(6H, m), 7.25(1H, m), 7.33(2H, dt, J = 3 Hz, 9 Hz), 7.77(2H, dt, J = 3 Hz, 9 Hz) 13.24(2H, brs), mp: 134-136° C. (EA-ET-H) |
| 4-16 | 2-Me | H | 2-F | FA: 433 |
| 4-17 | 2-Cl | H | 4-F | FA: 453 N1: 4.66(1H, m), 4.81(1H, m), 5.34(1H, d, J = 5 Hz), 6.77(1H, m), 7.01 (3H, m), 7.16(2H, m), 7.32(2H, dd, J = 3 Hz, 6 Hz), 7.42(1H, m), 7.75(2H, dd, J = 3 Hz, 6 Hz), 13.20(2H, s) mp: 135-137° C. (EA-H) |
| 4-18 | 3-Cl | H | 4-F | FA: 453 N1: 3.26(2H, m), 4.67(1H, m), 5.35(1H, m), 6.86(1H, m), 7.08(1H, m), 7.23(6H, m), 7.45(1H, m), 7.75(2H, m) 13.08(2H, s). |
| 4-19 | 3-F | H | 2-MeO | FA: 449 |
| 4-20 | 3-F | H | 2-Me | FA: 433 N1: 4.61(1H, brs), 4.71(1H, t, J = 6 Hz), 5.02(1H, brs), 6.99(7H, m), 7.31(2H, m), 7.75(2H, m), 13.18(2H, s), mp: 139-141° C. (EA-H) |
| 4-21 | 3-F | H | 2-Cl | FA: 453 N1: 2.91(1H, m), 4.78(2H, m), 5.34(1H, m), 6.98(6H, m), 7.24(1H, m), 7.33(2H, dt, J = 3 Hz, 9 Hz), 7.77(2H, dt, J =3 Hz, 9 Hz) 13.25(2H, brs), mp: 125-127° C. (EA-H) |
| 4-22 | 3-F | 5-F | 4-F | FA: 455 N1: 4.68(1H, m), 4.85(1H, m), 5.40(1H, d, J = 4 Hz), 6.95(4H, m), 7.30(3H, m), 7.45(1H, dd, J = 2 Hz, 7 Hz), 7.74(2H, dd, J = 3 Hz, 6 Hz), 13.10(2H, s), mp: 147-149° C. (EA-H) |
| 4-23 | 3-Cl | H | 2-Me | ES+: 449 N1: 2.31(3H, s), 3.32(1H, m), 3.58(1H, m), 4.92(1H, m), 7.00(4H, m), 7.12(2H, m), 7.23(1H, m), 7.38(2H, m), 7.51 (2H, m), 12.70(1H, brs), 13.10(1H, brs) |
| 4-24 | 2-Cl | H | 2-F | FA: 453 |
| 4-25 | 3-Me | H | 2-Me | FA: 429 N1: 2.18(3H, s), 2.26(3H, s), 3.47(2H, m), 4.85(1H, m), 6.94(5H, m), 7.17(1H, m), 7.36(2H, m), 7.50(2H, m), mp: 196-197° C. (EA-H) |
| 4-26 | 3-MeO | H | 2-F | FA: 449 |
| 4-27 | H | H | 2-Me | ES+: 415 |

TABLE 21

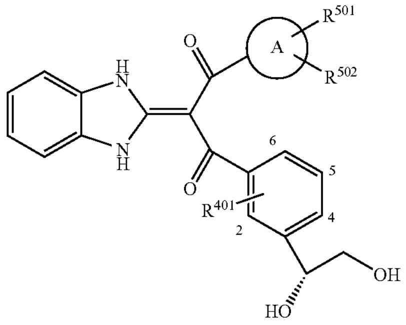

| Ex No. | ring A | $R^{501}$ | $R^{502}$ | $R^{401}$ | DATA |
|---|---|---|---|---|---|
| 4-28 | Ph | 2-F | H | 2-F | FA: 437 |
| 4-29 | Ph | 2-F | H | 2-Me | ES+: 433, N1: 2.23(3H, s), 3.46(2H, m), 4.93(1H, m), 6.62(1H, m), 6.82(1H, m), 7.12(5H, m), 7.41(1H, m), 7.52(1H, m), 13.10(2H, m), mp: 215-217° C. (EA-H) |
| 4-30 | Ph | 3-F | 5-F | 2-Cl | ES+: 471<br>N1: 2.98(1H, m), 4.81(2H, m), 5.48(1H, m), 6.87(3H, m), 7.09(2H, m), 7.29(3H, m)<br>7.75(2H, dt, J = 3 Hz, 9 Hz), 13.27(2H, brs), mp: 126-129° C. (EA-ET-H) |
| 4-31 | Ph | 4-Cl | H | 4-F | ES+: 453 |
| 4-32 | Ph | 3-Me | H | 2-Cl | FA: 449<br>N1: 2.15(3H, s), 2.86(1H, m), 4.75(1H, m), 4.78(1H, t, J = 6 Hz)<br>527(1H, M), 6.96(6H, m), 7.19(1H, m), 7.32(2H, dt, J = 3 Hz, 9 Hz)<br>7.75(2H, dt, J = 3 Hz, 9 Hz), 13.20(2H, brs) |
| 4-33 | Ph | 3-F | 5-F | 2-F | FA: 455<br>N1: 3.15(1H, m), 3.32(1H, m), 4.64(1H, m), 4.79(1H, m), 5.26(1H, m), 6.92(4H, m), 7.11(1H, t, J = 6 Hz), 7.27(1H, t, J = 6 Hz), 7.32(2H, m), 7.75(2H, m), 13.18(2H, s), mp: 218-219° C. (EA-H) |
| 4-34 | Py3 | H | H | 2-F | ES+: 420 |
| 4-35 | Ph | 4-Cl | H | 2-Cl | ES+: 469 |
| 4-36 | Ph | H | H | 2-Cl | ES+: 435 |
| 4-37 | Ph | 2-F | H | 2-Cl | FA: 453 |
| 4-38 | Ph | 3-NC | H | 2-Cl | FA: 460 |
| 4-39 | Ph | H | H | 2-Cl | ES+: 419 |
| 4-40 | Ph | 3-Me | H | 4-F | ES+: 433 |
| 4-41 | Ph | 3-Br | H | 4-F | ES+: 497, 499(1:1) |

Example 5

A chloroform solution containing 0.11 g of 1-(3,5-difluorophenyl)-2-(1,3-dihydro-2H-benzimidazol-2-ylidene)-3-{3-[1-hydroxy-2-(methylsulfanil)ethyl]phenyl}propane-1,3-dione was mixed with 0.13 g of 77% 3-chloroperbenzoic acid and stirred at room temperature for about 30 minutes. The reaction liquid was mixed with an appropriate amount of sodium bicarbonate aqueous solution, extracted several times with ethyl acetate, dried with anhydrous magnesium sulfate and concentrated, and then the thus formed residue was purified by a silica gel column chromatography to obtain 85 mg (71%) of 1-(3,5-difluorophenyl)-2-(1,3-dihydro-2H-benzimidazol-2-ylidene)-3-{3-[1-hydroxy-2-(methylsulfonyl)ethyl]phenyl}propane-1,3-dione as a yellow foam from a chloroform-methanol (100:1) eluate. ES+: 499

Example 6-1

At −10° C., 10 ml of ethanol solution containing 184 mg of 2-(1,3-dihydro-2H-benzimidazol-2-ylidene)-1-(3-fluorophenyl)-3-[3-(1-hydroxy-3-oxobutyl)phenyl]propane-1,3-dione was mixed with sodium borohydride and stirred for 30 minutes. This was appropriate amounts of saturated ammonium chloride aqueous solution and purified water, extracted with ethyl acetate and dried with anhydrous magnesium sulfate. After concentration, the thus formed residue was purified by a silica gel column chromatography to obtain 110 mg (60%) of 2-(1,3-dihydro-2H-benzimidazol-2-ylidene)-1-[3-(1,3-dihydroxybutyl)phenyl]-3-(3-fluorophenyl)propane-1,3-dione (Example 6-1) from a hexane-ethyl:acetate (1:1-1:3) eluate.

In the same manner, the compounds shown in Table 22 were produced.

TABLE 22

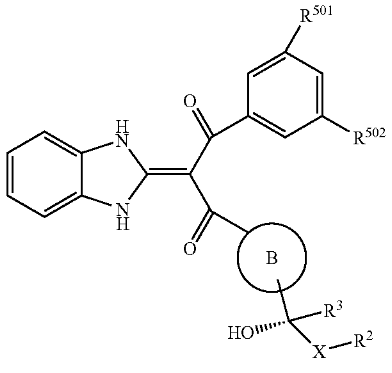

| Ex No. | $R^{501}$ | $R^{502}$ | ring B | $R^2$ | $R^3$ | X | DATA |
|---|---|---|---|---|---|---|---|
| 6-1 | F | H | pheny-1,3-diyl | —OH | H | —$CH_2CH(Me)$— | FA: 447 |
| 6-2 | F | H | pheny-1,3-diyl | Cl | H | —$CH_2$— | FA: 437 |
| 6-3 | F | F | pheny-1,3-diyl | H | Me | bond | FA: 421 |
| 6-4 | F | F | pheny-1,3-diyl | —OAc | H | —$CH_2$— | FA: 479 |
| 6-5 | F | F | Thiop-2,5-diyl | —OAc | H | —$CH_2$— | not purified |
| 6-6 | F | F | pheny-1,3-diyl | —$N(Me)_2$ | H | —$CH_2$— | FA: 464 |
| 6-7 | F | F | pheny-1,3-diyl | —SMe | H | —$CH_2$— | FA: 467 |
| 6-8 | F | F | pheny-1,3-diyl | —$N_3$ | H | —$CH_2$— | not purified |
| 6-9 | F | H | pheny-1,3-diyl | —OH | H | —CH(OAc)CH(Me)— | ES+: 505 |

Example 7-1

To 5 ml of DMF solution containing 200 mg of 2-(1,3-dihydro-2H-benzimidazol-2-ylidene)-1-[3-(1,2-dihydroxyethyl)phenyl]-3-(3-fluorophenyl)propane-1,3-dione and 53 µl of 2-methylpropanoic acid were added 88 mg of 1-hydroxybenzotriazole monohydrate, 110 mg of WSCHCl and 70 mg of dimethylaminopyridine in that order, and the mixture was stirred at room temperature for 18 hours. This was mixed with an appropriate amount of purified water, extracted with ethyl acetate and dried with anhydrous magnesium sulfate. After concentration, the thus formed residue was purified by a silica gel column chromatography to obtain 90 mg (39%) of 2-{3-[2-(1,3-dihydro-2H-benzimidazol-2-ylidene)-3-(3-fluorophenyl)-3-oxopropanoyl]phenyl}-2-hydroxyethyl-2-methyl propanoate (Example 7-5) from a hexane-ethyl acetate (2:1-0:1) eluate.

In the same manner, the compounds shown in Table 23 were produced.

TABLE 23

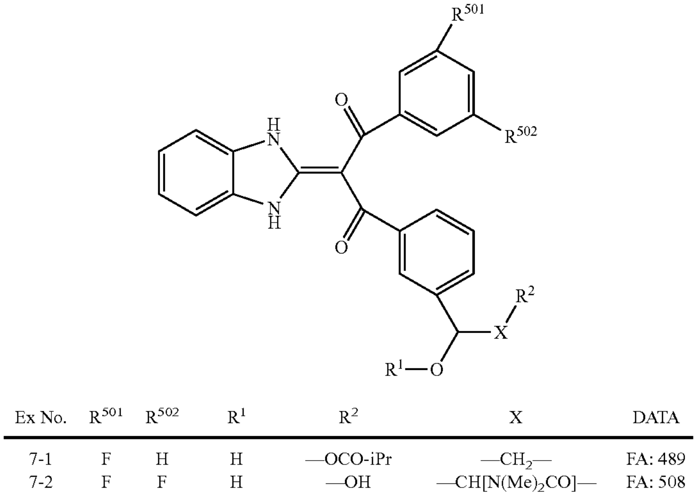

| Ex No. | $R^{501}$ | $R^{502}$ | $R^1$ | $R^2$ | X | DATA |
|---|---|---|---|---|---|---|
| 7-1 | F | H | H | —OCO-iPr | —$CH_2$— | FA: 489 |
| 7-2 | F | F | H | —OH | —$CH[N(Me)_2CO]$— | FA: 508 |
| 7-3 | F | H | —COMe | —OCOMe | —$CH_2$— | FA: 503 |
| 7-4 | F | H | —CO-iPr | —OCO-iPr | —$CH_2$— | FA: 559 |
| 7-5 | F | H | H | —OCOMe | —$CH_2$— | FA: 489 |

Example 8

A 0.35 g portion of 2-(1,3-dihydro-2H-benzimidazol-2-ylidene)-1-[3-(1,2-dihydroxyethyl)phenyl]-3-(3-fluorophenyl)propane-1,3-dione was added to 10 ml of DMF solution containing 0.14 g of N,N-dimethylglycine hydrochloride, 0.14 g of HOBt, 0.19 g of WSCHCl and 0.28 ml of TEA, and then the mixture was stirred at room temperature for about 12 hours. The reaction liquid was mixed with an appropriate amount of ammonium chloride aqueous solution, extracted several times with ethyl acetate, dried with anhydrous magnesium sulfate and concentrated, and then the thus formed residue was purified by a silica gel column chromatography to obtain 0.3 g of a yellow foam from a chloroform-methanol (50:1) eluate. This was dissolved in 15 ml of ethyl acetate, 0.5 ml of 4 N hydrochloric acid-ethyl acetate solution was added dropwise thereto, the mixture was stirred at room temperature for about 15 minutes, and then the thus formed crystals were collected by filtration and dried to obtain 0.2 g (44%) of 2-{3-[2-(1,3-dihydro-2H-benzimidazol-2-ylidene)-3-(3-fluorophenyl)-3-oxopropanoyl]phenyl}-2-hydroxyethyl (dimethylamino)acetate hydrochloride as white crystals. FA: 504

Example 9-1

A 10 ml portion of THF solution containing 104 mg of 1-[{3-[2-(1,3-dihydro-2H-benzimidazol-2-ylidene)-3-(3-fluorophenyl)-3-oxopropanoyl]phenyl}(hydroxy)methyl]-2-hydroxypropyl acetate and 2 ml of methanol solution were mixed with 0.62 ml of 1.0 M sodium hydroxide and stirred for 30 minutes. This was mixed with appropriate amounts of saturated ammonium chloride aqueous solution and purified water, extracted with ethyl acetate and dried with anhydrous magnesium sulfate. After concentration, the thus formed residue was purified by a silica gel column chromatography to obtain 35 mg (37%) of 2-(1,3-dihydro-2H-benzimidazol-2-ylidene)-1-(3-fluorophenyl)-3-[3-(1,2,3-trihydroxybutyl) phenyl]propane-1,3-dione (Example 9-1) from a hexane-ethyl acetate (1:1-1:3) eluate.

In the same manner, the compounds shown in Table 24 and Examples 9-5 and 9-6 were produced.

Example 9-5

2-(1,3-dihydro-2H-benzimidazol-2-ylidene)-1-(3-fluorophenyl)-3-[3-(hydroxymethyl)phenyl]propane-1,3-dione

FA: 389

Example 9-6

1-(3,5-difluorophenyl)-2-(1,3-dihydro-2H-benzimidazol-2-ylidene)-3-[3-(hydroxymethyl)phenyl]propane-1,3-dione

FA: 407

TABLE 24

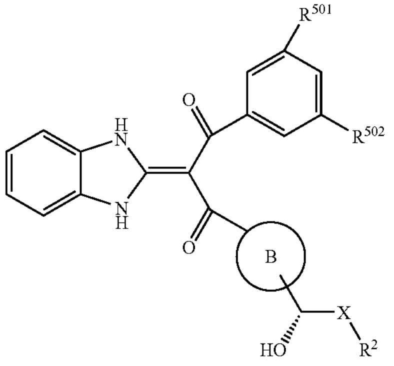

| Ex No. | $R^{501}$ | $R^{502}$ | ring B | $R^2$ | X | DATA |
|---|---|---|---|---|---|---|
| 9-1 | F | H | pheny-1,3-diyl | —OH | —CH(OH)CH(Me)— | ES+: 463 |
| 9-2 | F | F | pheny-1,3-diyl | H | Bond | FA: 407 |
| 9-3 | F | F | Thiop-2,5-diyl | —OH | $—CH_2—$ | FA: 443 |
| 9-4 | F | F | pheny-1,3-diyl | —OH | —CH(COOH)— | FA: 481 |

Example 10

Under ice-cooling, 0.54 g of sodium periodate was added to 3 ml of THF-methanol aqueous solution (1:1:1) containing 0.25 g of 2-(1,3-dihydro-2H-benzimidazol-2-ylidene)-1-{3-[2-(1,2-dihydroxyethyl)-1,3-dioxolan-4-yl]phenyl}-3-(3-fluorophenyl)propane-1,3-dione and stirred at room temperature for about 30 minutes. The reaction liquid was mixed with an appropriate amount of saturated brine, extracted with ethyl acetate, dried with anhydrous magnesium sulfate and then concentrated to obtain a formyl inter mediate as yellow foam. This was dissolved in 5 ml of methylene chloride, 60 μl of morpholine and 0.3 ml of acetic acid were added thereto in that order, and then 0.22 g of triacetoxy sodium borohydride was added thereto under ice-cooling, and the mixture was stirred at room temperature for about 30 minutes. After evaporation of the solvent, the residue was mixed with an appropriate amount of sodium bicarbonate, extracted several times with ethyl acetate, dried with anhydrous magnesium sulfate and concentrated. The thus formed residue was purified by a silica gel column chromatography to obtain 0.16 g (60%) of 2-(1,3-dihydro-2H-benzimidazol-2-ylidene)-1-(3- fluorophenyl)-{3-[2-(morpholin-4-ylmethyl)-1,3-dioxolan-4-yl]phenyl}propane-1,3-dione as a yellow foam from an ethyl acetate eluate. FA: 530

Example 11-1

0.33 ml portion of 2-bromopyridine was dissolved in 3 ml of THF, and the solution was cooled to −78° C., mixed with 2.2 ml of n-butyl lithium and then stirred at the same temperature for 30 minutes. This solution was poured at −78° C. into a solution prepared by dissolving 3-[2-(1,3-dihydro-2H-benzimidazol-2-ylidene)-3-(3-fluorophenyl)-3-oxopropanoyl]benzaldehyde in 10 ml of THF. This was slowly risen to room temperature and mixed with 50 ml of saturated ammonium chloride aqueous solution. This was extracted with ethyl acetate, dried with sodium sulfate and then concentrated, and the thus formed residue was purified by a silica gel column chromatography (chloroform:methanol=from 100:0 to 90:10). By subjecting the thus obtained reddish brown solid to salt formation with 4N HCl/EtOAC (0.2 ml), 151 mg (42%) of 2-(1,3-dihydro-2H-benzimidazol-2-ylidene)-1-(3-fluorophenyl)-3-{3-[hydroxy(pyridin-2-yl)methyl]phenyl}propane-1,3-dione hydrochloride (Example 11-1) was obtained. FA: 466

In the same manner, 2-(1,3-dihydro-2H-benzimidazol-2-ylidene)-1-(3-fluorophenyl)-3-{3-[hydroxy(1-methyl-1H-imidazol-2-yl)methyl]phenyl}propane-1,3-dione hydrochloride (Example 11-2) was obtained. FA: 469

Example 12

A 2 ml portion of DMSO solution containing 100 mg of 1-[3-(chloromethyl)phenyl]-3-(3,5-difluorophenyl)-2-(1,3-dihydro-2H-benzimidazol-2-ylidene)propane-1,3-dione was mixed with 35 mg of potassium acetate and stirred at room temperature for about 2 days. The reaction liquid was mixed with an appropriate amount of saturated ammonium chloride aqueous solution, extracted several times with ethyl acetate, dried with anhydrous magnesium sulfate and concentrated, and then the thus formed residue was purified by a silica gel column chromatography to obtain 90 mg of a yellow oily substance from an ethyl acetate-hexane (1:2) eluate. By crystallizing this from a small amount of an ethyl acetate-hexane (1:3) at a low temperature, 68 mg (64%) of 3-[3-(3,5-difluorophenyl)-2-(1,3-dihydro-2H-benzimidazol-2-ylidene)-3-oxopropanoyl]benzylacetate was obtained as yellow crystals. FA: 449

Example 13-1

Resolution of 1-(3,5-difluorophenyl)-2-(1,3-dihydro-2H-benzimidazol-2-ylidene)-3-[3-(1,2-dihydroxyethyl)phenyl]propane-1,3-dione was carried out in the usual way using a chiral column: CHIRALCEL OD-H (trade name, Daicel Chemical Industries) and an eluent: hexane/ethanol 3:1. 1-(3,5-Difluorophenyl)-2-(1,3-dihydro-2H-benzimidazol-2-ylidene)-3-{3-[(1S)-1,2-dihydroxyethyl]phenyl}propane-1,3-dione (Example 13-1) was obtained as the isomer having shorter retention time.

FA: 437

Example 13-1

$[\alpha]_D$ +21.3° (c 0.356 MeOH)

Also, 1-(3,5-difluorophenyl)-2-(1,3-dihydro-2H-benzimidazol-2-ylidene)-3-{3-[(1R)-1,2-dihydroxyethyl]phenyl} propane-1,3-dione (Example 13-2) was obtained as the isomer having longer retention time. FA: 437, N1: 3.27 (2H, m), 4.42 (1H, m), 4.71 (1H, t, J=6 Hz), 5.17 (1H, d, J=4 Hz), 6.91 (3H, m), 7.14 (3H, m), 7.30 (3H, m), 7.74 (2H, m), 13.11 (2H, s), mp: 189-190° C.

Example 13-2

$[\alpha]_D$ −21.2° (c 0.367 MeOH)

Example 14-1

A 568 mg portion of 1-[3-(2-azido-1-hydroxyethyl)phenyl]-3-(3,5-difluorophenyl)-2-(1,3-dihydro-2H-benzimidazol-2-ylidene)propane-1,3-dione and 120 mg of 10% palladium-carbon were added to 50 ml of ethyl acetate and stirred at room temperature for 8.5 hours under ordinary pressure and in an atmosphere of hydrogen. This was filtered through celite, concentrated, mixed with diethyl ether and then extracted with water. By concentrating the water layer, 250 mg (47%) of 1-[3-(2-amino-1-hydroxyethyl)phenyl]-3-(3,5-difluorophenyl)-2-(1,3-dihydro-2H-benzimidazol-2-ylidene)propane-1,3-dione (Example 14-1) was obtained as a yellow solid. FA: 436

In the same manner, the following compounds were obtained.

Example 14-2

2-(1,3-dihydro-2H-benzimidazol-2-ylidene)-1-[3-(2-ethyl-1,3-dioxolan-4-yl)phenyl]-3-(3-fluorophenyl)propane-1,3-dione FA: 459

Example 14-3

1-(3,5-difluorophenyl)-3-{3-[(1R)-1,2-dihydroxy-ethyl]-2-fluorophenyl}-2-(5-hydroxy-1,3-dihydro-2H-benzimidazol-2-ylidene)propane-1,3-dine FA: 471

Example 15-1

A 137 mg portion of 1-[3-(2-amino-1-hydroxyethyl)phenyl]-3-(3,5-difluorophenyl)-2-(1,3-dihydro-2H-benzimidazol-2-ylidene)propane-1,3-dione was dissolved in 10 ml of pyridine, and 35 mg of acetic anhydride was added thereto under ice-cooling. After 2.5 hours of stirring at room temperature, the reaction liquid was mixed with an appropriate amount of sodium bicarbonate aqueous solution, extracted with ethyl acetate, dried with anhydrous sodium sulfate and concentrated, and then the thus formed residue was purified by a silica gel column chromatography to obtain 120 mg (80%) of N-(2-{3-[3-(3,5-difluorophenyl)-2-(1,3-dihydro-2H-benzimidazol-2-ylidene)-3-oxopropanoyl]phenyl}-2-hydroxyethyl)acetamide (Example 15-1) as a yellow foam from a chloroform-methanol (30:1) eluate. FA: 478

The following compounds were obtained in the same manner.

Example 15-2

2-{3-[2-(1,3-dihydro-2H-benzimidazol-2-ylidene)-3-(3-fluorophenyl)-3-oxopropanoyl]phenyl}-2-hydroxyethyl ethylcarbonate FA: 491

Example 15-3

1-{3-[2-(1,3-dihydro-2H-benzimidazol-2-ylidene)-3-(3-fluorophenyl)-3-oxopropanoyl]phenyl}-2-hydroxyethyl acetate FA: 461

Example 15-4

2-(acetyloxy)-2-{3-[2-(1,3-dihydro-2H-benzimidazol-2-ylidene)-3-(3-fluorophenyl)-3-oxopropanoyl]phenyl}ethyl(dimethylamino) acetate FA: 546

Example 16

A 300 mg portion of 2-(1,3-dihydro-2H-benzimidazol-2-ylidene)-1-[3-(1,2-dihydroxyethyl)phenyl]-3-(3-fluorophenyl)propane-1,3-dione and 200 mg of 1,1'-carbonyldiimidazole were dissolved in 7 ml of Tol and stirred at 80° C. for 12 hours. After concentration of the reaction liquid, the thus formed residue was purified by a silica gel column chromatography to obtain 30 mg (9%) of 2-(1,3-dihydro-2H-benzimidazol-2-ylidene)-1-(3-fluorophenyl)-3-[3-(2-oxo-1,3-dioxolan-4-yl)phenyl]propane-1,3-dione as a yellow solid from a chloroform-methanol (10:1) eluate. ES+: 445

Example 17

In accordance with the aforementioned method of Example 1, 1-(3,5-difluorophenyl)-2-(1,3-dihydro-2H-benzimidazol-2-ylidene)-3-[3-(2,2-dimethyl-1,3-dioxolan-4-yl)phenyl]propane-1,3-dione was obtained. ES+: 491

Example 18

A 0.12 g portion of 2-[bis(methylsulfanyl)methylene]-1-[(3-((4R)-2,2-dimethyl-1,3-dioxolan-4-yl)-2-fluorophenyl]-3-pyridin-3-yl-propan-1,3-dione and 36 mg of 1,2-phenylenediamine were dissolved in 8 ml of ethanol and heated under reflux for 3 hours. After concentration of the reaction liquid, the thus formed residue was purified by a silica gel column chromatography to obtain 0.12 g (97%) of 2-(1,3-dihydro-2H-benzimidazol-2-ylidene)-1-{3-[(4R)-2,2-dimethyl-1,3-dioxolan-4-yl]-2-fluorophenyl}-3-pyridin-3-yl-propane-1,3-dione as a yellow solid from an ethyl acetate-hexane (3:1) eluate. FA: 460

Test Example 1

Test on GnRH Receptor Antagonism

GnRH receptor antagonism of the compounds of the invention was evaluated by calculating their concentration for inhibiting 50% of the binding of $^{125}$I-D-Trp$^{6}$-LHRH to human GnRH receptor ($IC_{50}$ value), in accordance with the 1. GnRH receptor antagonism test method described on p. 56 of the Patent Reference 1.

The results are shown in Table 25.

Test Example 2

Measurement of Blood Concentration of a Compound by Ex Vivo Binding Assay

Each compound to be tested was dissolved or suspended in 0.5% methyl cellulose (MC) solution and was orally administered to Wistar male rat of 9 weeks of age (SLC Japan) at a dose of 10 mg/kg. Blood sample was collected after 2 hours of the administration to obtain serum.

Each serum sample was mixed with the same volume of methanol to remove protein and optionally diluted with an assay buffer, and then the $^{125}$I-D-Trp$^{6}$-LHRH binding inhibition ratio was measured in the same manner as in Test Example 1. Using a separately prepared calibration curve on the concentration-binding inhibition of compounds to be tested, blood concentration of each compound (μM) was calculated from the binding inhibition ratio.

The results are shown in Table 25.

TABLE 25

| Test compounds | Test Example 1 GnRH receptor antagonism (A) $IC_{50}$ (nM) | Test Example 2 Blood compound concentration (B) 2 hour value (μM) | (B)/(A)* |
|---|---|---|---|
| Ex 2-3 | 0.082 | 0.71 | 8.7 |
| Ex 2-4 | 0.17 | 1.31 | 7.7 |
| Ex 2-5 | 0.10 | 0.82 | 8.2 |
| Ex 2-7 | 0.19 | 1.65 | 8.7 |
| Ex 2-12 | 0.15 | 0.92 | 6.1 |
| Ex 2-20 | 0.20 | 1.14 | 5.7 |
| Ex 2-48 | 0.22 | 2.16 | 9.8 |
| Ex 2-50 | 0.12 | 0.88 | 7.3 |
| Ex 4-1 | 0.093 | 1.36 | 14.6 |
| Ex 4-4 | 0.10 | 1.04 | 10.4 |
| Ex 4-5 | 0.12 | 3.74 | 31.2 |
| Ex 4-8 | 0.081 | 1.79 | 22.1 |
| Ex 4-15 | 0.076 | 1.44 | 19.0 |
| Ex 4-21 | 0.24 | 2.17 | 9.0 |
| Ex 4-22 | 0.13 | 2.17 | 16.7 |
| Ex 4-23 | 0.18 | 1.11 | 6.2 |
| Ex 4-25 | 0.14 | 1.39 | 9.9 |
| Ex 4-29 | 0.19 | 6.44 | 33.9 |
| Ex 4-30 | 0.10 | 1.5 | 15.0 |
| Ex 4-32 | 0.12 | 0.67 | 5.6 |
| Ex 4-33 | 0.12 | 1.59 | 13.3 |
| Control compound 1 | 0.95 | 1.49 | 1.6 |
| Control compound 2 | 0.97 | 1.29 | 1.3 |
| Control compound 3 | 0.19 | 0.04 | 0.21 |

Control compound 1: Ex 40 described in Patent Reference 1
Control compound 2: Ex 251 described in Patent Reference 1
Control compound 3: Ex 239 described in Patent Reference 1
*Shows the ratio of blood compound concentration (B) to GnRH receptor antagonism (A)

It is considered that strength of the action of a GnRH receptor antagonist in the living body depends on both of the receptor inhibitory activity and the blood drug concentration, and that a compound having larger ratio of blood drug concentration to in vitro receptor inhibitory activity has stronger drug effect in the living body.

Since the compounds of the invention have GnRH receptor antagonism which is similar to or larger than that of the compounds disclosed in Patent Reference 1, and the value of (B)/(A) as a ratio of blood concentration to receptor inhibitory activity is further improved, it was confirmed that their effect in the living body can be expected. For example, in Table 25, when the blood concentration is higher, the value of IC50 on the antagonism activity is smaller, and the value of the drug effect became larger and stronger will be shown.

Test Example 3

Test on Antagonism for GnRH-Induced Blood Testosterone Increasing Reaction

In vivo GnRH receptor antagonism of the compounds of the invention was evaluated in accordance with the method described in “2. Test on antagonism for GnRH-induced blood testosterone increasing reaction” on p. 57 of the Patent Reference 1. Each compound to be tested was suspended in 0.5% methyl cellulose (MC) aqueous solution and orally administered at a dose of 10 mg/kg 2 or 4 hours before the administration of GnRH. The compounds of the invention had good antagonism.

Test Example 4

Test on Cytochrome P450 (CYP3A4) Enzyme Inhibition

Evaluation of Drug Interaction (1) Inhibition Test I (Calculation of Inhibitory Activity I)

Using a 96 well plate, a substrate (midazolam), a test compound and human liver microsome (0.1 mg protein/ml) were incubated at 37° C. for 20 minutes in 100 mM phosphate buffer containing 0.1 mM EDTA and 1 mM NADPH. Thereafter, the reaction was stopped by adding an aqueous solution containing 80% acetonitrile. Thereafter, each sample was analyzed by HPLC, and the inhibitory activity I was calculated using the following formula. As a result of this test, for example, the compounds of Table 26 showed superior actions in comparison with the compounds of Ex 251 described in Patent Reference 1.

$$\text{Inhibitory activity } I(\%)=100-V_{i.I}/V_{0.I}\times100$$

$V_{i.I}$: metabolic rate of substrate in the presence of a test compound of known concentration in the inhibition test I $V_{0.I}$: metabolic rate of substrate in the absence of test compound in the inhibition test I

TABLE 26

| Ex No. | CYP3A4 Inhibitory activity I (%) | Ex No. | CYP3A4 Inhibitory activity I (%) |
|---|---|---|---|
| 2-3 | 2 | 2-54 | 7 |
| 2-4 | −8 | 2-50 | −10 |
| 2-5 | −7 | 2-56 | 13 |
| 2-7 | −5 | 2-57 | −12 |
| 2-11 | −5 | 2-58 | 2 |
| 2-15 | −5 | 2-62 | −10 |
| 2-18 | 6 | 2-65 | −5 |
| 2-20 | 18 | 4-4 | −10 |
| 2-21 | 17 | 4-9 | −1 |
| 2-23 | 15 | 4-14 | −6 |
| 2-28 | −5 | 4-15 | 4 |
| 2-29 | 14 | 4-18 | 2 |
| 2-33 | −9 | 4-21 | 4 |
| 2-34 | 1 | 4-22 | −9 |
| 2-37 | −1 | 4-23 | −3 |
| 2-38 | −4 | 4-25 | 1 |
| 2-39 | 0 | 4-28 | 9 |
| 2-43 | −2 | 4-29 | −8 |

TABLE 26-continued

| Ex No. | CYP3A4 Inhibitory activity I (%) | Ex No. | CYP3A4 Inhibitory activity I (%) |
|---|---|---|---|
| 2-46 | −9 | 4-30 | 9 |
| 2-47 | 4 | Control compound 1 | 40 |
| 2-48 | 4 | Control compound 2 | 53 |
| 2-49 | −2 | Control compound 3 | 58 |
| 2-50 | −8 | | |

(2) Inhibition Test II (Calculation of Inhibitory Activity II)

Using a 96 well plate, a test compound and human liver microsome (0.1 mg protein/ml) were incubated at 37° C. for 30 minutes in 145 μl in total volume of 100 mM phosphate buffer (pH=7.4) containing 0.1 mM EDTA and 1 mM NADPH. Thereafter, midazolam as the substrate was added thereto and incubated at 37° C. for 20 minutes. After the incubation, the reaction was stopped by adding an aqueous solution containing 80% acetonitrile. Thereafter, each sample was analyzed by HPLC, and the inhibitory activity II was calculated.

$$\text{Inhibitory activity } II(\%)=100-V_{i.II}/V_{0.II}/(100-\text{inhibitory activity } I)\times100\times100$$

$V_{i.II}$: metabolic rate of substrate in the presence of a test compound of known concentration in the inhibition test II $V_{0.II}$: metabolic rate of substrate in the absence of test compound in the inhibition test II As a result of this test, for example, the compounds of Ex 2-4, Ex 4-1, Ex 4-4, Ex 4-5, Ex 4-21, Ex 4-22, Ex 4-25, Ex 4-29 and Ex 4-30 showed superior actions in comparison with the compounds of Ex 40, Ex 251 and Ex 239 described in Patent Reference 1.

Test Example 5

Test on Metabolic Stability in Human Liver Microsome

Using a test tube, a test compound and human liver microsome (0.2 mg protein/ml) were incubated at 37° C. for 15 minutes in 100 mM phosphate buffer (pH=7.4) containing 0.11 mM EDTA and 1 mM NADPH. After the incubation, the reaction was stopped by adding an aqueous solution containing 80% acetonitrile. Thereafter, each sample was analyzed by HPLC, and the in vitro clearance was calculated with a integration plot.

As a result of this test, for example, the compounds of Ex 2-4, Ex 4-1, Ex 4-4, Ex 4-5, Ex 4-21, Ex 4-22, Ex 4-25, Ex 4-29 and Ex 4-30 showed superior metabolic stability in human liver and were less likely to suffer from first pass effect in comparison with the compounds of Ex 40, Ex 251 and Ex 239 described in Patent reference 1.

What is claimed is:

1. A propane-1,3-dione derivative represented by the formula (I) or a pharmaceutically acceptable salt thereof (I)

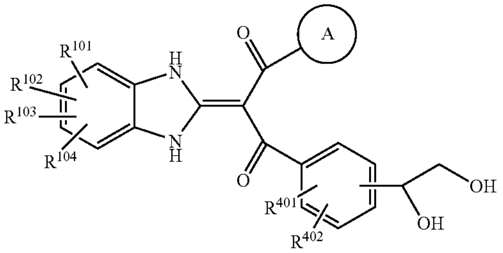

symbols in the formula mean as follows, ring A: benzene which may be substituted with 1 to 3 substituent groups, wherein the substituent group is halogen, CN, lower alkyl which may be substituted with halogen, —O-lower alkyl, —CO—O— lower alkyl or amino, $R^{401}$ and $R^{402}$: may be the same or different from each other and each is H, halogen, OH, —O-lower alkyl, or lower alkyl, $R^{101}$, $R^{102}$, $R^{103}$ and $R^{104}$: may be the same or different from one another and each is H, halogen, OH, or —O-lower alkyl which may be substituted with aryl or heteroaryl.

2. A propane-1,3-dione derivative represented by the formula (Ia) or a pharmaceutically acceptable salt thereof (Ia)

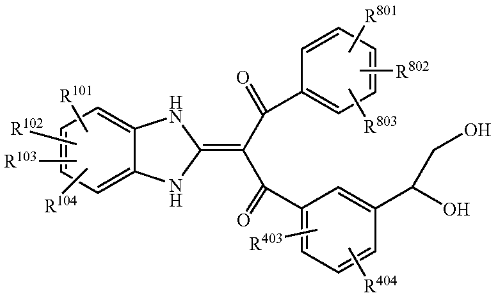

symbols in the formula mean as follows, $R^{801}$, $R^{802}$ and $R^{803}$: may be the same or different from one another and each is H, halogen or lower alkyl, $R^{403}$ and $R^{404}$: may be the same or different from each other and each is H, halogen or lower alkyl, and, $R^{101}$, $R^{102}$, $R^{103}$ and $R^{104}$: may be the same or different from one another and each is H, halogen, OH, or —O-lower alkyl which may be substituted with aryl or heteroaryl.

3. The propane-1,3-dione derivative or a pharmaceutically acceptable salt thereof according to claim 2, which is at least one compound selected from the group consisting of:

2-(1,3-Dihydro-2H-benzimidazol-2-ylidene)-1-[3-(1,2-dihydroxyethyl)phenyl]-3-(3,4,5-trifluorophenyl)propane-1,3-dione; 1-{2-butyl-3-[(1R)-1,2-dihydroxyethyl]phenyl}-2-(1,3-dihydro-2H-benzimidazol-2-ylidene)-3-(3-fluorophenyl)propane-1,3-dione; 1-(3,5-difluorophenyl)-2-(1,3-dihydro-2H-benzimidazol-2-ylidene)-3-[5-(1,2-dihydroxyethyl)-2-fluorophenyl]propane-1,3-dione; 1-(3,5-difluorophenyl)-2-(1,3-dihydro-2H-benzimidazol-2-ylidene)-3-{3-[(1R)-1,2-dihydroxyethyl]-2-methylphenyl}propane-1,3-dione; 2-(1,3-dihydro-2H-benzimidazol-2-ylidene)-1-{3-[(1R)-1,2-dihydroxyethyl]-2-methylphenyl}-3-(2-fluorophenyl)propane-1,3-dione; 2-(1,3-dihydro-2H-benzimidazol-2-ylidene)-1-[3-(1,2-dihydroxyethyl)phenyl]-3-(2,3,5-trifluorophenyl)propane-1,3-dione; 2-(1,3-dihydro-2H-benzimidazol-2-ylidene)-1-{3-[(1R)-1,2-dihydroxyethyl]-2-methylphenyl}-3-(3-methylphenyl)propane-1,3-dione; 1-{2-chloro-3-[(1R)-1,2-dihydroxyethyl]phenyl}-2-(1,3-dihydro-2H-benzimidazol-2-ylidene)-3-(3-fluorophenyl)propane-1,3-dione; 2-(1,3-dihydro-2H-benzimidazol-2-ylidene)-1-{3-[(1R)-1,2-dihydroxyethyl]phenyl}-3-(3-fluorophenyl)propane-1,3-dione; 1-(3,5-difluorophenyl)-2-(1,3-dihydro-2H-benzimidazol-2-ylidene)-3-[3-(1,2-dihydroxyethyl)-2-fluorophenyl]propane-1,3-dione; 1-(3,5-difluorophenyl)-2-(1,3-dihydro-2H-benzimidazol-2-ylidene)-3-[3-(1,2-dihydroxyethyl)-4-fluorophenyl]propane-1,3-dione; 1-{2-chloro-3-[(1R)-1,2-dihydroxyethyl]phenyl}-3-(3,5-difluorophenyl)-2-(1,3-dihydro-2H-benzimidazol-2-ylidene)propane-1,3-dione; 2-(1,3-dihydro-2H-benzimidazol-2-ylidene)-1-{3-[(1R)-1,2-dihydroxyethyl]-2-fluorophenyl}-3-(3-fluorophenyl)propane-1,3-dione; 1-{2-chloro-3-[(1R)-1,2-dihydroxyethyl]phenyl}-3-(3-chlorophenyl)-2-(1,3-dihydro-2H-benzimidazol-2-ylidene)propane-1,3-dione.

4. The propane-1,3-dione derivative or a pharmaceutically acceptable salt thereof according to claim 1, wherein ring A is benzene which may be substituted with 1 to 3 substituent groups, wherein the substituent groups may be the same or different from each other and each is halogen or lower alkyl.

5. The propane-1,3-dione derivative or a pharmaceutically acceptable salt thereof according to claim 4, wherein $R^{401}$ and $R^{402}$ may be the same or different from each other and each is H, halogen, or lower alkyl.

6. The propane-1,3-dione derivative or a pharmaceutically acceptable salt thereof according to claim 5, wherein $R^{101}$, $R^{102}$, $R^{103}$ and $R^{104}$ are each H.

7. The propane-1,3-dione derivative or a pharmaceutically acceptable salt thereof according to claim 2, wherein $R^{101}$, $R^{102}$, $R^{103}$ and $R^{104}$ are each H.

8. 2-(1,3-dihydro-2H-benzimidazol-2-ylidene)-1-[3-(1,2-dihydroxyethyl)phenyl]-3-(3,4,5-trifluorophenyl)propane-1,3-dione or a pharmaceutically acceptable salt thereof.

9. 1-{2-butyl-3-[(1R)-1,2-dihydroxyethyl]phenyl}-2-(1,3-dihydro-2H-benzimidazol-2-ylidene)-3-(3-fluorophenyl)propane-1,3-dione or a pharmaceutically acceptable salt thereof.

10. 1-(3,5-difluorophenyl)-2-(1,3-dihydro-2H-benzimidazol-2-ylidene)-3-[5-(1,2-dihydroxyethyl)-2-fluorophenyl]propane-1,3-dione or a pharmaceutically acceptable salt thereof.

11. 1-(3,5-difluorophenyl)-2-(1,3-dihydro-2H-benzimidazol-2-ylidene)-3-{3-[(1R)-1,2-dihydroxyethyl]-2-methylphenyl}propane-1,3-dione or a pharmaceutically acceptable salt thereof.

12. 2-(1,3-dihydro-2H-benzimidazol-2-ylidene)-1-{3-[(1R)-1,2-dihydroxyethyl]-2-methylphenyl}-3-(2-fluorophenyl)propane-1,3-dione or a pharmaceutically acceptable salt thereof.

13. 2-(1,3-dihydro-2H-benzimidazol-2-ylidene)-1-[3-(1,2-dihydroxyethyl)phenyl]-3-(2,3,5-trifluorophenyl)propane-1,3-dione or a pharmaceutically acceptable salt thereof.

14. 2-(1,3-dihydro-2H-benzimidazol-2-ylidene)-1-{3-[(1R)-1,2-dihydroxyethyl]-2-methylphenyl}-3-(3-methylphenyl)propane-1,3-dione or a pharmaceutically acceptable salt thereof.

15. 1-{2-chloro-3-[(1R)-1,2-dihydroxyethyl]phenyl}-2-(1,3-dihydro-2H-benzimidazol-2-ylidene)-3-(3-fluorophenyl)propane-1,3-dione or a pharmaceutically acceptable salt thereof.

16. 2-(1,3-dihydro-2H-benzimidazol-2-ylidene)-1-{3-[(1R)-1,2-dihydroxyethyl]phenyl}-3-(3-fluorophenyl)propane-1,3-dione or a pharmaceutically acceptable salt thereof.

17. 1-(3,5-difluorophenyl)-2-(1,3-dihydro-2H-benzimidazol-2-ylidene)-3-[3-(1,2-dihydroxyethyl)-2-fluorophenyl] propane-1,3-dione or a pharmaceutically acceptable salt thereof.

18. 1-(3,5-difluorophenyl)-2-(1,3-dihydro-2H-benzimidazol-2-ylidene)-3-[3-(1,2-dihydroxyethyl)-4-fluorophenyl] propane-1,3-dione or a pharmaceutically acceptable salt thereof.

19. 1-{2-chloro-3-[(1R)-1,2-dihydroxyethyl]phenyl}-3-(3,5-difluorophenyl)-2-(1,3-dihydro-2H-benzimidazol-2-ylidene)propane-1,3-dione or a pharmaceutically acceptable salt thereof.

20. 2-(1,3-dihydro-2H-benzimidazol-2-ylidene)-1-{3-[(1R)-1,2-dihydroxyethyl]-2-fluorophenyl}-3-(3-fluorophenyl)propane-1,3-dione or a pharmaceutically acceptable salt thereof.

21. 1-{2-chloro-3-[(1R)-1,2-dihydroxyethyl]phenyl}-3-(3-chlorophenyl)-2-(1,3-dihydro-2H-benzimidazol-2-ylidene)propane-1,3-dione or a pharmaceutically acceptable salt thereof.

* * * * *